United States Patent
Prichard et al.

(10) Patent No.: US 12,391,991 B2
(45) Date of Patent: *Aug. 19, 2025

(54) **MARKERS TO PREDICT MACROCYCLIC LACTONE DRUG RESISTANCE IN *DIROFILARIA IMMITIS*, THE CAUSATIVE AGENT OF HEARTWORM DISEASE**

(71) Applicants: Elanco US Inc., Indianapolis, IN (US); McGill University, Montreal (CA)

(72) Inventors: Roger K. Prichard, Quebec (CA); Catherine Bourguinat, Quebec (CA); Timothy G. Geary, Quebec (CA)

(73) Assignees: Elanco US Inc., Indianapolis, IN (US); McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/877,830

(22) Filed: Jul. 29, 2022

(65) Prior Publication Data

US 2024/0240252 A1    Jul. 18, 2024

Related U.S. Application Data

(60) Division of application No. 15/887,164, filed on Feb. 2, 2018, now Pat. No. 11,414,703, which is a continuation of application No. 14/896,736, filed as application No. PCT/US2014/044000 on Jun. 25, 2014, now Pat. No. 10,000,811.

(60) Provisional application No. 61/839,545, filed on Jun. 26, 2013.

(51) Int. Cl.
*C12Q 1/68* (2018.01)
*C07H 21/04* (2006.01)
*C12Q 1/6883* (2018.01)
*C12Q 1/6888* (2018.01)

(52) U.S. Cl.
CPC .......... *C12Q 1/6883* (2013.01); *C12Q 1/6888* (2013.01); *C12Q 2600/124* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS 10,000,811 B2 * 6/2018 Prichard .............. C12Q 1/6883

OTHER PUBLICATIONS

Bourguinat et al. Veterinary Parasitology, vol. 17, pp. 368-373, Mar. 2011 (Year: 2011).*

* cited by examiner

*Primary Examiner* — Jeanine A Goldberg
(74) *Attorney, Agent, or Firm* — Barnes & Thornburg LLP

(57) ABSTRACT

Disclosed are nucleic acid molecules from the genome of *Dirofilaria* spp. nematodes that contain single nucleotide polymorphisms related to reduced responsiveness of the nematodes to macrocyclic lactones. In one example, the species of *Dirofilaria* is *Dirofilaria immitis* (the agent of heartworm in animals). Also disclosed are methods for determining the responsiveness of *Dirofilaria* spp. nematodes to macrocyclic lactones, methods for selecting a treatment to treat an animal infected with *Dirofilaria* spp. nematode, and kits for determining the responsiveness of *Dirofilaria* spp. nematodes to macrocyclic lactones.

16 Claims, 29 Drawing Sheets

Specification includes a Sequence Listing.

Table 1. Genotype frequencies for markers representing SEQ ID NOs: 110-127

| SNP Loci | % Genotype Frequency Susceptible | | | % Genotype Frequency Confirmed Resistant | | | Comparison Susceptible/Confirmed Resistant p-value | % Genotype Frequency Confirmed Resistant + LOE | | | Comparison Susceptible/Confirmed Resistant + LOE p-value |
|---|---|---|---|---|---|---|---|---|---|---|---|
| | CC | CT | TT | CC | CT | TT | | CC | CT | TT | |
| MARKER_31307* | | | 100.0% | 2.9% | 11.7% | 85.4% | 6.3E-05 | 8.7% | 8.7% | 82.6% | 5.7E-06 |
| MARKER_26225* | | 0.7% | 99.3% | 1.3% | 48.3% | 50.3% | 3.7E-21 | 1.9% | 47.2% | 50.9% | 1.2E-23 |
| MARKER_47722_B* | 6.5% | 1.3% | 92.3% | 22.7% | 33.7% | 43.6% | 5.0E-20 | 18.9% | 23.5% | 57.6% | 2.9E-14 |
| MARKER_58162_B | 0.7% | 1.5% | 97.8% | 26.7% | 18.6% | 54.7% | 1.8E-16 | 30.7% | 14.7% | 54.6% | 1.0E-18 |
| | AA | AG | GG | AA | AG | GG | | AA | AG | GG | |
| MARKER_17709* | 100.0% | | | 74.1% | 19.0% | 6.8% | 4.3E-02 | 67.3% | 17.5% | 15.1% | NS |
| MARKER_47141* | 100.0% | | | 56.7% | 43.3% | | 4.7E-23 | 68.8% | 27.7% | 3.5% | 3.5E-16 |
| MARKER_48750_A | 100.0% | | | 54.9% | 28.7% | 16.5% | 1.3E-15 | 54.1% | 24.8% | 21.0% | 1.9E-17 |
| MARKER_63962 | 100.0% | | | 87.7% | 11.7% | 0.6% | 1.0E-03 | 81.9% | 11.8% | 6.2% | 1.7E-05 |
| MARKER_6372 | 90.2% | 2.3% | 7.5% | 20.2% | 49.7% | 30.1% | 1.8E-32 | 35.8% | 32.9% | 31.3% | 2.0E-26 |
| MARKER_15611* | 90.5% | | 9.5% | 53.3% | 26.7% | 20.0% | 9.3E-14 | 47.7% | 15.9% | 36.4% | 6.9E-19 |
| | AA | AT | TT | AA | AT | TT | | AA | AT | TT | |
| MARKER_46432 | | | 100.0% | 0.8% | 15.0% | 84.2% | 8.2E-05 | 3.2% | 10.3% | 86.5% | 3.0E-04 |
| MARKER_29594 | 1.2% | 8.7% | 90.1% | 12.7% | 32.9% | 54.4% | 1.5E-12 | 12.4% | 20.8% | 66.8% | 1.4E-08 |
| | CC | CG | GG | CC | CG | GG | | CC | CG | GG | |
| MARKER_26784 | | | 100.0% | 16.8% | 7.2% | 76.0% | 1.4E-07 | 10.1% | 4.4% | 85.4% | 1.0E-04 |
| MARKER_51661 | 100.0% | | | 45.5% | 39.4% | 15.2% | 2.7E-23 | 48.9% | 29.0% | 22.1% | 2.7E-24 |
| MARKER_7819* | 94.9% | 1.9% | 3.2% | 45.2% | 39.2% | 15.7% | 3.1E-21 | 53.6% | 23.5% | 23.0% | 3.1E-19 |
| MARKER_26704* | 90.4% | 4.5% | 5.1% | 70.2% | 27.4% | 2.4% | 2.5E-08 | 65.8% | 22.7% | 11.5% | 2.2E-09 |
| | AA | AC | CC | AA | AC | CC | | AA | AC | CC | |
| MARKER_14329 | 1.1% | 6.1% | 92.8% | 6.4% | 14.0% | 79.7% | 9.9E-04 | 17.4% | 20.4% | 62.2% | 1.0E-13 |
| | GG | GT | TT | GG | GT | TT | | GG | GT | TT | |
| MARKER_56169 | | | 100.0% | 16.0% | 1.3% | 82.7% | 5.0E-03 | 21.8% | 1.1% | 77.1% | 4.8E-04 |

*For markers designated with an asterisk (*), the genotype indicated shows analysis of the reverse complement of the sequences shown as SEQ ID NOs: 110-127.

Figure 29

SEQUENCE LISTING

```
Sequence total quantity: 127
SEQ ID NO: 1            moltype = DNA  length = 300
FEATURE                 Location/Qualifiers
source                  1..300
                        mol_type = genomic DNA
                        organism = Dirofilaria immitis
SEQUENCE: 1
aacataaaca tattgaactg aatcctgcaa acagttctct tataacgtga accataacta  60
aatttagaga aaatatgaaa aagaaaaata agttgctttt gctcgtgcac caactctaat  120
acccaggaaa tcaagaagtg ataatgagta atgtcatcat tagattcagt aattggtgac  180
actatcaata ttattattat tatacttaaa aatacgacga ccacttatcg taacttaaag  240
catgcataat acgactgtca tcatattaca tttcttcaag ttcgtattgg acaagtgatt  300

SEQ ID NO: 2            moltype = DNA  length = 300
FEATURE                 Location/Qualifiers
source                  1..300
                        mol_type = genomic DNA
                        organism = Dirofilaria immitis
SEQUENCE: 2
gacaagcgtt gacgggagag acgatataat aataaagaag gcattgggta tcagaaggca  60
caatccaatt ataaatgcca aggcaaaatg aataaaattt atgctgacga tttgatcaat  120
tacgaagaat ttccgatcgg ctcgaatctt tgtttgtatg tgcactactg ttaacttaat  180
ctttgtttta tatactttg cgtgtcatat ataatatatt catgtcaact gatacgttat  240
gatgtttttt tgtaaattaa gttgatcgga aacctgaagt ctatttcaaa tttaagaaat  300

SEQ ID NO: 3            moltype = DNA  length = 300
FEATURE                 Location/Qualifiers
source                  1..300
                        mol_type = genomic DNA
                        organism = Dirofilaria immitis
SEQUENCE: 3
ttttaggaaa atggtgactg tagagagata ttatcggaac gacaaggtcc acttcgaacg  60
ggtcttttat tgtcgacgga ttgtgaacca agttttggca ttcataatga caggtagcta  120
tttttccatc atcccatttt tgtattagtg caagcaagtc atgagtcgaa agaaaatctc  180
aaaagaaaaa aatgaaattt caggttcaaa ggactgcgtc cattattcgc actggttgat  240
gagaacgtac agattccaga gcggcaatgc tgcacagtat cttttgtttc acttctgaat  300

SEQ ID NO: 4            moltype = DNA  length = 300
FEATURE                 Location/Qualifiers
source                  1..300
                        mol_type = genomic DNA
                        organism = Dirofilaria immitis
SEQUENCE: 4
tcgattaaaa attatcatcg ataaaattct aaaatttatt ttagtaaaat tattattatt  60
ttgatgaata agttaacaaa aaaattttaa taactttttg attcgccaaa aatctaattc  120
gttaaaaagt cgttccaaac agatatcgct tgttcgatga aaatgtccgg ttgttagaaa  180
atcataaatt ggttcaaata attttccaga acgttcgaaa aaatattccc ttgtatcgga  240
taaataacca ttacaatttt ccactcgtgt tgcatgtgtt tctcgacaaa aatcagctaa  300

SEQ ID NO: 5            moltype = DNA  length = 300
FEATURE                 Location/Qualifiers
source                  1..300
                        mol_type = genomic DNA
                        organism = Dirofilaria immitis
SEQUENCE: 5
tcaacagaaa tcgagattcc aaaaagtttc ctacaaatac ttaattatca atggatattt  60
agttttgtta tctgttatca taagttctgc ttcttacacg attaaaaatg tccaagaatt  120
ttttactatt caaatgaggg aaataaaaaa ccaatgccaa taatatccag aaactacata  180
catctttctt ttttcgaagc tcatctattc cggccgaaaa caatgaagaa cattaaaatt  240
cttaaaagat agtcttagcc ttttccttga ccactatctt aactgtcagc gctaaaatgt  300

SEQ ID NO: 6            moltype = DNA  length = 300
FEATURE                 Location/Qualifiers
source                  1..300
                        mol_type = genomic DNA
                        organism = Dirofilaria immitis
SEQUENCE: 6
aatagtcgtc tcattacttt ttgactttta taattcgaga atcttatgta gtccttcact  60
ttacccttct tctgtcgaac taagaattac agcattattt tcgaatttaa tgtgtaaaag  120
acaatagcag attttgtaat tttgtgttaa cctcacttta tatttcgctt catatcgtga  180
cagagaatta ctatttcaga gagtattact tgtcaccaga gaatctccag aaagattttt  240
atttacgtcg gaaaatggac aaaaatggtt tcttatcatt agcactgata gctagtttcc  300

SEQ ID NO: 7            moltype = DNA  length = 300
FEATURE                 Location/Qualifiers
source                  1..300
                        mol_type = genomic DNA
                        organism = Dirofilaria immitis
```

```
SEQUENCE: 7
tatctcttgt tgtgtgttct gcattgtatc aaagtgggta aatttgtgctt tagacgttga    60
cttattgtct ttttaagtt atattctagt ccatgttttt ctctttgcaa atattttttt    120
ccgccgccta tgattcattg ttttgtttgt aactctctat taagttgctt ttagtttgaa    180
ttgtatcaaa atttcaaaca tttaaaatac gcactagcac tatttttttct tatctcaatt    240
aagcgaatcc cggaacaaga tttaatcgat ttccgaatca caattaaatc actggaaaac    300
```

| SEQ ID NO: 8 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 8
attttcctta acaaatcatt ttcaaacgaa aaaacattaa aaagtgttaa aataaaatgg    60
tgatattgat aagaaattaa ttcaacctgc atatcaattc ttgtagcggc cattttctta    120
gcaagttcta tagcagctcg atccatatca ccttcttgct ctaatgtcaa ttccggttcc    180
ggattttttt ttattttgcc attcttcatc tttttttat ttttactga tatagctata    240
gacccttct cccgtgcatg cctgtaggcc tgttctgata tacaggcttg tgaaccactg    300
```

| SEQ ID NO: 9 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 9
ttctgggta gttatacgga aaattagaca atgaagagaa tcaaaaaaca tgcgattttc    60
aaacagagga actttggtac ttttgcctcg acttactta ttttaaaacc catacaaaat    120
aaatgtttca tttgattgat attgtcgtac taataattag agcttcaaca ttaggatttt    180
aataaccttc aatttatttc agaatttaag aaacttacgt atggatggag aaaatataaa    240
gaatggcgat gacaaataag atttgctatg aaaaaactaa tgccacaaga tccgaatgca    300
```

| SEQ ID NO: 10 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 10
tttatgaaca aaaataataa aaattaggat aacagatatc aatttctttt agctataaat    60
atacgcttcg attgaaaaaa gctttcaaat tataattaag gcatacgtta cgatatagac    120
aattaagtcg acattaatta tttgaaatat tttaattttt ttctctttc ttttttttcta    180
ttctcttcca aagtgtcaaa tagttatgaa attgtcagaa gctaaaatga taatattatt    240
caagtttatt acctaatctt ttatcacctc atttcttatc atttatctga aaatctaatc    300
```

| SEQ ID NO: 11 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 11
atgttgaatt tttaatgaaa cttttttcggt gcataagcat tacagatctg taagctgtgc    60
aaaccctgtt tctttgtaaa ttgaaacaaa gatcatttat tgtttccagc gtcgatttga    120
cctggataaa tgtggtacca aaagtagatg acgagaggta agtgcaaaca aaatgcacaa    180
aaatgatttt gatgcactca aatcattttt aagttttgtg caattttcca ttttatagtt    240
tcgtgatcgg ttgttattca tcaacttgat tttgtttgtt ttttgtgact tatatttcat    300
```

| SEQ ID NO: 12 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 12
tttgacactt tcagatacct tacaaactca tctccagcac ccaatttaca atatcgctgc    60
ctaaataaag aatttattcg gatatgagac tgtagttttc attccgtacc aatcatagta    120
gaacagatct atagcatggt gtcctactaa agttgtgact ggctattaag tatgtgggtg    180
tttttacgtg tgcgtgggtg tttgtgcgtg tgtgcgtgtg cgtttctgca catattttcg    240
tgcgcggtgt ctgtgtgtgt ccgtttgtat atgccgagtg tagctgtgtg tatgttcttg    300
```

| SEQ ID NO: 13 | moltype = DNA  length = 300 |
|---|---|
| FEATURE | Location/Qualifiers |
| source | 1..300 |
|  | mol_type = genomic DNA |
|  | organism = Dirofilaria immitis |

```
SEQUENCE: 13
cactcataat ataccgtgtca acaaactcag aaatctgaat aaaatgacgc aaaaatgaca    60
aaaacatttt atcaaccttt tcttcatcac tccccgcat ttccaatttt cttccaaact    120
gttttttgtcg tgctacaaag tcatcagcca cttcattttc ttcaagatgg ttcgagacgc    180
cattcttgga ttcaccccctt atttcaactg tttccgaagt cccagcagtt gaagctgaac    240
ctagcattta tatcaccacc cgatgtcaaa aaatgacagc ggtcagagaa tacgacttcc    300
```

```
SEQ ID NO: 14           moltype = DNA  length = 300
FEATURE                 Location/Qualifiers
source                  1..300
                        mol_type = genomic DNA
                        organism = Dirofilaria immitis
SEQUENCE: 14
gctaggtcaa cagttggttt atttggactt atacgatatt aaacataata tcgcctcata  60
tacacagaaa tatcaaaaaa acgaacacag ctaaatcgaa gaatacgaac aaatgtttta  120
aaaattatat taaatctttt aatgctctct acaatgtcgt atcttccctt ttgtctgtat  180
ttctcctttc gttccaccac tgctatttct catgcctttg aactatggtt ctcgttgcgt  240
cgaattgtcc tcgaaactgt tgtttctgtc gaattacgtc gaactgctgg actttgtcgg  300

SEQ ID NO: 15           moltype = DNA  length = 300
FEATURE                 Location/Qualifiers
source                  1..300
                        mol_type = genomic DNA
                        organism = Dirofilaria immitis
SEQUENCE: 15
atatctcact tctgacataa attgaagtgg cactgatttg aatgaaatga taaataaaat  60
aaagacgaca aggtagtgga aaaaaaaaga ggagaaaaca ccgtttagtt ttggatgcaa  120
gctcgaatct gagttttctt gcaaaccgta cactgatcaa ttttcttaca caaacataag  180
aaaaaaagaa gtgattttac tgtagctgta tcgtataatt caaatcatat atatatatgt  240
ttcaataatc tatacattta tgtatatttt tttttgaatg gaacagtgaa tgattttaaa  300

SEQ ID NO: 16           moltype = DNA  length = 300
FEATURE                 Location/Qualifiers
source                  1..300
                        mol_type = genomic DNA
                        organism = Dirofilaria immitis
SEQUENCE: 16
acaaatgcca tcgggagaga aatatcgttg gcgtactgat cacattggcg gtatcacttc  60
tttgaaaact ccagctggta ttgtgtatca tttcatgcaa tacgctattt ttgatcgaat  120
atgtcgacgg cgtagtgttt cattttccaa cgcatcttac gttgcgtgta tggatgatga  180
cggacaatta ttggaatatc aaacaccgga tcgattgcat tccgtaacct tgaaacgtga  240
catatatggg agagtagtgc aaataacttc agatggcgaa aatattttct tcgaatatgg  300

SEQ ID NO: 17           moltype = DNA  length = 300
FEATURE                 Location/Qualifiers
source                  1..300
                        mol_type = genomic DNA
                        organism = Dirofilaria immitis
SEQUENCE: 17
ataaatatata tttccattga taatattttt catattatgt gatgtttgaa attttctgca  60
attgctacat tccgattaaa aacttttatt atccgtactg gagaattttg cttttttttg  120
acggtttgtt caataagttg tcaatatatt gtctgcctta gtaaaacctt tctaatctat  180
ccgttcgaat tggaagttga aagttcagca tcattctttt agtgaggtgt ttaagttgtt  240
caatagatat tatttagaac gatctcaatt aaaatcttct gaatgatttt atgtttttat  300

SEQ ID NO: 18           moltype = DNA  length = 300
FEATURE                 Location/Qualifiers
source                  1..300
                        mol_type = genomic DNA
                        organism = Dirofilaria immitis
SEQUENCE: 18
gcagcacatt gcacacagta aactgcaaac tgaattaaga gatattgggt tgaattattt  60
ctaatttaaa aggatataat aaatgacttt gatgattgtt gattttaagg tatctcggaa  120
gactccatca gtctcagtgc tctagcaatc gctataggta ctaaaagaaa agaaaagatg  180
tctcgttatt cactttgaaa tgtacatatc aaatcatttt gtcgtatgaa attaagtata  240
ttatgtctaa tcgtatcatt cgaaatgaat ttactgtcac tgttagaact atttaggcag  300

SEQ ID NO: 19           moltype = DNA  length = 300
FEATURE                 Location/Qualifiers
source                  1..300
                        mol_type = genomic DNA
                        organism = Dirofilaria immitis
SEQUENCE: 19
agagttcaat cgccaagttg ttcttttttct cgctcgcaga gatcaaaacg gtgttggcta  60
tacactcatt catcaggctg tgatagacat ctcttagaat ttcagtgctt ttctggatga  120
aaacattatt tctcaaacat gacacttaag gacaatagtg cgtgacttct ttgttaacgt  180
acacgagaaa acaaaacaga tgatgcttgt tatcttggtg ataaatgtgt attcagaata  240
atgttatata tctttgcgtg acaaatatca tttcgttata cttcggatac gccttttttat  300

SEQ ID NO: 20           moltype = DNA  length = 300
FEATURE                 Location/Qualifiers
source                  1..300
                        mol_type = genomic DNA
                        organism = Dirofilaria immitis
SEQUENCE: 20
aactttactt gaactttttt ggtgttcaat tttgaatatt ataccaacca ttcagaagac  60
```

```
tgtatataga aatgaacctt caagaattaa tcgaaatttt tattaaaatc ttttatttga    120
atatttcatt atttaaactc attactattt gcagtatatt attagatcta atgtagaaaa    180
aaaaatcaga tggcaaaaat aatatcatag gtttgttttt aaaattcatt gcaaaattca    240
gtgcgccgtt ccagtcgctc gtaattaccc tatccctgag ctttacaaaa agaatgcttt    300

SEQ ID NO: 21             moltype = DNA   length = 300
FEATURE                   Location/Qualifiers
source                    1..300
                          mol_type = genomic DNA
                          organism = Dirofilaria immitis
SEQUENCE: 21
aggtatctag atagcataat aaattactac acaaaccgat ggaaacgcaa gtttggcgtt    60
gcgtgttgat acaaaatatt agagccaagg atggtcatca atgtaaaact gcaattttgc    120
tatttgttta aagcaaataa gaaataaata tttcgttctt attctttaat ttatttcatc    180
agatggcttt gttataccat aattgtaaat ctgtcatatc ttaattgcgc aatagcccaa    240
gattcttgta tattcttaca tttcacaatt tattttctta tttctagttt tagaattata    300

SEQ ID NO: 22             moltype = DNA   length = 300
FEATURE                   Location/Qualifiers
source                    1..300
                          mol_type = genomic DNA
                          organism = Dirofilaria immitis
SEQUENCE: 22
aatagctact cacagcttaa gttaactaat ggattcttga atttatttaa gcgtgtagtt    60
aagcgattaa tatgatggat gcccagaatc gctttgtctt atagttttgt ctcgacagaa    120
aggatgcatt gttgtcttga atttgttcaa gggaaaatta aataggtttc ttcaatgac    180
tcctattaaa ttttttttgaa tttaggcttg cattgcgtgt tctgatccac tattagcacg    240
tacgggtatc gcagtgccat gtgatgcagc actatgcaaa aaccaccac atgtcacttg    300

SEQ ID NO: 23             moltype = DNA   length = 300
FEATURE                   Location/Qualifiers
source                    1..300
                          mol_type = genomic DNA
                          organism = Dirofilaria immitis
SEQUENCE: 23
tctgttgtaa gtttcacaat ccagttaatt taagctcagc ttatttgaaa ttttcaacaa    60
aattacgaaa attactttct cggttcattt ttttcaacca ccaaatattt agcataattg    120
gcctgaaatc gtcaaagttt acaaactttt gttcagcaat cttctcttac tcttacaata    180
aacatgatta acttgtcgtc ataccaatct cgttatagc aaattctttt caaaaaaaca    240
ttgctacaaa ttttatatcg catcatttca acacgcataa ttatttttca tatatgaaaa    300

SEQ ID NO: 24             moltype = DNA   length = 300
FEATURE                   Location/Qualifiers
source                    1..300
                          mol_type = genomic DNA
                          organism = Dirofilaria immitis
SEQUENCE: 24
ttcacaatcc agttaattta agctcagctt atttgaaatt tcaacaaaa ttacgaaaat    60
tactttctcg gttcattttt ttcaaccacc aaatatttag cataattggc ctgaaatcgt    120
caaagtttaa aacttttat tcagcaatct cctcttactc ttacaataaa catgattaac    180
ttgtcgtcat accaatctcg tttatagcaa attcttttca aaaaacatt gctacaaatt    240
ttatatcgca tcatttcaac acgcataatt ttttttcata tgaaaaac catattataa    300

SEQ ID NO: 25             moltype = DNA   length = 300
FEATURE                   Location/Qualifiers
source                    1..300
                          mol_type = genomic DNA
                          organism = Dirofilaria immitis
SEQUENCE: 25
attaactctg aacccaaaga ctgttggtta aaataaagat ctattttagt tatacatcta    60
acattaaagg ttttcgtacg gaaacaagta ggtttgataa ttttcatgta actgtaaaga    120
acacctgtga aagggatcag taaaatttgg gggatgtagc acggaaatat gaagctgagt    180
gttttgtacc caaaagttt tcaaatctgc gaaataacga gaggtgtaat gatcgttttt    240
aaccaaattt tttgattcta atccttccca cagttttgaa attcagtaag catttctttt    300

SEQ ID NO: 26             moltype = DNA   length = 300
FEATURE                   Location/Qualifiers
source                    1..300
                          mol_type = genomic DNA
                          organism = Dirofilaria immitis
SEQUENCE: 26
ttgcaacaaa tcaataataa aagacttgcg gctaacaata tatttgattc ttttttaccg    60
ttattattat gacaggtaat aatagtatta caagcatatt tgtaggtgtc aatttttca    120
attcaaattt tcttaattca ttatttcttc ctttccttaa taaatagtct ttccatttaa    180
gaattaactt tttgaaatct ttaatgagaa gacacaaaag attccggata attttgcatc    240
atcttttcta tttcgcgtta gtatttttatg ttttcaacag attttttatga tttaactata    300

SEQ ID NO: 27             moltype = DNA   length = 300
FEATURE                   Location/Qualifiers
```

```
source                     1..300
                           mol_type = genomic DNA
                           organism = Dirofilaria immitis
SEQUENCE: 27
gataaaatgg gttcttgtca agctcatttg gcatatcttc gtcttctata tttatatcct    60
ttaatatctt ctcttttttc aaatttttcct tcccgacgtt ttccatatcg acctcttcct   120
tcataaattt atcttcctca tttgcctcat tttttgactt ttcatccgtt tcatccttat   180
ttttctttt ttcatctcct attttacctt ttccttatc aacttctatc ttaacttct    240
caatgttttt tttattttct ttcatctttt tgttttcttc tattgacata ctataacaaa   300

SEQ ID NO: 28              moltype = DNA   length = 300
FEATURE                    Location/Qualifiers
source                     1..300
                           mol_type = genomic DNA
                           organism = Dirofilaria immitis
SEQUENCE: 28
ttttacgaac aattatttca taaaagattc gtatttttga ttagtttta agaattttt    60
tttattattt ttagccaaca aatatatttt tcaaaattgt taaatttgaa attataaatt   120
tcaactaaaa aaaagcaaaa agctaagcca atagaaataa catacatgtg taatataaaa   180
tataaagtat tcgaaatgaa aatcaaagtt tcataacaaa aaacaaaaaa tattctaacc   240
ttttagattt catcaaaact tcactaaaaa gttaaattta aattttcaaa ttgttataca   300

SEQ ID NO: 29              moltype = DNA   length = 300
FEATURE                    Location/Qualifiers
source                     1..300
                           mol_type = genomic DNA
                           organism = Dirofilaria immitis
SEQUENCE: 29
cgaacaatta tttcataaaa gattcgtatt tttgattagt ttttaagaat tttttttat    60
tattttagc caacaaatat attttttcaaa attgttaata ttgaaattat aaatttcaac   120
taaaaaaaag caaaaagcta agccattaga gataacatac atgtgtaata taaaatataa   180
agtattcgaa atgaaaatca aagtttcata acaaaaaaca aaaatattc taacctttta   240
gatttcatca aaacttcact aaaaagttaa atttaaattt tcaaattgtt atacaatgat   300

SEQ ID NO: 30              moltype = DNA   length = 300
FEATURE                    Location/Qualifiers
source                     1..300
                           mol_type = genomic DNA
                           organism = Dirofilaria immitis
SEQUENCE: 30
tcaaagacaa aatgaagaac ttaacaaaaa aaggccaat aaataaaggc tatttcgtga    60
aaaatctaaa aaaaaaaga tctgttcctt tcgaatcaag tgattcttcc tactacattc   120
gtgttgtaat tcttacttgt atacagtccc cagttttcg acgataaaaa acatttcgat   180
aagtgagttt gaattaattg aattttaaaa gatcataaaa ataaaatcaa aataaaaaga   240
ccaaaattaa gtctgataat tccagaaaac acaataataa atatacaaat aataaaaact   300

SEQ ID NO: 31              moltype = DNA   length = 300
FEATURE                    Location/Qualifiers
source                     1..300
                           mol_type = genomic DNA
                           organism = Dirofilaria immitis
SEQUENCE: 31
aaataattca ctaatttctc atcatcaaat tatttcgtac aatcgataaa tcaacgatta    60
taatagcgaa gagaatgaaa attaatgtgg tgcacacgtat acggacccca tatacaatgt   120
tcaacagaga tgaacatttt ttttctatta aagttttctg ttcggcgaaa gaaagacact   180
ttctaacgat gctttcctcc caactcccct tgcaatgata gaggatgcag ccaagattcg   240
tcgactcaag cagcatcact caaccggcca tcacttcggg acctttttcc ctgccttta   300

SEQ ID NO: 32              moltype = DNA   length = 300
FEATURE                    Location/Qualifiers
source                     1..300
                           mol_type = genomic DNA
                           organism = Dirofilaria immitis
SEQUENCE: 32
cattgcgaat gaccgctatg gaatatcaat tagcagatat taatcgtgaa ttaagcacat    60
tggtggaatt tttacgacca aatcgaattt caaaaaatgc tacacttgca acatcagcaa   120
ccattgcaac atataacagt acttcgatgc gtaatgtaaa aaagaaatgt aatgcatctg   180
aaagctgaaa attcatctga tatattgaag caaaaggtaa gattattttt aagatatcat   240
tcttgatgct ctcataattt ctacatcaaa tttaatcaaa cgattcattt atgttcattt   300

SEQ ID NO: 33              moltype = DNA   length = 300
FEATURE                    Location/Qualifiers
source                     1..300
                           mol_type = genomic DNA
                           organism = Dirofilaria immitis
SEQUENCE: 33
ttcttgttgt acctatcata gatgataact taagtaccaa tagcaatagt gcaacgatgc    60
aaggattctg attaatgatt ataaaagttt aaccatctt cttcattcct tctaatcaag   120
agaaaaaaaa atgagaacat ttttatgaca tttgaagaaa ggcaatttat cgctgaaaat   180
```

-continued

```
tctactgcga tatggaagta tcagatagag aaaataaata ttaaaatatg gatttcatac  240
gaaaaatgat aaaagataat aatttacatt ttggtgcttt actgatatga ttggagtatt  300

SEQ ID NO: 34          moltype = DNA  length = 300
FEATURE                Location/Qualifiers
source                 1..300
                       mol_type = genomic DNA
                       organism = Dirofilaria immitis
SEQUENCE: 34
cgatattttt tggacgaatc aaaccttttt gggaaatcat ttgatgtcac aagcatggtt  60
tgagaaattt ttttccgaat tagttctgct aaaaatactc caaatgagtc tagtggaatt  120
aagctaagca ccttaagtaa gttgagaaaa acgtttccat ttgactaaca aggctagtat  180
atcgacatga gacagaaatg gttattactt cactcacttc atgaagcgaa tacgaaatat  240
ctgttcactt tagtttcaat ctactatttt accaataaac gtgttctttt ccggataaat  300

SEQ ID NO: 35          moltype = DNA  length = 300
FEATURE                Location/Qualifiers
source                 1..300
                       mol_type = genomic DNA
                       organism = Dirofilaria immitis
SEQUENCE: 35
tcttaattga ttttcttaac tcgaaacact tgtcttgatt actgtgctgt actttatctt  60
attaaattaa ataatttcca tgaccacttc ataccattga ccatcaaact ttgatgaagt  120
ttatgtgtga agtgccaaac aatcattcat cccttcagtt taacttattg ctggtcaaat  180
tcataaaaat gcaaattatc aagcagatag taattcagtg aacgtagcgt attctcgaaa  240
tttctttcct tgtatttacc ttatatagaa caacgtatat ttgtagcata tattcaatat  300

SEQ ID NO: 36          moltype = DNA  length = 300
FEATURE                Location/Qualifiers
source                 1..300
                       mol_type = genomic DNA
                       organism = Dirofilaria immitis
SEQUENCE: 36
tttctgagtt tgcgttacag cgccaaatct tcacggagat agataaaata cttatcgtga  60
aattttggcg ccatgattta aaaaacacgg agataaaaat aaaatgctta tcggtgataa  120
tttagcgcca taatatgaat gaattgaaaa aacaatttga gtagaaacat gacatagagt  180
tttcgttttc tggctacgaa aatggatgaa tttttctgga atcgaattca gtcaaagaaa  240
taggaacgtt gttactaaat gatcgaaaag ctttctaaaa ttaaatttat gacgtctaag  300

SEQ ID NO: 37          moltype = DNA  length = 300
FEATURE                Location/Qualifiers
source                 1..300
                       mol_type = genomic DNA
                       organism = Dirofilaria immitis
SEQUENCE: 37
atctaaatct tcgttttata gtggtaagac ttccatttgc tgcattcttg caaattaagc  60
tgttgaaaat actttttttt ttgatagatt tccaatttaa tcatattata agaagaatta  120
atttcgaata gaatttttaa atcatttaaa ctttaagttt taaaactaat ataagttatg  180
cagatttcgc gaaaaagtct catttgttaa ttcaattatt ccaaaatgta ataattttat  240
aaattcaaat ttaaactact actaacttct gaagtcagga gccagtagca acaacgtaat  300

SEQ ID NO: 38          moltype = DNA  length = 300
FEATURE                Location/Qualifiers
source                 1..300
                       mol_type = genomic DNA
                       organism = Dirofilaria immitis
SEQUENCE: 38
aactttacat ttatattcaa ttttttttta ttttgtttgt ttttagaaat ttgaaaatgg  60
gtactaatca gtgtcatttg cagcctctta gaccctcttt ataacgaccg attcgatgaa  120
atacgtcatc aatatgccag tttattgttc gggtggagaa tgttttcaaa agttgctgaa  180
gtgatgaagt atagtgagaa tgcaccttat tcagcaccat taagaagtaa atttttgctt  240
tggaatttga caaagacaaa gcaggaagtt gacaacgatg ttctgatgaa acggtttcga  300

SEQ ID NO: 39          moltype = DNA  length = 300
FEATURE                Location/Qualifiers
source                 1..300
                       mol_type = genomic DNA
                       organism = Dirofilaria immitis
SEQUENCE: 39
gtctattttg gctgtcttct aataattcat tttgtaacct tttgaaatat gataaatgta  60
gaaatttttt cttcctggtc tataatagtt taataatgtg ttgtagtaat agttttggtg  120
ccgttgaaat atttcaatga tatgctatcg caaaattagg aattcaaatc aaggttacaa  180
gataattcaa aaacaaacaa cgtaaaaatg aaataatttc ttcttcttac ttaccaacag  240
gcatatcatc atcatcctca aattcatgac tatatttaac attgtcatat ttgaataatc  300

SEQ ID NO: 40          moltype = DNA  length = 300
FEATURE                Location/Qualifiers
source                 1..300
                       mol_type = genomic DNA
```

```
                        organism = Dirofilaria immitis
SEQUENCE: 40
cgacgcaaaa atctttcaaa ttgtcaccca gttctctaag tgattccaat gatgttggta    60
aacattctgc atgatgtacc gggtaatgaa ctaccaagtt gttttttgct tttaatacaa   120
ctcgcaaaga ttctgaaaac catgaaatta agaaagatta aaataatctg aactcttttt   180
ttcattttc  cttgaactta gcaatatact gagttggata aaatttagaa acgaaatttc   240
gcaaatttat tcagtaaatt caggaaaact cggtttcggt attctaaata taaatagata   300

SEQ ID NO: 41           moltype = DNA  length = 300
FEATURE                 Location/Qualifiers
source                  1..300
                        mol_type = genomic DNA
                        organism = Dirofilaria immitis
SEQUENCE: 41
gtttctttgg tttatctcag taagatttgg gcggaaattt cagttatact tttcatttcc    60
atgtgctgtt ttaaatttct tccatattag tataattttc aaataattgt agcgtcactg   120
gtttatttaa ggataacagg ttggactgca gtggctgaga agtgtcttgc cggtcaattg   180
tttgttggtg atcaacttgt acgagttact gatatcgaca tatataatac acggcaaatt   240
ccattcgttt tcagtactgc atcaaaaacg ggattatcgg tactttgtaa atcgcagtat   300

SEQ ID NO: 42           moltype = DNA  length = 300
FEATURE                 Location/Qualifiers
source                  1..300
                        mol_type = genomic DNA
                        organism = Dirofilaria immitis
SEQUENCE: 42
gaccctgct  cacaaggcag ttcccacaga caatcacaca tctaatcaca cacatcaact    60
catccgacgt aggctatcaa taaggaaaat tgcattgctt tatcgtctaa ctgtaataaa   120
catctacata atgaaattat ttcgccacta tgacaactaa tatcgcccaa tgcaaatatt   180
tgtctcagag ttattccctt taacagctg  ttgaacgaat agataggacg tcatgtggat   240
gatctacttg tttcaaaggt tgaggtaaca catgaaaacac atgaaaacgg taatttaaaa   300

SEQ ID NO: 43           moltype = DNA  length = 300
FEATURE                 Location/Qualifiers
source                  1..300
                        mol_type = genomic DNA
                        organism = Dirofilaria immitis
SEQUENCE: 43
aaagaatggt cagcaagatg tggaaaatcg attactatag ttgaagtatg aatcgaagag    60
gtttttttaa attctaagag aacgaataat cggcaaagag aaagttgagt aaccttattt   120
tgccttgttt tcagtcaatt tataatatgc ggttaattgt gttaaagaaa gtacaaggta   180
tgaaatctaa gccaagaaat aagagaaaac agctaatgat tatttctgca ttttttcttt   240
ttcgacacaa acttggaacc agaatcaatt gaactagtaa tcagattttg attattgctt   300

SEQ ID NO: 44           moltype = DNA  length = 300
FEATURE                 Location/Qualifiers
source                  1..300
                        mol_type = genomic DNA
                        organism = Dirofilaria immitis
SEQUENCE: 44
ttagattttg ctgaagcatt gttggttaga tcgatgaaaa tataattatg agagattttg    60
ttgaaattca gcaacaaaat tattattcat gtcttcatgc tgtcagtttt gttttattt   120
cttctttgac atcggttata ttttgtctt  ccaacaatat aaaaaaaaaa ttataatcaa   180
ttggtaatca aattaaaact ctaattgtta gctccctaaa tcagctttaa aaaaataatt   240
gcttaattgg tatttgctac tattagcaaa ctgaaactat ccttttctcg aatggtgaac   300

SEQ ID NO: 45           moltype = DNA  length = 300
FEATURE                 Location/Qualifiers
source                  1..300
                        mol_type = genomic DNA
                        organism = Dirofilaria immitis
SEQUENCE: 45
atgagctgat atttgatatg catattaaaa atagggtaaa ttacattaag ttagatatcg    60
ttcggataaa ttaattagaa aaaatgttta ccaattagat cgcaatgatg taaaatttca   120
cgtattttta ttcttaagat ttatttgcaa aattcaaaaa tatgtcttat gaaaaataat   180
atttctgtgt aagaacaagg gaccgattca cttgatttat tcgcaaacaa tcgaaattca   240
aaattagtaa ttttaaatat tgctttattc aaaccatacc aataataatt tgagagattt   300

SEQ ID NO: 46           moltype = DNA  length = 300
FEATURE                 Location/Qualifiers
source                  1..300
                        mol_type = genomic DNA
                        organism = Dirofilaria immitis
SEQUENCE: 46
attgattgat tcaaataaga aatttaaatt atttcccctt ttttcaaaa  gatttaacaa    60
atattattta tttgatctcc tcgttcgttc ttatctttt  gattatcaat ccatcctcct   120
ccatcatata gctaatttat ttttgcatc  gtaaatcaat tgatgtatga ttgatttctt   180
gattataaaa agttagaaga attgaattgc ttaaatttaa ttattgataa tgaaattatta   240
ttatatttca aaatgatacg aagaaatatg acgatgataa gagaaaatat gatattttatc   300
```

```
SEQ ID NO: 47          moltype = DNA  length = 300
FEATURE                Location/Qualifiers
source                 1..300
                       mol_type = genomic DNA
                       organism = Dirofilaria immitis
SEQUENCE: 47
tacgataagt tattttattt tacacatctc catccttgac tagtgtccgt gccgactgtc  60
ggacttgaac cgacaaccta ctaattacaa gtcagttgct ctacccaatt gagctaagcc  120
ggccatctag aatgtgcgac cccgtcgtgg tacatcttct ataatcgttt ggtattcagg  180
actctcttct ttcgtgggtg gaggatcttg atacagttga ctattaaaaa tagggccttt  240
gttagtctgt tacaactcat agacaaaggc gacaatttta gcttacatct tacgttatgc  300

SEQ ID NO: 48          moltype = DNA  length = 300
FEATURE                Location/Qualifiers
source                 1..300
                       mol_type = genomic DNA
                       organism = Dirofilaria immitis
SEQUENCE: 48
atggtagaaa attatatgaa aaaatatcat actaaaaata taacagattg ttataaggta  60
tggtttaaga atttacaaca attgattatt tatgataaaa aaaaaaaaag taaatcagtg  120
aatcattaag atagttatga taagcagttt gtattcggta aagcgaatga ttagaggaat  180
tatgggacga aacgtctata acctattctc aaacttttaa tgagtatgac gtgtcttgct  240
tgcttaaaat tatttcaatg atcatttcac tttaccagta tgatcatgat tagacttgaa  300

SEQ ID NO: 49          moltype = DNA  length = 300
FEATURE                Location/Qualifiers
source                 1..300
                       mol_type = genomic DNA
                       organism = Dirofilaria immitis
SEQUENCE: 49
ttagtatcga tattatcaca aatgatatca ctttcatcaa tactggatac gattttatta  60
gtatcataat tttgtggctc gcattccgaa agttttacac gtagaagatt aacctgcaat  120
atgatttatt ttatcatttt cgaatatcca actttgaaat aattcgaaaa tgttgaaaaa  180
ttttgaaaaa ttgttaacaa aatattacaa aaatatcaaa tgaaattaaa taactgtcca  240
tttcaaaaaa agaagaaaaa ttatgaaatt accaattaaa aacaggactt attaattaaa  300

SEQ ID NO: 50          moltype = DNA  length = 300
FEATURE                Location/Qualifiers
source                 1..300
                       mol_type = genomic DNA
                       organism = Dirofilaria immitis
SEQUENCE: 50
tgtggaaata aagtacaatt aattgctgtt cgcttaataa tattattttc attcttggct  60
tttttttct ttccccgtga tattataaaa tatagttttt taattttaac aaatcgtcat  120
aattatttaa aaaatactga ggtgagtaaa tgtaattggt tgctggaaaa aaagtgggtg  180
atgagaggtg aatgaaagca gaatagttta tgattgcatc aaatttcctc cttaatctgt  240
gattaaaatc aaacaaaacc cgaaaagttt cttcttcgcc tttttcttct ctttgtttca  300

SEQ ID NO: 51          moltype = DNA  length = 300
FEATURE                Location/Qualifiers
source                 1..300
                       mol_type = genomic DNA
                       organism = Dirofilaria immitis
SEQUENCE: 51
cgaaatccgc cgcgtgcatt actttgcgct tgttgattac gacgcatttg ttcgtcgttg  60
ataaccttat caatcatcat acgtccgtta cgtatgcaat caacatcgcc agttaggctg  120
aaatcaaatg gatggcgatg atatcaaaaa caaaaataag gagtatttgc tgaatcattt  180
ctttttctgt attattatca aaattttctc ctttccattg tttccttctt aatcaagtga  240
atgctcattt cattttgaaa taatccaacg taataattcc ccatattccc aattactttc  300

SEQ ID NO: 52          moltype = DNA  length = 300
FEATURE                Location/Qualifiers
source                 1..300
                       mol_type = genomic DNA
                       organism = Dirofilaria immitis
SEQUENCE: 52
agaaatatta aactttgaaa agatgtgaca tgttctgtaa caaaagccca aaatttcgac  60
tgctgcggct tgaagtaaaa ttttggaata tgctacatca gtagtgcaac agatggttcg  120
ataaatagtg gtaagtgatg ggaatcctag gaatagatgg gaattgtatt tcagatataa  180
atttgatgca tattttcata gttgattata tctacgatca cacgttgaat attctaaaag  240
caaactgtaa ttaactaatt gaatttgaaa atttccaaga attaaaattg gtaacaaaaa  300

SEQ ID NO: 53          moltype = DNA  length = 300
FEATURE                Location/Qualifiers
source                 1..300
                       mol_type = genomic DNA
                       organism = Dirofilaria immitis
SEQUENCE: 53
```

```
attgtcagga atgagaagca agttttggat acttaaggga tgaatggaac acatacatgg    60
cagaaaatgt tagtaatcaa accatttaaa ttacttagcc actatgctaa actttctaga   120
agtatggttg aacgtttaaa aaccttcgca aaaattgtat tagattatct taatcttccc   180
tacatcaaaa cagagaattt ttgttctacg acgtgagtct gcatgtatta aggaagttcg   240
tatcatgacg taaatatcct gagtgattat tgaattcaga aaatgagctt tttcatttgg   300

SEQ ID NO: 54          moltype = DNA   length = 300
FEATURE                Location/Qualifiers
source                 1..300
                       mol_type = genomic DNA
                       organism = Dirofilaria immitis
SEQUENCE: 54
atatgagtgt tacatgtgta cgttacatgt aaatattata tgttatatgt aaaaatgtca    60
tgtatagcat ctattcacgt gtacgtacac gtgtatatac atatacattg atacttaata   120
cgtatacgca tgaatgaaca gatattatat atttacgtac actagactca catgtacctc   180
tgtatacgca tacatgtaca gatatatgtt tgacatacgt aaattcatat atgcttttat   240
ttatgcttat attaattgtc acatacatgc cttatatttt cgttgttata aacacataaa   300

SEQ ID NO: 55          moltype = DNA   length = 300
FEATURE                Location/Qualifiers
source                 1..300
                       mol_type = genomic DNA
                       organism = Dirofilaria immitis
SEQUENCE: 55
gaaaataaaa ttagctgaaa atatatgcga ggtaaagcac acagaagaat taacttaagg    60
taatatattg taagaatttt tatattcggc gcacctaata attttttagac cgcatatgcc   120
cagtatttga aactggtagc gctgttcgta cttgctgttg tccatgttat gtatatgata   180
ccattcctaa atacttttgc ggctgtggtt tccagtgttg atgtgactgg tatgatgcct   240
aacactggat ccttccatct gcggcatttt gttgaaattc ttattgatgt gagctgttta   300

SEQ ID NO: 56          moltype = DNA   length = 300
FEATURE                Location/Qualifiers
source                 1..300
                       mol_type = genomic DNA
                       organism = Dirofilaria immitis
SEQUENCE: 56
caactgtgaa tcataaacat tacttaaatt aatgaagcta gttaacgaca aatatatttt    60
tttatgtatc agtgctatca tataacataa aaacttactt tcattaataa atgagctcaa   120
atattgactt ttgtccaaaa tgctcaaaat gtcgtcataa tatttgaaat gaagatatt   180
tcacgctttt cgaagcctcc tctcacgtct tttaatcttc ttttcttctt cttgctctaa   240
tggttctgcg aaaaaccacg gtgcaataat cactttccat aatttataca gtacataagc   300

SEQ ID NO: 57          moltype = DNA   length = 300
FEATURE                Location/Qualifiers
source                 1..300
                       mol_type = genomic DNA
                       organism = Dirofilaria immitis
SEQUENCE: 57
ctgcttaact cttttcattt ttcagagaat cttctctaaa attgtgaatt gatccaaacc    60
aaagaatatg gataatgtga ttcgaattcc tggaatttag attttgagag ttttgaagtt   120
tttaaagaga ttgaatttct gtgaccttct ggtatatttg atgtcatttc gggatgcgta   180
ttttgccga aaattttggg cctcactgca atcttgttaa aagtcaaaaa aattcaatcg   240
tagaatttcg ggtttacctg atattactgg aaatctctga tctttgttct agattgctgt   300

SEQ ID NO: 58          moltype = DNA   length = 285
FEATURE                Location/Qualifiers
source                 1..285
                       mol_type = genomic DNA
                       organism = Dirofilaria immitis
SEQUENCE: 58
ataaagaatt tgcaactctg tatacctttt tgcagtgcaa aagcggatga attcttcact    60
gcagtgtgac agattccttt gataaaattg cttcgttctt atgtaaactt ggaaattctc   120
ggtagttatg cttttgctag ttgaaaatgt tctgctcttg taaaacatgc aaaaagagat   180
tatctttgtt ctattatgga aagattcttt tgaaattttg acgactgaga agacaaattt   240
tatcccaact tgtcatctgc aataaaaatt tttcctgacc tgttt                   285

SEQ ID NO: 59          moltype = DNA   length = 300
FEATURE                Location/Qualifiers
source                 1..300
                       mol_type = genomic DNA
                       organism = Dirofilaria immitis
SEQUENCE: 59
aaaatcaaat caatgatc agataactca tacttatctt actgaaaatt cctcattcaa    60
gggaaataaa taattgcaat tcttgattcc gatcatggat gattttcaag caaattacca   120
atgatatcta tcgataacga ttacagcata cagctataac ttattattga ttgaattgat   180
gaaaataatt ttaccagaaa tttatcaatg tttatctcat tgcagatatac gatgtttagt   240
gtgacaaaac tttttcttgg aataattgtg cataaatcat tgattgcatt tagtattgga   300

SEQ ID NO: 60          moltype = DNA   length = 300
```

| FEATURE | Location/Qualifiers |
|---|---|
| source | 1..300<br>mol_type = genomic DNA<br>organism = Dirofilaria immitis |

SEQUENCE: 60
```
tcctgcccac attctttcta ctttagataa tcaacaggag ttagttgaaa gagaagacta   60
ggaacagttg caacttctga atctttctga ctttctttcg ttttgtaaat tatttatttg  120
tataaattta aaattcgaag agaaataatc caaggtccaa cttctttttc tgttagttct  180
tgcgaatgct ccatcaaaat gcaaaaatat gattagaatt ctgatggaaa ttaacaaaat  240
cgattagata agaaaagtac aaaacagaaa ctaacttttt ctcccatttt catattatag  300
```

| SEQ ID NO: 61 | moltype = DNA length = 300 |
|---|---|
| FEATURE | Location/Qualifiers |
| source | 1..300<br>mol_type = genomic DNA<br>organism = Dirofilaria immitis |

SEQUENCE: 61
```
tcattgcttt aatacttttt aacgagaatt ttctcgatca aaataagatc tgcaattgat   60
atacgtcaat aagcgaacat tagctgtatt acacgctaat attcacatat gatgaacgtt  120
gtaagcgtca tacatcaaca tatatccatc cgataaataa tgaccactac acattgctac  180
caaccatcct atcccgccac tatttgaaat gaactgagaa ggagttatcg acacaggctt  240
cctagcaacc aaacaaaaga cgagacagat gaatagatag acagacagac gaacatacaa  300
```

| SEQ ID NO: 62 | moltype = DNA length = 300 |
|---|---|
| FEATURE | Location/Qualifiers |
| source | 1..300<br>mol_type = genomic DNA<br>organism = Dirofilaria immitis |

SEQUENCE: 62
```
agattctggt tattattgta tttctgattt atttaatccc aacttaaaga ttcattggct   60
attgtttagc atctatatca attttataaa taaatagtaa tacctgatga aaagcaataa  120
ataattagat gcaaatttta attagataca gtttgatgga aaacattgaa gccatgtaca  180
actaatttat gcatgttgaa ttatgcatgc ataattaatt tatgcatgac agcaagtttg  240
gtataaaatt aatttttgtat gaagataaaa tttataaat aatgataata atgctggtaa  300
```

| SEQ ID NO: 63 | moltype = DNA length = 300 |
|---|---|
| FEATURE | Location/Qualifiers |
| source | 1..300<br>mol_type = genomic DNA<br>organism = Dirofilaria immitis |

SEQUENCE: 63
```
attattgaaa agaataatgt agctaattag ttgaagctgt taaaagtaaa gctaaaaaga   60
tgatgaaat tattcgtata aacattcttt gtaaacaaac agtcatttct gtgaataaac  120
aattataatt ataaacaata cttttcaaga caataaaaaa attaggaagc attgttgtga  180
taatcaatag ttgatagact gtcaatgtat ttttatcagt cgtgctgctt tttttccctt  240
tcttgactca tttattttat tatttattga tagaatgtca atattctagt catttgttat  300
```

| SEQ ID NO: 64 | moltype = DNA length = 300 |
|---|---|
| FEATURE | Location/Qualifiers |
| source | 1..300<br>mol_type = genomic DNA<br>organism = Dirofilaria immitis |

SEQUENCE: 64
```
atcttaactt gctttaaaca aataaattaa aacagcccaa tgttccaaga aaaaagata   60
agttaaaagt ggggtgtcca aaaatttatg aattgaattg gacagttatt cagatcctga  120
aaatacgctt ctctgatcac tgcaaatatt cccgataaat aagtgaacat taggttaatc  180
ttaattttcc cttaactttc cttagccttt tttaaatttt tggattattc aagcattttt  240
attgcggtat cgtttttgta aaaaaaaag tataattcaa cattcaggct cgacgttatg  300
```

| SEQ ID NO: 65 | moltype = DNA length = 300 |
|---|---|
| FEATURE | Location/Qualifiers |
| source | 1..300<br>mol_type = genomic DNA<br>organism = Dirofilaria immitis |

SEQUENCE: 65
```
aattaataaa aagaaaggaa tacgataaaa tatctatttt ttgaaactaa tcaaacatat   60
tcctcactgc tcaccggata gttgctttct aattttacat taagaaatat atttttttt  120
ttcaataagg aaagttatgc agactaggag aattctactc tgaagaagag ataagcatgt  180
tagaattatt aaaatctatg gaaatatcct taaagaatg cctatagtag ctctgatttc  240
gaaaaaaaaa gcaaaaaaca aaataacaaa ttctgctcaa ttgaaataaa aactttcct  300
```

| SEQ ID NO: 66 | moltype = DNA length = 300 |
|---|---|
| FEATURE | Location/Qualifiers |
| source | 1..300<br>mol_type = genomic DNA<br>organism = Dirofilaria immitis |

SEQUENCE: 66
```
taaaatatct attttttgaa actaatcaaa catattcctc actgctcacc ggatagttgc   60
tttctaattt tacattaaga aatatatttt tttttttcaa taaggaaagt tatgcagact  120
```

```
aggagcattc tactctgaag aagagataag tatgttagaa ttattaaaat ctatggaaat    180
atccttaaaa gaatgcctat agtagctctg atttcgaaaa aaaaagcaaa aaacaaaata    240
acaaattctg ctcaattgaa ataaaaaact ttccttcaac ttccagcatc actgctgtga    300

SEQ ID NO: 67           moltype = DNA   length = 300
FEATURE                 Location/Qualifiers
source                  1..300
                        mol_type = genomic DNA
                        organism = Dirofilaria immitis
SEQUENCE: 67
aactgctaaa aaattgaaac tagtgttaga ttgataagtg ggcagattaa aaccaattgt    60
gttattggcc cgttaattag tgactctgaa tagctatggc gaatcgtata gtgttgtacc    120
gacgacgtat ctatcaaatg tctgccttgt taaatttcga tgatagttta tgtgcctatt    180
atagttgtaa cgagtaacgg agaataaggt ttcgactccg gagagggagc ctgagttgcc    240
acattcaagg aaggaagcag tcgcgaagat tacccactct tagaatgagg aaagagtgac    300

SEQ ID NO: 68           moltype = DNA   length = 300
FEATURE                 Location/Qualifiers
source                  1..300
                        mol_type = genomic DNA
                        organism = Dirofilaria immitis
SEQUENCE: 68
gaaaactaag aagtaagtga aatttctaag ttctttccca gaaaggttag atccaatatt    60
tgttttcatt ttagcatttt tatccaatga aaaatgtgcc caataaatac ttgtatatag    120
tattgcattt aaaaacttca gaaagcacaa tgagatctaa gctcagaaat atgacgaata    180
ccaatccttt tcctagtctt accgcttctt aacttttgtg tcgctttata aaaattaaaa    240
ataaaaagtt gaacaatggg aattacatca ttttcatctg aatggtttat ttcctattct    300

SEQ ID NO: 69           moltype = DNA   length = 300
FEATURE                 Location/Qualifiers
source                  1..300
                        mol_type = genomic DNA
                        organism = Dirofilaria immitis
SEQUENCE: 69
cttccctagc tatgcctttt cgtcacttaa gcttcnnnnn nnnnntctag ctacgtatcg    60
ttatcattta tgcttcttta gctacgtttc tccatcattt atgcttccta agctacgtat    120
cttcatcact tacgcttccc tagctatgtc ctttcgtcac ttaagcttct ttggctgcgt    180
gtcttcatca ttaatcttct ttagctacgt atcgttatca tttacgcttc cttagctacg    240
tctttccatc atttatgctt cccaagctac gtattttcat catttatgct tccttagata    300

SEQ ID NO: 70           moltype = DNA   length = 300
FEATURE                 Location/Qualifiers
source                  1..300
                        mol_type = genomic DNA
                        organism = Dirofilaria immitis
SEQUENCE: 70
gatcttaaaa ttctatgaaa cttcttctgc atggtattgt ttccaacaga atataatgac    60
aatagcaaca gtattggtta tataaaaata ttgactgcag caggattata ttcaagttc    120
ttttaatttc atttatttat tctttcattt acttttactg ttttatgtt ttcttcttt    180
aaaaaatatg atttctctca ctgttctctt tcatctatct atatttattt gataattgct    240
tatatgataa ctagctaaag ggaaataaac tttcagtcat catagcttca ttttagtaaa    300

SEQ ID NO: 71           moltype = DNA   length = 300
FEATURE                 Location/Qualifiers
source                  1..300
                        mol_type = genomic DNA
                        organism = Dirofilaria immitis
SEQUENCE: 71
ctatactaat cagtccacta tccatttta ggttgcaaaa gttgcaatga cggtttgatt    60
tcatcctcca atgcaatttt gagtctcaat ctcgagagat agatcgatcg cttttagctt    120
gatttagctt ggtaatgtt gtgagggata ttgggcagaa attctgtcaa gcgttactta    180
atgaaatagt aaatgatcac tgatatttat tgttaatgat acttgagctc tctagattat    240
gaactggaag gttttcgata gaaataatcg atacatatat tagaatcgac ttctttttc    300

SEQ ID NO: 72           moltype = DNA   length = 300
FEATURE                 Location/Qualifiers
source                  1..300
                        mol_type = genomic DNA
                        organism = Dirofilaria immitis
SEQUENCE: 72
tcatcttttt cacatttcat ttaatcatca tttatcaat tcctattttt aaacaaattc    60
ttttcaaata ttctctcttt ccttctcttt tgttttccg cttattcatt ctaatgatga    120
acagatgtag aaaatttgca ttctattgct cactacaatt ttgagtagaa tatatttaat    180
tatttgattc gagacagatg gttatagcct ttagcttcag cttcgttc aaattaagta    240
cttgtgacct ttccaagtac cattaaagct ttcctgcgtt tcctaattag aaaaaaaagg    300

SEQ ID NO: 73           moltype = DNA   length = 300
FEATURE                 Location/Qualifiers
source                  1..300
```

```
                                mol_type = genomic DNA
                                organism = Dirofilaria immitis
SEQUENCE: 73
gcattttaag ttaaaagtat cacgctgcat gacacctcac gtttgctatc tcaaattgag      60
taggttagaa tcttttttg  gctactattc aaatattaat aataaattgc tgcaaacaga     120
tttcacaccg gaaaaaaatt aaattttct  agcaatgttt taactcccctt attaaatatt    180
tatagaaaat cgactactta aaaagaattg actaacattt ctgaatctct gcagagattt     240
atagatggat tagcatccta caagttttta tcttttgct  atatttccat tattttttta    300

SEQ ID NO: 74                   moltype = DNA   length = 300
FEATURE                         Location/Qualifiers
source                          1..300
                                mol_type = genomic DNA
                                organism = Dirofilaria immitis
SEQUENCE: 74
gataagacgt cttatttgt  aataattcaa aaattaatta atatagaagt aagatcttga      60
taataattaa tatgctcaaa tttcttaatg agaatatgtt caggatgaag atgaagtgaa     120
agaaattgat agattgagga agcaattgct aattgaaaca gaacagctcg tttccaattc     180
tcttaaagat ttactgaaga aaatttatta tccacttgaa gaagctattg atctcaaaat     240
tcatcagaaa ttaattcaac aaattgctgc cttgttgaag tgtattagta tcttggataa     300

SEQ ID NO: 75                   moltype = DNA   length = 300
FEATURE                         Location/Qualifiers
source                          1..300
                                mol_type = genomic DNA
                                organism = Dirofilaria immitis
SEQUENCE: 75
accgcaaaat acctaaaaat ttctataaca acgattaaca cggcctcgaa ctggaagcat      60
attaatccat gcgtggctca aacttcaatc ataaagacaa gatctagaga tcaacacaaa    120
atggtgaatt gttaccctat cgttgctaaa gtttgagaga aaaaagtgct aaatcaagta    180
gtacaccaaa tttagttaat attaagaaat caatttagta ctgaatttaa acaaatgaaa    240
ttttacgata aaataaaaaa gtacctgatc aaacagcgtc ctcccgttat tcccattgct    300

SEQ ID NO: 76                   moltype = DNA   length = 300
FEATURE                         Location/Qualifiers
source                          1..300
                                mol_type = genomic DNA
                                organism = Dirofilaria immitis
SEQUENCE: 76
tataagacta gtaaacagat cgtaatataa taaatatcga ttttatttta aattttcgaa      60
aacttccaaa tctatcgata tgaaattaaa gatcaatttt taattccat  aatatattta    120
gattctatcc caacatcact catctttatg tcaacttatt taattctctt attaacatta    180
tatttcttgt ttacaatgat aaattttatc aattttctaa tatgatagaa catcttcatc    240
atctgaagat atgcttttct catctttgta acaattcgta tcgcttctga ttttactttc    300

SEQ ID NO: 77                   moltype = DNA   length = 300
FEATURE                         Location/Qualifiers
source                          1..300
                                mol_type = genomic DNA
                                organism = Dirofilaria immitis
SEQUENCE: 77
gttttattat tgcttattga atagtgataa taacactttg atatgatatt gttttgttgc      60
gatcattgta ttgattataa ccttaattaa acgaggatat tatgggaaat gtatttatta    120
caaaattaaa tatgaaaggt tgaagtcttg acgaaacttt caaacacatt tctcgaattt    180
tctctgcaaa aatatcgtta cgattttgg  aaaatatgaa gtccaagaat tcaatcgaga    240
gttcgccatg tcactttggc tagtttcgtt tgttttaat  atttcaatca aagtcaatt     300

SEQ ID NO: 78                   moltype = DNA   length = 300
FEATURE                         Location/Qualifiers
source                          1..300
                                mol_type = genomic DNA
                                organism = Dirofilaria immitis
SEQUENCE: 78
ccttggatat tgttcttgac atcgttgatc agaaggtcac cgtagtgttc ggtgagcgag      60
atggaattgg actcaggttt attctccgtt tttttcatgt ttttgaattt tagagagaaa    120
ataatgtttg tctgaatggt tagcaaacta attagttttt aagttatcag gaactcgaag    180
tatcttcttt tgcacttctt taacctttt  catcaaattt tttaacagta acaagatttt    240
tttgagaatt ttcaaaatat ttttgacttc tgatgatatt tgatgagaaa accatcactg    300

SEQ ID NO: 79                   moltype = DNA   length = 300
FEATURE                         Location/Qualifiers
source                          1..300
                                mol_type = genomic DNA
                                organism = Dirofilaria immitis
SEQUENCE: 79
agagtattat tatacatgat gatgatgatg atgatgatga tgatgatgat gatgatatga      60
tgatgatgat gatgatgatg atatgatgat gatgatgata atgataatga tgatgatgat    120
gattaattgc ttattttaa  tgattgataa ctttaaaaga aatcattgaa atttgatcga    180
ataaaaattt tctaaaaaaa agcatttgct atttatatag taaacctata aaaaattact    240
``` tattttttatt actaatattc atttgattgt atgaaagaga agagaaaaaa aacctttgca 300

SEQ ID NO: 80            moltype = DNA   length = 300
FEATURE                  Location/Qualifiers
source                   1..300
                         mol_type = genomic DNA
                         organism = Dirofilaria immitis
SEQUENCE: 80
tggtatcaca gcactgggtt taatttcaac aatcggttga cgatcttttc gggatatgcc 60
tatacccaga aatgaacgta tgccaaacga tggtatgttt gatgcaacag acgacgtcaa 120
cttaaaatgt gtttttttt caaaaattca atatttttag tttaaaattg cacgtcagta 180
aaaattaatt cataataaat ctctttgatt tcttcgttct cctttttttt cagaaaaaat 240
tgaaatttta catacctgat ttccaagagc atataaagca tcacttaaag cattctgcga 300

SEQ ID NO: 81            moltype = DNA   length = 300
FEATURE                  Location/Qualifiers
source                   1..300
                         mol_type = genomic DNA
                         organism = Dirofilaria immitis
SEQUENCE: 81
tccttttcat gatttgtagc taaccaataa gatgtgtata tgttcatata tttactctcc 60
cctgactctt ttacactctc attctctcat ttgttcattt agataagtaa tatgcgcctt 120
tctcttcctg attctctcaa tctttcatcc cttcatctcc tcaatctttc tcccattctc 180
tcaatctttc ctgcattgca ttcattgatg aaacacgata gtattaataa gcataatttg 240
ataaattgaa ataatttttt ttnnnnnnnn nntcattctc tcaatctttc ctgcattgca 300

SEQ ID NO: 82            moltype = DNA   length = 300
FEATURE                  Location/Qualifiers
source                   1..300
                         mol_type = genomic DNA
                         organism = Dirofilaria immitis
SEQUENCE: 82
tttgaattaa caaatatta acaattacaa ctatttcgga atttaattta agaataattt 60
aattaatcaa tttcctattt tgtattttaa aaattaccac aataattgtg taattttgag 120
gatatttgaa actttgaaaa aagtggtatt gtatttgaga ataaattaat taatgtaatt 180
cttgctgctc atcgttccat aacttacaaa tatttctcgg tatttattt gagataattc 240
ttatcatttc ttccatagct ttcaatatat ttataactta tttgtaatca ctcttatcac 300

SEQ ID NO: 83            moltype = DNA   length = 300
FEATURE                  Location/Qualifiers
source                   1..300
                         mol_type = genomic DNA
                         organism = Dirofilaria immitis
SEQUENCE: 83
ttgagatatc aaatcaagcg ttgcatattt atagtacact ggtgtagctg aaatcgcgaa 60
gagaacacga aaatcagaga agtcaatggt tcctttgtgt tggatttcac atgaaagcat 120
cctatgttg tacatgcgtg attacaatat gatacaagat gtaagctaaa aattgtttta 180
tctttgtcta tgagatgtag ttcatactct ataataaagt cccaacccct aattctcata 240
ttcacaaccg tatcagaatc caacaccaaa ccattataaa gaatgttctt cgtcgaggcg 300

SEQ ID NO: 84            moltype = DNA   length = 300
FEATURE                  Location/Qualifiers
source                   1..300
                         mol_type = genomic DNA
                         organism = Dirofilaria immitis
SEQUENCE: 84
ccactatcgc ttcacttttc tttatcctgt tcttcttcat ctttcgtttt ggactttatt 60
ttactgtcag gtgacaagca aagtaacgat gttggacttt gcgaagatgt ggatggtacg 120
ctagaaaaaa aatgaggatt ggttaatatg tctaattatt acatcgcttt tttttaaatc 180
ttttctaaaa ttaaactgaa taatcaactt atttgctatt cagtttatct tatttttat 240
caacaaaatt cgaggaaaca aatcgcttat cagaataatt gttttgatca acaaataaag 300

SEQ ID NO: 85            moltype = DNA   length = 300
FEATURE                  Location/Qualifiers
source                   1..300
                         mol_type = genomic DNA
                         organism = Dirofilaria immitis
SEQUENCE: 85
caatcccaca aattcagtgt gtcggcgggt cagcgaaggg aaagtttgaa ccgagggtat 60
gtacaaattg tgataatttt gtgatgacgt agtaaatttc atagtttttgc atgcttaat 120
gttgatagtc gcacaatcct acgttgatta aatttagcta ttagatatcc tactaaatta 180
tgttgttcat aattttttgtt tttaaaatgc tccacttata ttttcaggtt gtgcagtgct 240
acaataggg ttatgacggc aatgatgtcc aatgggagtg taaagcggaa atgagcaatc 300

SEQ ID NO: 86            moltype = DNA   length = 300
FEATURE                  Location/Qualifiers
source                   1..300
                         mol_type = genomic DNA
                         organism = Dirofilaria immitis

```
SEQUENCE: 86
tcagataaat tgtatttgat gttaattcaa agaagaaaaa aataatcagt agaatatgaa    60
tcgaataata ttcatacaac cagtttattc attattattc acttttaacg tctaaatgac   120
gtagctacgc ttttttctc gctttcaagc ctttactgac caagattaat gtacattctg   180
ttgaacaaga ttaatcgaca ttctatcgat caagatcaag cttttactga tcaagattaa   240
taatgacatt cttctgttga tcaagattaa tcgacattcc attgatcaag attaatcgac   300

SEQ ID NO: 87           moltype = DNA   length = 300
FEATURE                 Location/Qualifiers
source                  1..300
                        mol_type = genomic DNA
                        organism = Dirofilaria immitis
SEQUENCE: 87
ctctctaaaa cctattggtc actaaacttg cactgactaa aaactattgg tcatcagact    60
tgtgattcat tgaaaagacc gttagccgct aaaattatga ttcactaaaa aaaatctatt   120
gatcattaaa tctgtaatca ttgagaaact acaatcattg gtcattaagt ttgtgctctc   180
taaaacctat tggtcattaa actgactaaa aactattggt cactgaacct agagtctatt   240
aaaaaaaaaa tcattgtatc aataaattta tgttttacta tcaaatccat tgattactga   300

SEQ ID NO: 88           moltype = DNA   length = 300
FEATURE                 Location/Qualifiers
source                  1..300
                        mol_type = genomic DNA
                        organism = Dirofilaria immitis
SEQUENCE: 88
tctaaaacct attggtcact aaacttgcac tgactaaaaa ctattggtca tcagacttgt    60
gattcattga aaagaccgtt agccgctaaa attgattc actaaaaaaa atctattgat   120
cattaaatct gtaatcattg agaaactgca ttcattggtc attaagtttg tgctctctaa   180
aacctattgg tcattaaact gactaaaaac tattggtcac tgaacctaga gtctattaaa   240
aaaaaaatca ttgtatcaat aaatttattg tttactatca aatccattga ttactgaata   300

SEQ ID NO: 89           moltype = DNA   length = 300
FEATURE                 Location/Qualifiers
source                  1..300
                        mol_type = genomic DNA
                        organism = Dirofilaria immitis
SEQUENCE: 89
aaaatgtatc aaattcttcg atgccataaa ttatacagac ttgattggca ttttttctaa    60
cttcatcat gaaccattct atttctaaat tgatccatta caaaatcaac tttgtgatat   120
catcaatctc agtcataacg agaaataatg ataatataaa gcgactatca tttgaatttc   180
ctgaatattc aagatgtaat tacatctttt ttttaatgta atcaaaattt cttgccatca   240
ataatttttc aacatatgct ttcatcgact gccttatgca gatcgtaatg atgacagcca   300

SEQ ID NO: 90           moltype = DNA   length = 300
FEATURE                 Location/Qualifiers
source                  1..300
                        mol_type = genomic DNA
                        organism = Dirofilaria immitis
SEQUENCE: 90
attgattaaa aagaatcaac attaaatttt tgatatagtc gagaaatcct tcgtgataat    60
tcttttagaa caattcttta cactaaactt gtatttactt gcttattatt tgtctaaaga   120
tactaactat ttgtcagtgg aatttatgat cttggcatta ttgcatataa cgctttccta   180
aaatctgaaa ttttttcagta ttttaaaaac taagacgatt attaaatatt actcaaagct   240
tagaactttg attatactaa tcaaatcaaa aatttcatca gcgattttg ttgtgtcatt   300

SEQ ID NO: 91           moltype = DNA   length = 300
FEATURE                 Location/Qualifiers
source                  1..300
                        mol_type = genomic DNA
                        organism = Dirofilaria immitis
SEQUENCE: 91
atttttccca gcagaattgt catcaaaaat cccattttg atatcctctt catcgaaact    60
tgctcctgaa tccagagaac aacgaagaat gtgtaaatct atttcagtag cctgctcatt   120
gtgcaattca gcgactttat ttctgtgctt caagctaact tcttcattat gccactcctc   180
ttctctcgct attttttcgc tatctaattc aaaatcttcg tctgaaacgg aatcaactcc   240
tgacgatgta ctcgacactg ataatatttt catgccgatt tttctctcaa acgaatcttt   300

SEQ ID NO: 92           moltype = DNA   length = 300
FEATURE                 Location/Qualifiers
source                  1..300
                        mol_type = genomic DNA
                        organism = Dirofilaria immitis
SEQUENCE: 92
gaatgaagag caaaaaaata gtcacgacca cctgcaataa aaacagcatc tccgtaaaaa    60
tgattgaatt gattcccgaa atacgagttt atcaaattga gaattatgca aattaattat   120
cagcatgcag atttactgat tttatatctc tcataccgaa attaaggtga tgttttccat   180
ttctttgttt ccacaatgtc ttctttgtga atcgttttgg atcaactatt aatccgatcg   240
aatcaatcct ccaaatatga gtttattcaa cgtaacaaaa cattgtccga gataatcaaa   300
```

| SEQ ID NO: 93 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 93

```
tggaaatttc gaaatcgaaa ggatgaagaa aaaggatcct tgatctatac attaaatatc   60
accatatcaa ctagcatggc aagtcaaagt aatgttatca tttaaataaa aaagatgaat  120
agtaggacta caggttatat tgttaaaagt cgacaaattt ggagtaattg acagagatca  180
acgattaaat gtaatggatg atcttatctt cttttttcaa ctacgccaaa atgaaaataa  240
caattgaatt tgtcgaataa gaaactaaca ttttgaaaat aagattgaac atttataaat  300
```

| SEQ ID NO: 94 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 94

```
ggttggatca ttatcgacag aactttagaa gtttcttgat aaggacgaaa agaagcagca   60
ccattgctga tctaaacaag gaaaaaagac ctttttttgga atattgaagt ttttactgat  120
aggtgcgtgc tgtgtactgt gggcataagt acaagcttca tgctccgcag cgtgaatacg  180
tgctgcatgc atactatgca gtaaaggtgc gtgtcgtatt gctcaataag tgtataaatt  240
gctgcttttc ttgcatagtt aaatattttg ttttcatttt ttccgctatt caaaataaat  300
```

| SEQ ID NO: 95 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 95

```
gttgggattt cagactctca ctcggtgtcg tttcacagtg atatctgaat cgaagtcaca   60
agcaggtatg aatgcataac aactaatatc cattgcagaa acaaggcaaa actgagaagc  120
tcgagcaata tagctataga agctggtacc acagatgaca ttcatggta tttccatttc   180
agcttcacaa acattgtaaa tagcttgctt cgatgattca atatctcgtt ctacgatatt  240
cttaaagtaa ttttttattta tttgaagtat agattacatc catgttctat ctatcatttc  300
```

| SEQ ID NO: 96 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 96

```
tgttctgaac atctcttttt gattatcttt tttaattcct ccattatttt cgttttttttc   60
gttgtgaatt aatattgttt gtctttgatt cagatgatat tttcggatcg taaatagatg  120
gcatcggcat aagcgtattg agaagcattc aatggtgcac tcttgcttct ttttttttttg  180
aaatctttc cgataatcaa ataagtgcag gatgccaatc attaacaatt tcgttccact  240
ttttcagttc ttattcttat aacaccacat ctcatttgca attttgtcgc caatgatttt  300
```

| SEQ ID NO: 97 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 97

```
ttttttcgag gtcactctgg aaaaataaat catattttaa aaagacataa aataaaaaat   60
atgtatatat aagaaaattt ttactctgaa tttcttaaga aaattctcga ttctgttttc  120
cataaattcc ggaatatgtt gtccctgaat taagaattcg attccttgca caccattatt  180
tcgtctagtt cctgtgtgaa caatgtaacc tggaaatgaa cacataaact gtaatatttt  240
gagcttaaaa taattatgag gatgcgaaac tgaagatatt cataaatgtt taaaaaaaaa  300
```

| SEQ ID NO: 98 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 98

```
gtccatgcat tgcttttcgg aagttagtgt agattcagtg aatatttaat accagtctct   60
ttctaattca aaagagcctc ccatttcttt tttcagtttc agtctctgaa tcagagcgtg  120
taatctacca ctccattgcc gaaaacagct cgatgtattt cctgctacgt agtgtttaga  180
attggcgtat gccacttgct cattattcgc gcatgaagtg taactgtgaa tagaatgata  240
ctactgttag aagagaatgc gttcacttta tttaacatta tactgattca tttcttcttt  300
```

| SEQ ID NO: 99 | moltype = DNA length = 300 |
| --- | --- |
| FEATURE | Location/Qualifiers |
| source | 1..300 |
| | mol_type = genomic DNA |
| | organism = Dirofilaria immitis |

SEQUENCE: 99

```
agtgaacgag aaaaaacaga agaagagata gcacatcaag atcgtgagaa attaattaga   60
```

```
caagaaaaag ctcgtcttac acaaatatat caggttttct ttttcttgct ttcgaaagtt  120
atttgaatta tctcatttct ttgaatttta taagaaataa tttaattttt ttttgaaatt  180
ttgcctattg agctctaaat tttgtaaaaa gttttctagg atgatgttag caaagcaaaa  240
aagaaatcca aaagtgatgg taacaaacag gaagatttta tagtgaggta cgataatacg  300

SEQ ID NO: 100         moltype = DNA  length = 300
FEATURE                Location/Qualifiers
source                 1..300
                       mol_type = genomic DNA
                       organism = Dirofilaria immitis
SEQUENCE: 100
tagacaatat catccttcct ttttttttgc tcaatttctc tgctcattgc tttgatgata  60
atggtaggtg gtataatgaa acgaatagat aattgatgtt cgcaaacatt tgctgttaaa  120
tttcagtaaa gaaattgacc tttttgcttt gtgttggatg tttagcttca ttttcttctt  180
gttcattgtc atattcattc tctcaaaact tcttgcttag cgatgctaat ataaatactg  240
gaagaatgcc tttgctttgt tttagttgta aatcatcacc aaggtatttt tttgcaaaat  300

SEQ ID NO: 101         moltype = DNA  length = 300
FEATURE                Location/Qualifiers
source                 1..300
                       mol_type = genomic DNA
                       organism = Dirofilaria immitis
SEQUENCE: 101
aagatgaaac taaaaaaaat tatttcgaaa aaaagaaaat aaaattaatg aaataaaagc  60
aaaaatgaac aaaccgtatt aattttaaac aataaacaat atcgaaatcg aaaaatggac  120
tattattgat gaactatatt ttcaaaatgt gaaaggtcaa agtttgtttc aattatgata  180
aatacaattt aaaataagat taagctaaca aataagttga gcaaattgat gaaacaaaca  240
aatcagaata tattacagaa aatgatataa catgaaaata tattagacca attattttta  300

SEQ ID NO: 102         moltype = DNA  length = 300
FEATURE                Location/Qualifiers
source                 1..300
                       mol_type = genomic DNA
                       organism = Dirofilaria immitis
SEQUENCE: 102
ttgaagtttt cagataaact ttgataaaaa attgttctat gaattctcaa atttcaatta  60
gtgatactta tttcgaaggt aattatgcct gattgaatct tcaatatcaa caaaatgaaa  120
attttagtat gattgttaac tcatacacct ctaattaaag gtattttctt tatcccatga  180
aatgaaaatt tattaagaac ttagaaagct acggtatgcc tttgatgcaa aagaaagatt  240
cattttcatt aaatcatgtt taaaaaaaag agcaaagagc aaaaggtgat gaaagttttt  300

SEQ ID NO: 103         moltype = DNA  length = 300
FEATURE                Location/Qualifiers
source                 1..300
                       mol_type = genomic DNA
                       organism = Dirofilaria immitis
SEQUENCE: 103
ttctatacga aatatttgtc tgccataaat ctactcagga actcgataca tcaaaacata  60
agtacgcttg ctctttattt ttcgtttgaa aaataaatag atcattttcg cacttacatt  120
tcaatttcaa ttgctttatt catatctttc tgtttttact tactggtatt taacagtcgt  180
tgttcacaat ttaatgatct atgaaacacc atttaattgt atttggacta acttttcgac  240
aagcaaaaga ttaaaattgt cttcagatac agttataaat ttacattgaa gataaatgaa  300

SEQ ID NO: 104         moltype = DNA  length = 300
FEATURE                Location/Qualifiers
source                 1..300
                       mol_type = genomic DNA
                       organism = Dirofilaria immitis
SEQUENCE: 104
taacgatctg tatatcaatg gaataatatt cagttcatgt tgtactcgat atgagataga  60
attacaattt tggaacaaga taatctcaac agctattttc aagaatagtt aaattaggat  120
accattcaaa gaaactttaa aaaatgattt ccatacatta atgctttttg tgttttcgct  180
ctcgaccaga atccaggaat tgtccattat catcaatttg attaactttt atctttattc  240
taattcttca acatttctct aattgatatt agtttcaata ttttaataag taaaaattta  300

SEQ ID NO: 105         moltype = DNA  length = 300
FEATURE                Location/Qualifiers
source                 1..300
                       mol_type = genomic DNA
                       organism = Dirofilaria immitis
SEQUENCE: 105
ataatgtgtt attgatcaaa ggatttttag ttacctacca gatggaaaaa aagcaagttt  60
acgaaaacag aagttagcat caactttcat ccatggttac accgtatata atccaatcga  120
ctcatacttt atgttgatct gattttatag cagataacta gttaccttgc tcagcagcag  180
ctaaatcctt tctatttgct taataacaga aatattttc attaacaaag aaattatact  240
ccgtgtttga catttcattt taatttcgtt ccaaaaatga aaaaagcttc gtccggaaat  300

SEQ ID NO: 106         moltype = DNA  length = 300
FEATURE                Location/Qualifiers
```

```
source                      1..300
                            mol_type = genomic DNA
                            organism = Dirofilaria immitis
SEQUENCE: 106
attattttgt agttttttcat ttttagttc aatttcctt tgcttattt aaatatgcca    60
ttctttattc agactcatag cgaatgcata tgttcattaa ttttttagt tacagttaca   120
aattctcaat ttctctttaa tcatttttt tccaaaaat agtctgagca ctcaaccatt    180
cattcaacaa ttgcagcttt ttttattgga gccttgtcaa attatcaatt cgtttccatg   240
tttattattg aaataataaa cggtatttag gataacgaag ttcgcttagc ttctttgact   300

SEQ ID NO: 107              moltype = DNA  length = 300
FEATURE                     Location/Qualifiers
source                      1..300
                            mol_type = genomic DNA
                            organism = Dirofilaria immitis
SEQUENCE: 107
aaaaattcag gtaatgagat cagtaatttt ttttggtcac tttgctgttt cttatcagct    60
cattgttatc catatcaaat gagcgaaagt gtgtatcaca tattggcaga gtgtaatcta   120
tgaagatttt gcgtatcaaa gtaattatga gagaactgat aatttatttt taagtagta    180
gaaaactcga attaagctaa taaataatcg gttgatatcc atgaaatgaa ttactaatga   240
aatgatataat tgagtaataa caaatgatat tcatgaagaa aggcaggttt ttttaatag   300

SEQ ID NO: 108              moltype = DNA  length = 300
FEATURE                     Location/Qualifiers
source                      1..300
                            mol_type = genomic DNA
                            organism = Dirofilaria immitis
SEQUENCE: 108
tatacttaaa acaagaaata caattaatgc caatagcaga gtgaaacttc tgaaaaataa    60
tgagttgaaa ctggtaaaat taacatttta ttagaaattt cagaaactta tgactcctca   120
tggcactatc acaaaatgtt tgaaaaaaat tgacagctcg cgtcgattgc aaaaatcatg   180
attcctgata tttagtatcg aacatgtgac aaataatata aagacctaac cataaagcac   240
tgaaacaact cgcggaaaca aaaaattaat ttgcataaac acggaatacg atcagaaaat   300

SEQ ID NO: 109              moltype = DNA  length = 300
FEATURE                     Location/Qualifiers
source                      1..300
                            mol_type = genomic DNA
                            organism = Dirofilaria immitis
SEQUENCE: 109
gaatttttt agaaggcttg aagtcgagaa tattagagac tatatcgaag acttaaataa    60
tcctggtaat cttctgtatg aatcaaaatt acctcgaaca gaaccattca gcacatcacg   120
agataattca tggaatgaaa ctagccaatc agagcgttgt aaaagaagaa agttatgaaa   180
tgacccttaaa atcaatttaa agcatgtcct cgccatataa gcgttgaaaa gttaggatag   240
aatcaattat caaaaaaata tgttaactag atcttatcaa tcaaaacatc agaaggaaaa   300

SEQ ID NO: 110              moltype = DNA  length = 300
FEATURE                     Location/Qualifiers
source                      1..300
                            mol_type = genomic DNA
                            organism = Dirofilaria immitis
SEQUENCE: 110
atatgataat agtgaaacaa ttccatcaca ataatatta tcgattagga gataaattaa     60
cattgatgcc tcaattttgg tcaacaatat atatttgcta ttagcatttt tattaaatcg   120
tttttatctg acttgacata aattgaaata gaaaaaattg aatctgttcc ttgttagatt   180
ttcttctaaa aattcttgaa atacaaataa tttcttaaat ttcaatattt ctacataatg   240
tattgcgaca aaaatgctaa tgattggctt attattattt cgaataattt tttaatcaaa   300

SEQ ID NO: 111              moltype = DNA  length = 300
FEATURE                     Location/Qualifiers
source                      1..300
                            mol_type = genomic DNA
                            organism = Dirofilaria immitis
SEQUENCE: 111
agctcgaaga tcggacaaaa tttgttcagc ttgttgcctt gaggcttag tctgaaaaga     60
cacttaaaag tataaacaaa ttatattcaa aaaatcttat tttgcatttg cgtcttaatt   120
tttgctttt gcaagttttt ttccgagcaa gtttttctat cttcgaaaag attatatcaa   180
ttaaaatttc aatttaagca atcattgcct cttcgagttt ctgtttcagc aaataaatat   240
caccaccacg acgctgtcgg aagaaagaaa cgccttttcc aatttctcgt ctcaactttt   300

SEQ ID NO: 112              moltype = DNA  length = 300
FEATURE                     Location/Qualifiers
source                      1..300
                            mol_type = genomic DNA
                            organism = Dirofilaria immitis
SEQUENCE: 112
taagaaagct gggagatttt ccaaaaacac tatttcccac gatttgttgt tttctatgat    60
caattcttaa tcaaactctg aaattctcaa atttttcgatt tctatccaac ttctacatat   120
ttttttagaa aattcatatt tagcaaagct gagtgtagaa ataattcata cttgcaattc   180
```

```
atttttctta aatttttcgaa tttcttaaaa aagtatttca aattacctac caattttgat    240
tggaaaattc gtggatgcta aaaattcaaa tcaaaatagt taaacagtat tcctaattgt    300
```

SEQ ID NO: 113          moltype = DNA   length = 300
FEATURE                 Location/Qualifiers
source                  1..300
                        mol_type = genomic DNA
                        organism = Dirofilaria immitis
SEQUENCE: 113
```
aatttaaaaa acacatcgac attttgcggt acggtaatga ttgtttacag taactaaatg    60
tgtcctacgg tagtaatact cgtgtacgta atgaatgagt atagtgaccg gatatttcct    120
tcactagtag gcaatattaa gaagtatttt cattttcata ttctatctaa aataaaccga    180
taaaatggtt tttgaattat tactttttca ttgttatttt ttgatcctaa attgtaaaat    240
actgtaataa tttagctaat ttctatgatt ctattcaata tgcttaaatt aaaattctaa    300
```

SEQ ID NO: 114          moltype = DNA   length = 300
FEATURE                 Location/Qualifiers
source                  1..300
                        mol_type = genomic DNA
                        organism = Dirofilaria immitis
SEQUENCE: 114
```
tcgtatttgt tgtatgtaat atagaaatat tgtttaaatt caatatgtag aaaaaatttc    60
tannnnnnnn nnaattaatt acatattaac tcgtatttgt tgtatgtaat atagaaatat    120
tgtttaaatt caatatgtag aaaaaatttc cataataaag acgaacagca tttataatta    180
tcaatgataa gttgaaatta attcatcaat gataagttga aattaattta tttgaaataa    240
tttctttgaa attcgaatat agacgagaat ttttttttt ttgctaatcg tttatcaaat    300
```

SEQ ID NO: 115          moltype = DNA   length = 300
FEATURE                 Location/Qualifiers
source                  1..300
                        mol_type = genomic DNA
                        organism = Dirofilaria immitis
SEQUENCE: 115
```
tctagcaata taaattacaa gaatatgccg tccaagtatt tcagaattta ttattaattt    60
ggataataat acattgtaaa tactgcgtat tctggattat tatgcactgc ataataacat    120
gcaatttcgt ctacatatcg cgaataaacg ccaaaagatt tctcgataaa agaaaatata    180
agaattcgta aatgaatgtt gtgtcagaga tatgtgttaa ttcataagtc aagatgttgt    240
aaatcgatcc atattagtaa tcatatttac gtgctcgtaa ataaaagcgg tgattcttgt    300
```

SEQ ID NO: 116          moltype = DNA   length = 300
FEATURE                 Location/Qualifiers
source                  1..300
                        mol_type = genomic DNA
                        organism = Dirofilaria immitis
SEQUENCE: 116
```
atcgaaaaaa gatgatctga tgacggaagg cgaaatgtct gcagaagcta agatgacgga    60
agaaaaaagt gaagaaatga aagaagaagc tggtaaaact cagaaggaat gtaaaactgg    120
agaatcgaaa aaagatgatc tgatgacgga gggcgaaatg tctaaagaag ctaagatgtc    180
ggaagaaaaa agtgaagaaa tgaaagaaga agctgataaa actcagaagg aatgtaaaac    240
ggaagaatcg aaaaaagacg atctgacgac agaaggcgaa aaatctgaag tagatgagcc    300
```

SEQ ID NO: 117          moltype = DNA   length = 300
FEATURE                 Location/Qualifiers
source                  1..300
                        mol_type = genomic DNA
                        organism = Dirofilaria immitis
SEQUENCE: 117
```
actaatgata agaaacggag ccgacgattt taggaaatga ataataacga cattgacaac    60
cattgttaga aaattgatag tactgataat aaaagctagt tatagaaaat tgataataat    120
aataaaattg ctggtagcaa atgtctagaa gtgataataa aattaatgat agcaaatgga    180
ttagcaatga taattaaaact gatgatagcg aatggattag taatgataat aaaattgatg    240
atagcaaatg actaataatg gtaataaaag ttaatgctag tgataacttg tatttttaagt   300
```

SEQ ID NO: 118          moltype = DNA   length = 300
FEATURE                 Location/Qualifiers
source                  1..300
                        mol_type = genomic DNA
                        organism = Dirofilaria immitis
SEQUENCE: 118
```
acagtttata gttacaatat tctccggtga ctaactgtat tttacaactt ataattatag    60
attacaaaat atattatagt agttttataa ttacagtatt cttaagtgaa taactatact    120
ttacagctta cagttacagt agttttctat gttttttgaat attaattta catgttttt    180
cctagtttca gtttcaaaat tttcagatat tttatgtgtt aaagcaaatt atattcgaga    240
tataaaaagt actggtcata tcttacaatt ctcatccttc tatattggaa agaattgagt    300
```

SEQ ID NO: 119          moltype = DNA   length = 300
FEATURE                 Location/Qualifiers
source                  1..300
                        mol_type = genomic DNA

```
                         organism = Dirofilaria immitis
SEQUENCE: 119
gtattgggac cgcgtatcgg gaaatctgaa agaagtcttt aacagtattt taaatgaata  60
attcaaatcg ttacttctta atatattaat ttatgcgtat atatgcagta catagcattg  120
cttaaattct tatttttccg cggttaaaac cctatgtaag ataagggagg tgattgtatc  180
tgcgccgtac tccttgtttt aatctacctg cttgttgtat atcctccaca tattgtaact  240
gcagcttcac atttgcatat atagtaaggg catcgttgtc tccagaagag atatattatc  300

SEQ ID NO: 120           moltype = DNA  length = 300
FEATURE                  Location/Qualifiers
source                   1..300
                         mol_type = genomic DNA
                         organism = Dirofilaria immitis
SEQUENCE: 120
gctgcccgaa tgttacaatt aggacgaaag taaaagtagt tgactgtagg tatgacgata  60
aaggaaaaat ttgtatctta agactttaca atttctaaat attacgtgtt ttatcgtgct  120
aacatcacga attccatatt cacaaaaaaa attttgtaga actccatctg gtttggatga  180
atttgctaca gttgaactgg atgatggaac gaaattgcaa acatctctta ttgttagtat  240
tttctaaatt ctgtgaaatt ttgcaacggc attcatgttt aattattaat ttggagaaag  300

SEQ ID NO: 121           moltype = DNA  length = 300
FEATURE                  Location/Qualifiers
source                   1..300
                         mol_type = genomic DNA
                         organism = Dirofilaria immitis
SEQUENCE: 121
aaataagcaa atccgaaagt attacatata cggactaaat attgccattc attcgggagt  60
ataccattgc aaccattggt atttcatttg atcgagaaaa ctagtttttg tagtttggga  120
taaagagaaa tggagagagg aactttcatg atcaatttct ttacgtactg aaattcattt  180
ctatggatgt tctttttcta tttcattctc ctcagcaaat acagtccgaa cagtcatcaa  240
ataagtctaa aaggcatgaa taatataaac atcagcaact ttttaaatga atgcttatta  300

SEQ ID NO: 122           moltype = DNA  length = 300
FEATURE                  Location/Qualifiers
source                   1..300
                         mol_type = genomic DNA
                         organism = Dirofilaria immitis
SEQUENCE: 122
atttctataa acatctcttg cattgattaa tttaacatgt tgcaataaat atttcttact  60
tttgaatgta tcatttacta gaaaaaactt caatcgagga aataagtttt aaaataaatt  120
catatttgaa ttcatgtcag ttcaaaaatt ctattactat aatacatgtc tcttggttgt  180
atcttttttt cttttgaaat aatacaatca aacggtttcc taaattttca tagacatcat  240
attttaaaaa aaaatgcatt tgaaaatttt cgaaaatcaa tgaacttaat tgatgaaaaa  300

SEQ ID NO: 123           moltype = DNA  length = 300
FEATURE                  Location/Qualifiers
source                   1..300
                         mol_type = genomic DNA
                         organism = Dirofilaria immitis
SEQUENCE: 123
gcatgtgtat gtagtatttc tttgtaaaca acatatctaa tctgtctgtc cctttaacat  60
tatagaatag tcagttagtc cgctatttat tttaataaca aaatatctca cttaacttcc  120
atttctttcc taaataattt tgtttcgcta gatctttcct ataattttca aattttcaaa  180
aatgaattaa tcttttattt atatatgtgt atgtatgtgt atgtatgtat gtgtacgttg  240
catatatgta tatgtatgtg tgtatgtgtg tatatgtata tgtatatgtg tgtatgtgtg  300

SEQ ID NO: 124           moltype = DNA  length = 300
FEATURE                  Location/Qualifiers
source                   1..300
                         mol_type = genomic DNA
                         organism = Dirofilaria immitis
SEQUENCE: 124
tatgcataat gtgcgaccag ccaataatgt cttcaaacca taattatgca gaaataaatt  60
ttttccagaa ataatttttt tttttttaca tatacttccg atctgtgaga aaatacattt  120
gaagtgaagt gtgaagcaat gctacttttt caaacaacat tgtgaaaatg gattaaaacg  180
caccaatgga gcaagagatc gtaagtttcg ttccgcatgt cctgtggcaa cgtgtaaacc  240
atccgttaac gatatatgat gtaaaagccg acacacccaa attaaaatcc attataaaca  300

SEQ ID NO: 125           moltype = DNA  length = 300
FEATURE                  Location/Qualifiers
source                   1..300
                         mol_type = genomic DNA
                         organism = Dirofilaria immitis
SEQUENCE: 125
aaatggatcg tattcacttc gtaagaactt agtgaacgaa aaatcaaacc atcacaataa  60
ctttactttt tttctttttt tactaaacac actatcctat gaaaacaaaa tgtccaaata  120
gattcatatg ataatgaact gtgaagttat ccaatctatc agttctcgaa gagggaataa  180
ataaaaacat taagcaaccc accgatcttc gctgaccatc tccttcttca ttagcaagaa  240
gcaaatcttg tggtgatatt tctgcaacca tctgcaaaat aaagcacgaa aaattaagga  300
```

```
SEQ ID NO: 126          moltype = DNA  length = 300
FEATURE                 Location/Qualifiers
source                  1..300
                        mol_type = genomic DNA
                        organism = Dirofilaria immitis
SEQUENCE: 126
tttgatatgc aatcaactaa ccaaatcaga attcaatgca ttctgataaa tttcttcaat  60
atcgtgcatc aattcgacat catattttga cagtgatgct acctttttag ccgtatttcg 120
gaaaaatatg aattcaacca gctgcgtccc aaaatttaag gctgtagcaa gtccagcaac 180
aaccagccct acaactgaaa attctaaaaa ctggttcacg tgcttatcat taataatttc 240
aacactatca ctatctccac atgaacttga tcgattataa tttagtagaa ctgaaaaaaa 300

SEQ ID NO: 127          moltype = DNA  length = 300
FEATURE                 Location/Qualifiers
source                  1..300
                        mol_type = genomic DNA
                        organism = Dirofilaria immitis
SEQUENCE: 127
acaaattcgt tttaatattg gattacattg aaattgctga aataaagtgg aaatattgaa  60
aagcatttta caatatttgt taacaacatt atatttaaag aatatacacc ttggtttaaa 120
tggtaaaata atctcaagaa ttttcattag gttaattttt ttttatttat ttatattcac 180
aaaaaattgt aaaagaaaac aaaaacaaca ataataacgg tgacaacaac aacaataata 240
ataacaaaac tatttgttgt gattttgcag cattgatgta gtggggatct tttggagcga 300
```

MARKERS TO PREDICT MACROCYCLIC LACTONE DRUG RESISTANCE IN *DIROFILARIA IMMITIS*, THE CAUSATIVE AGENT OF HEARTWORM DISEASE

The present application is a divisional application of U.S. patent application Ser. No. 15/887,164, filed Feb. 2, 2018, which is a continuation application of U.S. patent application Ser. No. 14/896,736, filed Dec. 8, 2015, which is the U.S. National Stage filing under 35 U.S.C. § 371 of International Application No. PCT/US14/44000, filed Jun. 25, 2014, which claims benefit of priority to U.S. Provisional Application 61/839,545, filed Jun. 26, 2013; all of which are incorporated herein by reference in their entirety.

REFERENCE TO SEQUENCE LISTING SUBMITTED ELECTRONICALLY

Incorporated by reference in its entirety is a computer-readable nucleotide/amino acid sequence listing submitted concurrently herewith and identified as follows: as a 8 kilobytes xml file named "78045-366383_ST26.xml", created on Apr. 13, 2023.

FIELD OF THE INVENTION

Disclosed are genetics related to macrocyclic lactone (ML) endectocide resistance in nematode parasites (e.g., *Dirofilaria immitis*). Single nucleotide polymorphisms within the genome of *D. immitis* are disclosed that, singly or in combination, correlate with reduced responsiveness of the parasites to MLs. Also disclosed are methods for detection of these parasites, methods for treatment of these parasites, and methods and kits for determination of responsiveness of these parasites to MLs.

BACKGROUND OF THE INVENTION

Dirofilariasis is a parasitic disease of animals and occasionally in humans, which may result from infection by a species of *Dirofilaria* such as *D. immitis*, *D. repens*, *D. tenuis*, *D. ursi*, *D. subdermata*, *D. lutrae*, *D. striata* and *D. spectans*.

*Dirofilaria immitis* (heartworm) is a parasitic nematode that commonly infects dogs, foxes, wolves, coyotes, and cats. Heartworms may cause serious vascular damage and may be fatal, especially in highly active animals.

The life cycle of *D. immitis* is well known (reviewed in McCall et al., Adv. Parasitol. 66:193-285, 2008). In brief, a mosquito may become infected when it draws blood from an infected host (e.g. a dog). In the mosquito, microfilariae (mf) develop to the infective larval stage. When the infected mosquito feeds, it may transmit larvae to a new host (e.g. another dog). In the new host, the larvae continue to mature for eight to ten weeks, after which time they move to the right side of the lungs and the pulmonary artery, where they become adult. Adult worms mate and females produce eggs, which develop in utero into the long thin embryos (microfilariae) that are released into the bloodstream. A mosquito that takes in the circulating mf when it draws blood from the infected host starts the cycle again.

*D. immitis* may be found wherever its vector, the mosquito, is found. Generally, *D. immitis* may be found on a world-wide basis, but are very common in areas with mild and warm climates.

Macrocyclic lactones (MLs) are often prescribed as therapeutics or prophylactics in the management of *D. immitis* in veterinary applications. Example MLs include ivermectin (IVM), milbemycin oxime (MO), moxidectin (MOX) and selamectin (SLM). However, resistance to MLs is common in a variety of parasitic nematodes and appears to be developing in *D. immitis*. A number of tests have been described for the detection of anthelmintic resistance in nematodes of livestock and horses, including, faecal egg count reduction test, the egg hatch test, microagar larval development test and molecular tests based on benzimidazole resistance (reviewed in Coles et al., Veterinary Parasitology 136:167-185, 2006). Prichard et al. (European patent EP 0979278) describes a P-glycoprotein sequence in *Haemonchus contortus* which may be useful for the diagnosis of ML resistance in parasitic nematodes. However, there remains a need for methods to detect *D. immitis* (heartworms) that are resistant to a ML.

SUMMARY OF THE INVENTION

Genetic variations (e.g., SNPs) have been discovered in the genomes of *Dirofilaria* spp. nematodes that relate to reduced responsiveness of the nematodes to macrocyclic lactones. In one example, the nematode is *Dirofilaria immitis* (the agent of heartworm in animals). In one example, the macrocyclic lactones are ivermectin, selamectin, milbemycin oxime or moxidectin.

Methods for determining the responsiveness of a *Dirofilaria* spp. nematode to a macrocyclic lactone are disclosed. In one example, the method involves determining the genotype of the nematode at a polymorphic site in a nucleic acid molecule that includes one or more of SEQ ID NOs: 1-127 from the nematode. In one example, the nucleic acid molecule possesses at least 80% sequence identity to one or more of SEQ TD NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment of the method, the presence of an alternative nucleotide at the polymorphic site in the nucleic acid molecules indicates that the nematode is likely to be resistant to the macrocyclic lactone. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

Isolated nucleic acid molecules comprising one or more of SEQ ID NOs: 1-127 are disclosed. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

Kits for determining the responsiveness of a *Dirofilaria* spp. nematode to a macrocyclic lactone are disclosed. In one example, the kit contains a probe capable of determining the genotype of the nematode at a polymorphic site of one or more of SEQ ID NOs: 1-127. The probe may be an oligonucleotide, a primer or an aptamer. Using the kit, the genotype of the nematode may be determined, for example, by DNA sequencing, hybridization-based methods including using allele specific oligonucleotides, microarray analysis, enzyme-based methods, single strand conformational polymorphism (SSCP), high resolution melt (HRM) or approaches based on PCR, RT-PCR, or qRT-PCR.

Methods for selecting a treatment to treat an animal infected with a *Dirofilaria* spp. nematode are disclosed. In one example, the method involves determining the genotype of the nematode at a polymorphic site in a nucleic acid molecule that includes one or more of SEQ ID NOs: 1-127 and selecting the treatment based on the genotype of the nematode. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment, the method involves treating the animal with one or more alternative agents when an alternative nucleotide is found at the polymorphic site. Alternative agents may include one or more of an arsenic-based therapy, diethylcarbamazine, and antibiotics. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

BRIEF DESCRIPTION OF THE DRA WINGS

FIGS. 1-28 illustrate the genotype frequencies for the SNP within each of the indicated markers, for susceptible and LOE isolates. The graphs are representative of markers that are also designated as SEQ ID NOs: 1-109 within the application. For markers designated with an asterisk(*), the genotype indicated shows analysis of the reverse complement of the sequences shown as SEQ ID NOs: 1-109 within the application.

Figure 1:
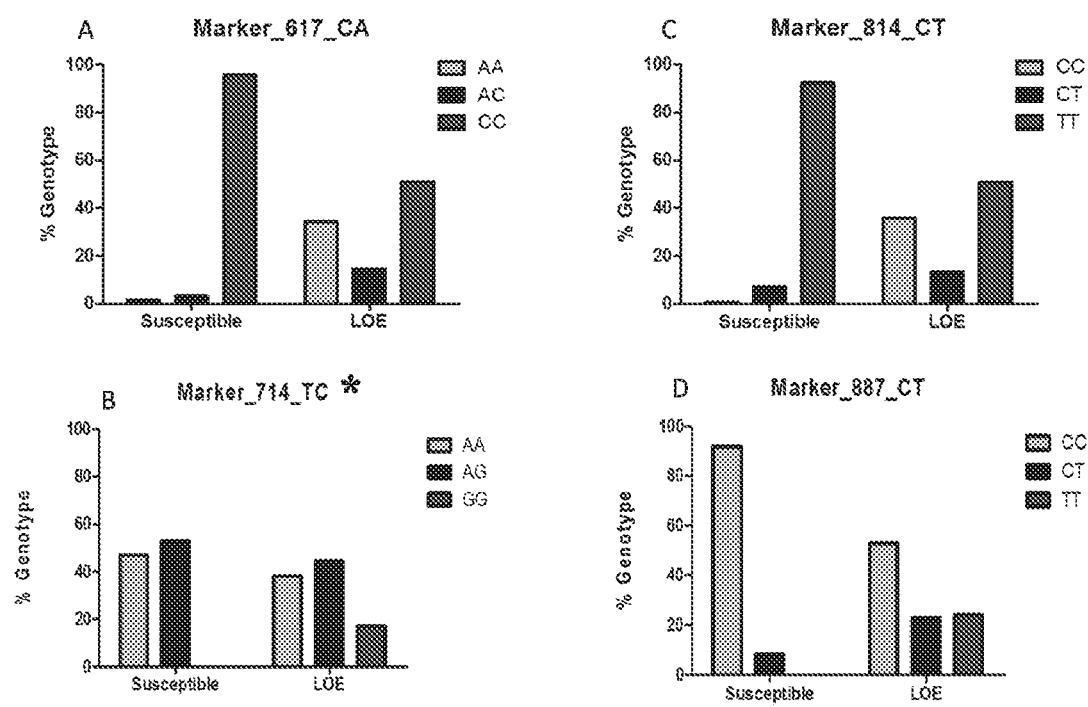
FIG. 1 illustrates the genotype frequencies for the SNP within Marker 617 (SEQ ID NO: 1), Marker 714 (SEQ ID NO: 2), Marker 814 (SEQ ID NO: 3), and Marker 887 (SEQ ID NO: 4).

FIG. 29 presents Table 1 which displays genotype frequencies for markers representing SEQ ID NOs: 110-127.

DETAILED DESCRIPTION OF THE INVENTION

Definitions

Herein, "macrocyclic lactones" or "MLs" means products, or chemical derivatives thereof of soil microorganisms that belong to the genus *Streptomyces* including, but not necessarily limited to, avermectins and milbemycins. These molecules are used to treat species of endo- and ectoparasites in a wide range of hosts. Avermectins in use include, without limitation, ivermectin, abamectin, doramectin, eprinomectin and selamectin. Available milbemycins include, without limitation, milbemycin oxime and moxidectin. Macrocyclic lactones have a potent, broad antiparasitic spectrum at low dose levels. They are active against many immature nematodes (including hypobiotic larvae) and arthropods. A single therapeutic dose may persist in concentrations sufficient to be effective against incumbent nematode infections for prolonged periods after treatment.

Macrocyclic lactone (ML) heartworm preventatives were developed for the treatment of dogs and cats, which were not already infected, to prevent establishment of adult infections by targeting the developing L3/L4 stages. Macrocyclic lactones also have effects on the microfilarial stage (L1). Macrocyclic lactone endectocides such as ivermectin (IVM), milbemycin oxime (MO), moxidectin (MOX) and selamectin (SLM) are used during the transmission season for chemoprophylaxis for heartworm in dogs and cats.

Herein, "responsiveness" means that a nematode responds following exposure to a macrocyclic lactone (ML). In embodiments of the invention, a nematode may respond by being sensitive or resistant to a ML. Sensitivity or sensitive to a ML means that the macrocyclic lactone adversely affects the exposed *D. immitis* nematode. For example, a ML may be lethal or sub-lethal to the *D. immitis* nematode, shorten its life-span or inhibit its ability to reproduce. Resistance is the reduction in effectiveness of a drug, herein MLs, in curing a disease or improving symptoms (e.g., eradicating heartworm organisms from a dog). A *D. immitis* nematode may be ML resistant if the drug is meant to neutralize it is ineffective, less effective or has reduced effectiveness. A *D. immitis* nematode may also be ML resistant if the drug, at a specific dose that is meant to neutralize it, has reduced effect. In embodiments of the invention, responsiveness of a nematode to a macrocyclic lactone may be determined in vivo or in vitro.

Herein, "loss of efficacy" or "LOE" means that there is at least a perceived decrease in responsiveness of nematodes to MLs. The perceived decrease in responsiveness may be perceived or may be actual. In one example, the decrease in responsiveness of nematodes to MLs may be real, in which case the nematodes may be said to be resistant to MLs. In another example, the decrease in responsiveness of nematodes to MLs may be perceived and not real. For example, in the case where a dog infected with heartworm is treated with MLs, for the purpose of eliminating heartworm from the dog, the dog owner may not be compliant in properly administering the MLs to the dog. In such a case, the heartworm infection may not be eliminated from the dog because sufficient doses of MLs were not administered, for example. The dog owner, or other observer, may mistakenly believe that MLs were compliantly administered to the dog (e.g., the owner believes s/he administered MLs as directed but, in reality, missed administrations, administered inadequate dosages, etc.) and, because the heartworms were not eliminated from the dog, the heartworm parasites are resistant to MLs. In at least some of these cases, heartworms are not eliminated from the dog because of the lack of compliance. In these cases, continued presence of heartworm may not be due to ML resistance of the heartworm organisms (i.e., the decrease in responsiveness of the heartworm parasites is perceived and not real). In cases of LOE, generally there is no confirmation that the heartworm infection is actually resistant to MLs.

Herein, "resistant" or "confirmed resistant" generally means that the heartworm organisms were shown to have at least reduced responsiveness to MLs. In one example, dogs infected with heartworm are treated with MLs, using a regime known to normally rid dogs of heartworm infection (i.e., compliance of the ML treatment is not in question), but the treatment does not rid the dog of heartworm organisms. Such heartworm organisms, which would normally be eliminated from the dogs by the compliant treatment, are not eliminated because of their reduced responsiveness to ML. Such heartworm organisms are said to be resistant to the MLs.

In one example, a *D. immitis* nematode may be said to be resistant to a ML if less than about 93%, less than about 91%, less than about 89%, less than about 87%, less than about 85%, less than about 83%, less than about 81%, less than about 79%, less than about 77%, less than about 75%, less than about 73%, less than about 71%, less than about 69%, less than about 67%, less than about 65%, less than about, 63%, less than about 61%, less than about 59%, less than about 57%, less than about 55%, less than about 53%, less than about 51%, less than about 49%, less than about 47%, less than about 45%, less than about 43%, less than about 41%, less than about 39%, less than about 37%, less than about 35%, less than about 33%, less than about 31%, less than about 29%, less than about 27%, less than about 25%, less than about 23%, less than about 21%, less than about 19%, less than about 17%, less than about 15%, less than about 13%, less than about 11%, less than about 9%, less than about 7%, less than about 5%, less than about 3%, less than about 1% or if 0% of nematodes died following exposure to a LD95 (a lethal dose or concentration of a drug that should have killed 95% of *D. immitis* nematodes) dose or concentration of a macrocyclic lactone.

In another embodiment, a *D. immitis* nematode may be said to be sensitive to a macrocyclic lactone if at most about 5%, at most about 4%, at most about 3%, at most about 2%, at most about 1% or if 0% of nematodes survived following exposure to a LD95 (a lethal dose or concentration of a drug that should have killed 95% of *D. immitis* nematodes) dose or concentration of a macrocyclic lactone.

Herein, "nucleic acid", "nucleotide sequence" or "nucleic acid molecule" may refer to a polymer of DNA and/or RNA which may be single or double stranded and optionally containing synthetic, non-natural or altered nucleotide bases capable of incorporation into DNA or RNA polymers. "Nucleic acids", "nucleic acid sequences" or "nucleic acid molecules" may encompass genes, cDNA, DNA (e.g. genomic DNA) and RNA encoded by a gene. Nucleic acids or nucleic acid sequences may comprise at least 3, at least 10, at least 100, at least 1000, at least 5000, or at least 10000 nucleotides or base pairs.

"Nucleic acids", "nucleic acid sequences" or "nucleic acid molecules" may be modified by any chemical and/or biological means known in the art including, but not limited to, reaction with any known chemicals such as alkylating agents, browning sugars, etc.; conjugation to a linking group (e.g. PEG); methylation; oxidation; ionizing radiation; or the action of chemical carcinogens. Such nucleic acid modifications may occur during synthesis or processing or following treatment with chemical reagents known in the art.

Herein, an "isolated nucleic acid molecule" may refer to a nucleic acid molecule that does not occur in nature as part of a larger polynucleotide sequence; and/or may be substantially free from any other nucleic acid molecules or other contaminants that are found in its natural environment. As used herein, an "isolated nucleic acid molecule" may also encompass recombinantly or synthetically produced nucleic acid molecules.

Herein, the term "identity" or "identical" refers to sequence similarity between two or more polynucleotide molecules, at one position in within molecules, or at more than one position within the molecules. Identity can be determined by comparing each position in the aligned sequences. A degree of identity between nucleic acid sequences is a function of the number of identical or matching nucleic acids at positions shared by the sequences, for example, over a specified region. Optimal alignment of sequences for comparisons of identity may be conducted using a variety of algorithms, as are known in the art. In one example, sequence identity may be determined using the well-known and publicly available BLAST algorithm (e.g. BLASTn and BLASTp). In another embodiment, the person skilled in the art can readily and properly align any given sequence and deduce sequence identity/homology by mere visual inspection.

Herein, "single nucleotide polymorphisms" or "SNPs" refer to genetic variations (or non-identity) at specific locations in a genome (i.e., polymorphic site). Generally, at a specific position in a genome, the identity of a nucleotide may be invariant or constant. At some positions in a genome, however, the identity of a nucleotide may not be invariant. At such positions, there may be a nucleotide present at the position at a relative higher frequency than other nucleotides, when the genomes of different individuals within a population are analyzed. The nucleotide most commonly found at such a position may be referred to as the wild-type nucleotide at this position. However, there may be one or more other nucleotides found at this position at relatively lower frequencies. These nucleotides may be referred to as alternative nucleotides. The frequencies by which the alternative nucleotides are found may vary. In one example, the SNPs described herein may play a role in responsiveness of nematodes to MLs. In one example, the SNPs may identify or tag a region of a genome that may play a role in responsiveness of nematodes to MLs (i.e., the SNP itself is not directly involved in the altered responsiveness to MLs but may be genetically linked to genetic changes that are involved in altered responsiveness). In one example, presence of one or more of the disclosed SNPs may indicate that the parasite whose genome contains the one or more SNPs is less responsive to MLs compared to parasites that do not have the SNPs.

As used herein, the term "polymorphic site" may refer to a region/specific location in a nucleic acid at which two or more alternative nucleotide sequences are observed in a significant number of nucleic acid samples from a population of individuals. A polymorphic site that is one nucleotide in length may be referred to herein as a "single nucleotide polymorphism" or a "SNP."

Herein, "marker" or "markers" generally refer to nucleic acid sequences that can contain one or more SNPs. These nucleic acid sequences can be of different lengths.

Herein, "genotype" refers to the genetic constitution of a cell, an organism, or an individual (i.e. the specific allele makeup of the individual) usually with reference to a specific character under consideration. In the context of this application, genotype generally refers to identity of nucleotides at positions of SNPs. In one example, aGG genotype may mean that at a specific position of a gene (e.g., a polymorphic site) which has two alleles, the nucleotide at the same location in each allele is G (guanine). Alleles are alternative DNA sequences at the same physical locus, which may or may not directly result in different phenotypic traits, but generally within the context of this application, correlate with decreased responsiveness of parasites to MLs. In any particular diploid organism, with two copies of each chromosome, the genotype for each gene comprises the pair of alleles present at that locus, which are the same in homozygotes and different in heterozygotes.

Suitable approaches for use in determining genotype are known in the art and may include, without limitation, PCR, RT PCR, qRT PCR, SSCP and hybridization with allele specific oligonucleotides. Other approaches may include nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA).

Herein, "consists essentially of" or "consisting essentially of" means that the nucleic acid sequence may include one or more nucleotide bases, including within the sequence or at one or both ends of the sequence, but that the additional nucleotide bases do not materially affect the function of the nucleic acid sequence.

Genomes and SNPs

Figure 2:
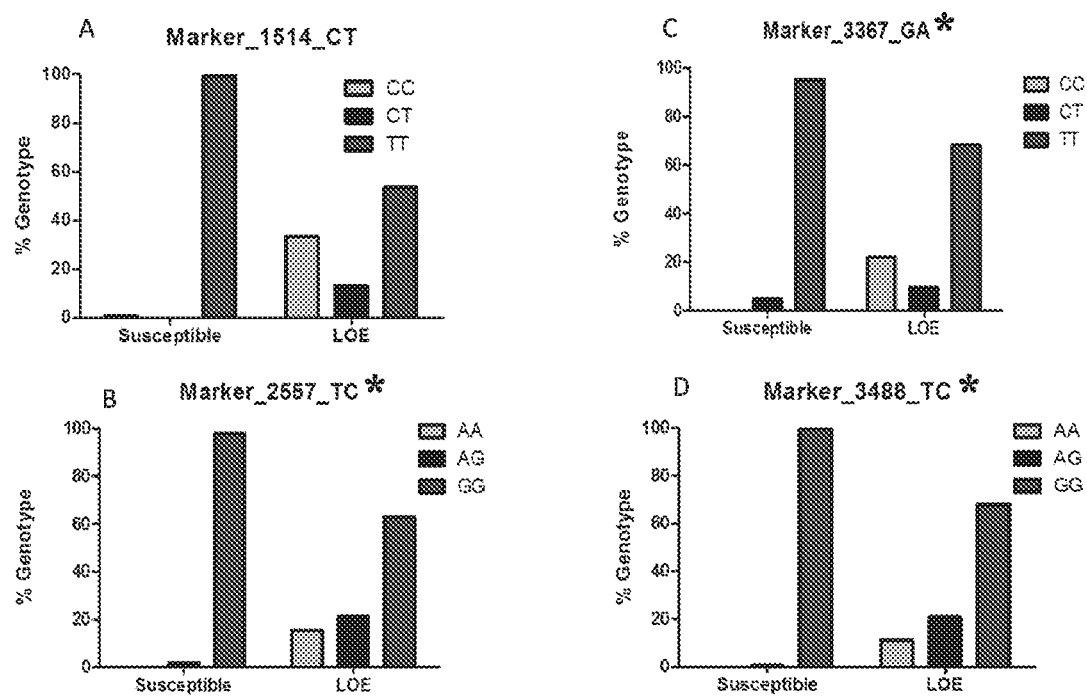
FIG. 2 illustrates the genotype frequencies for the SNP within Marker 1514 (SEQ ID NO: 5), Marker 2557 (SEQ ID NO: 6), Marker 3367 (SEQ ID NO: 7), and Marker 3488 (SEQ ID NO: 8).
Figure 3:
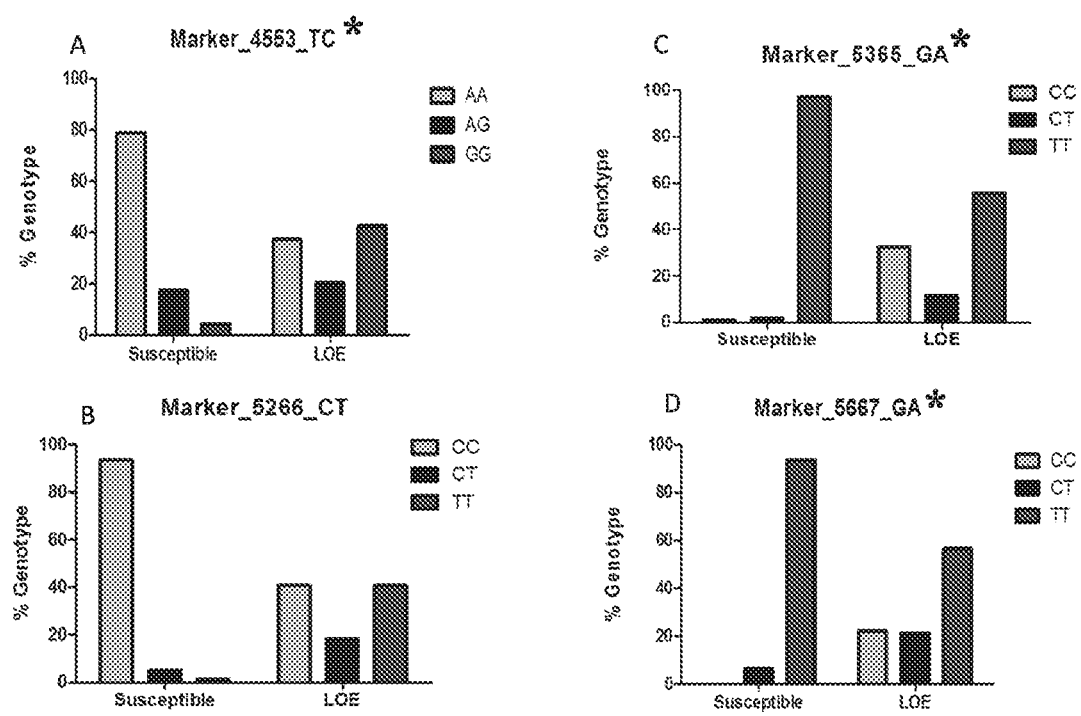
FIG. 3 illustrates the genotype frequencies for the SNP within Marker 4553 (SEQ ID NO: 9), Marker 5266 (SEQ ID NO: 10), Marker 5365 (SEQ ID NO: 11) and Marker 5667 (SEQ ID NO: 12).
Figure 4:
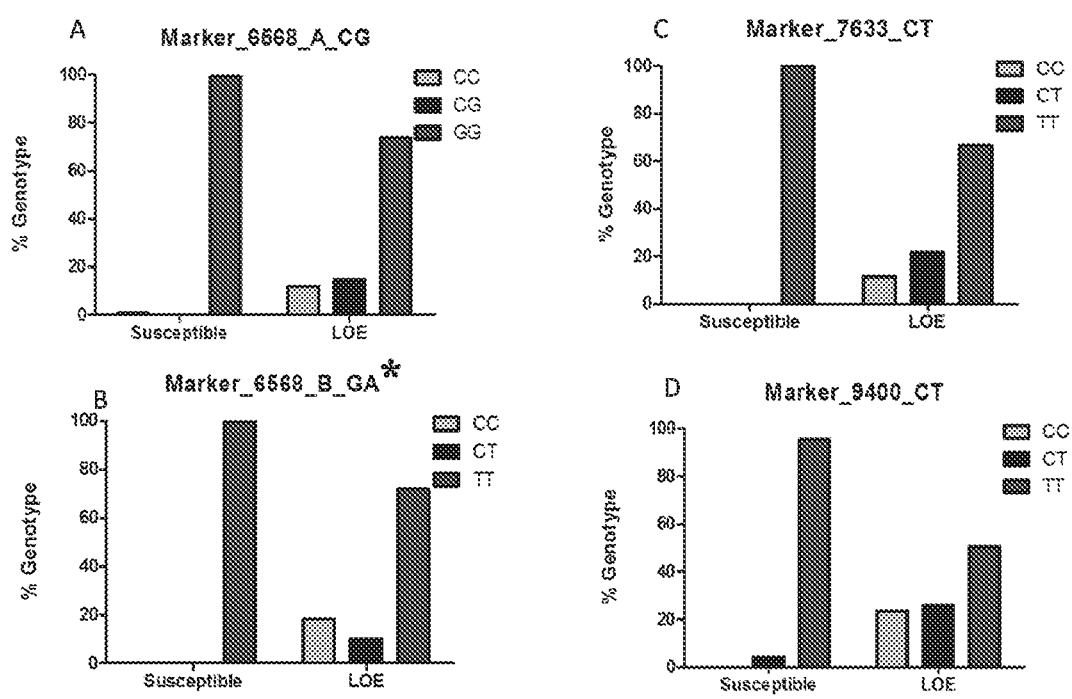
FIG. 4 illustrates the genotype frequencies for the SNP within Marker 6568_A (SEQ ID NO: 13), Marker 6568_B (SEQ ID NO: 14), Marker 7633 (SEQ ID NO: 15), and Marker 9400 (SEQ ID NO: 16).
Figure 5:
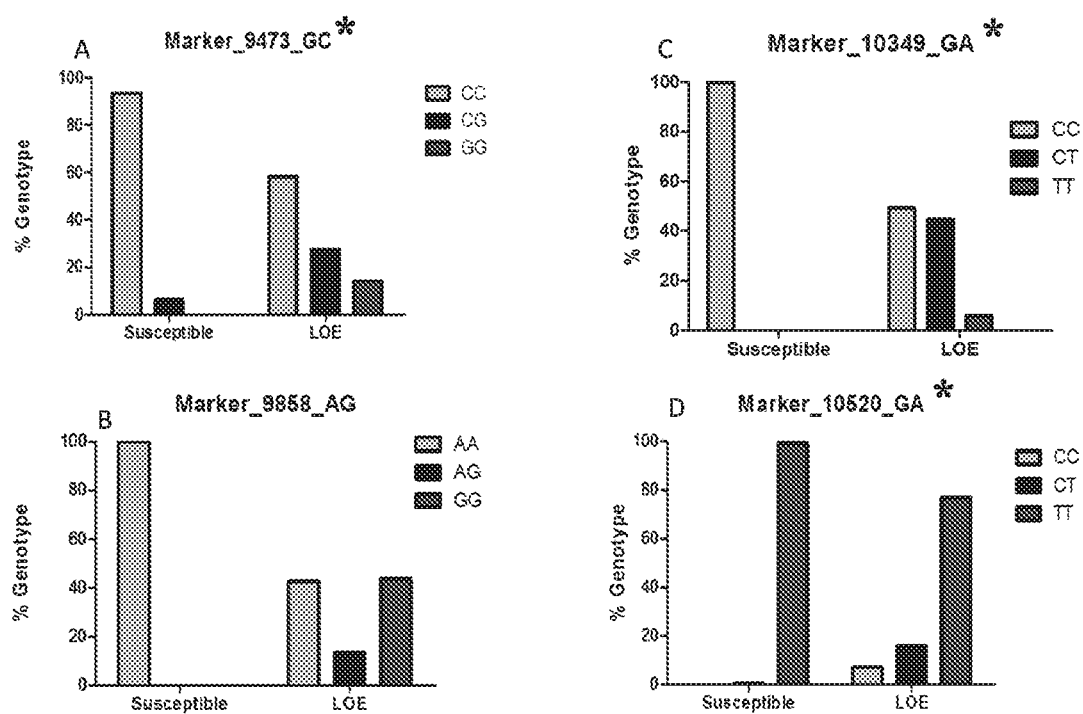
FIG. 5 illustrates the genotype frequencies for the SNP within Marker 9473 (SEQ ID NO: 17), Marker 9858 (SEQ ID NO: 18), Marker 10349 (SEQ ID NO: 19), and Marker 10520 (SEQ ID NO: 20).
Figure 6:
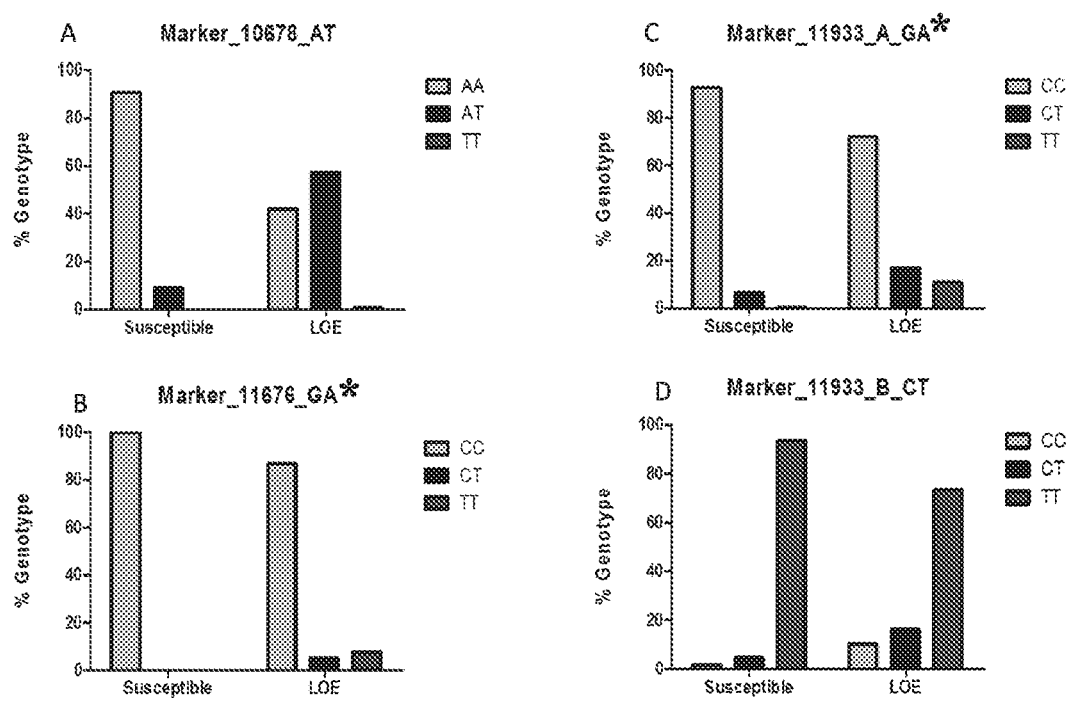
FIG. 6 illustrates the genotype frequencies for the SNP within Marker 10678 (SEQ ID NO: 21), Marker 11676 (SEQ ID NO: 22), Marker 11933_A (SEQ ID NO: 23), and Marker 11933_B (SEQ ID NO: 24).
Figure 7:
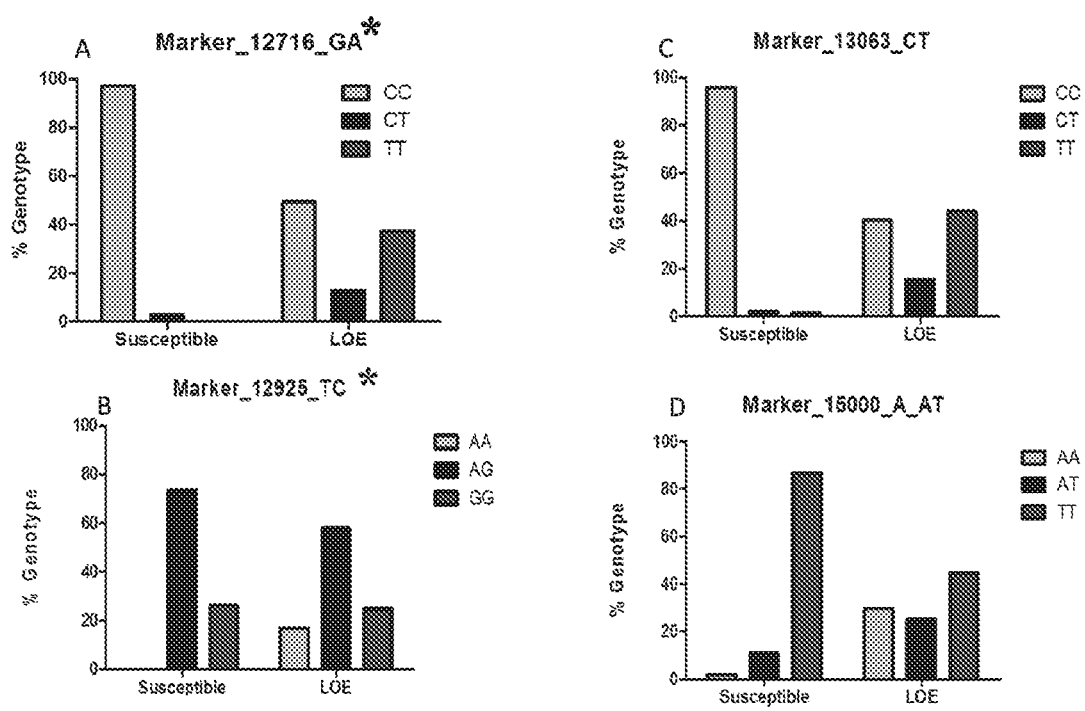
FIG. 7 illustrates the genotype frequencies for the SNP within Marker 12716 (SEQ ID NO: 25), Marker 12925 (SEQ ID NO: 26), Marker 13063 (SEQ ID NO: 27), and Marker 15000_A (SEQ ID NO: 28).
Figure 8:
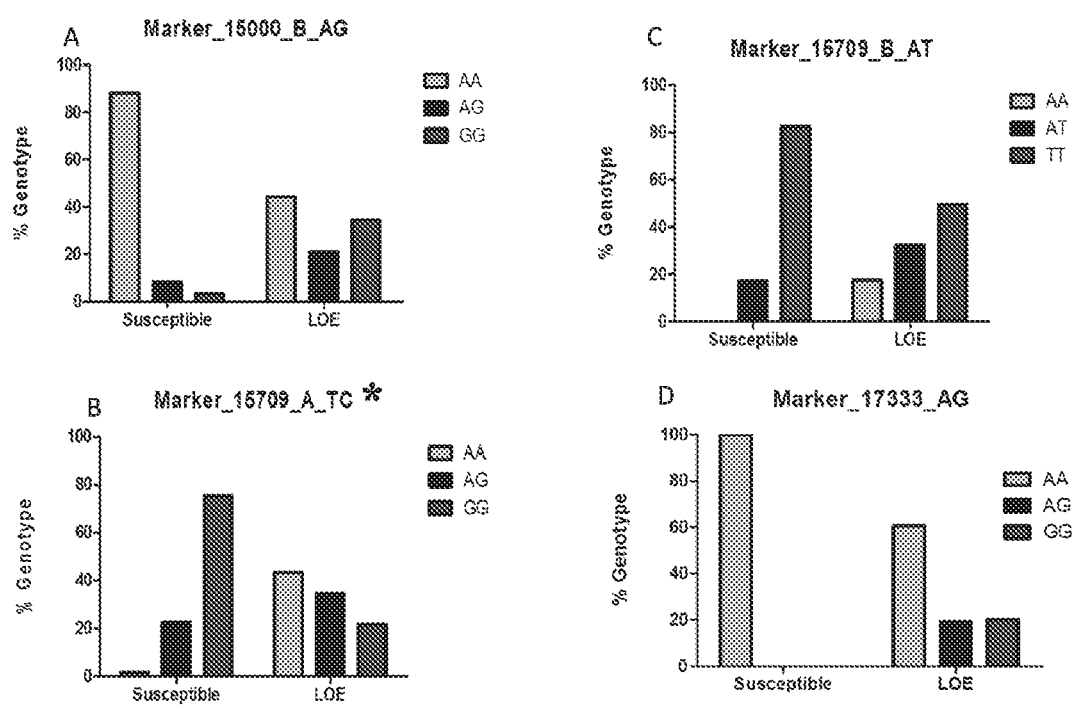
FIG. 8 illustrates the genotype frequencies for the SNP within Marker 15000_B (SEQ ID NO: 29), Marker 15709_A (SEQ ID NO: 30), Marker 15709_B (SEQ ID NO: 31), Marker 17333 (SEQ ID NO: 32).
Figure 9:
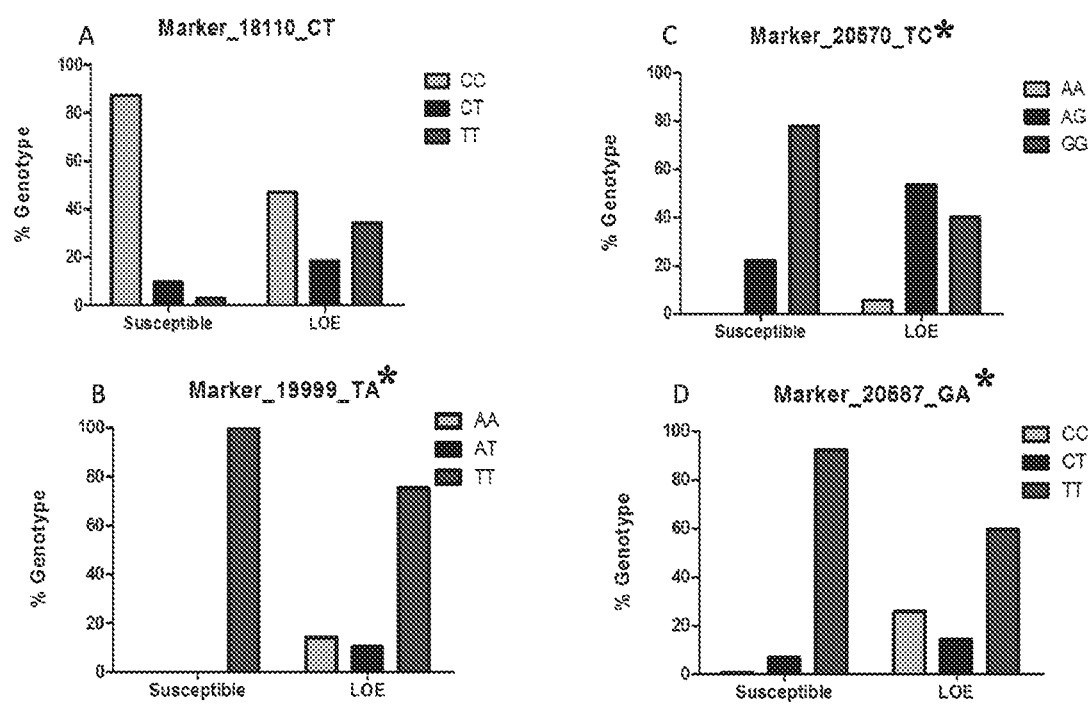
FIG. 9 illustrates the genotype frequencies for the SNP within Marker 18110 (SEQ ID NO: 33), Marker 19999 (SEQ ID NO: 34), Marker 20570 (SEQ ID NO: 35), and Marker 20587 (SEQ ID NO: 36).
Figure 10:
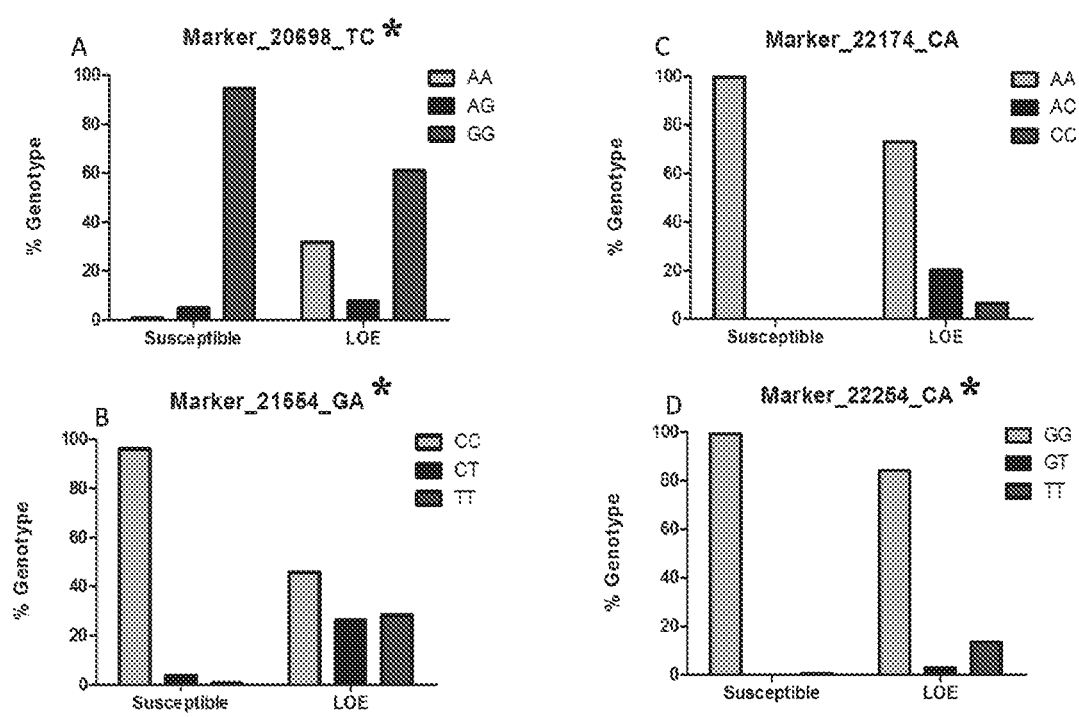
FIG. 10 illustrates the genotype frequencies for the SNP within Marker 20698 (SEQ ID NO: 37), Marker 21554 (SEQ ID NO: 38), Marker 22174 (SEQ ID NO: 39), and Marker 22254 (SEQ ID NO: 40).
Figure 11:
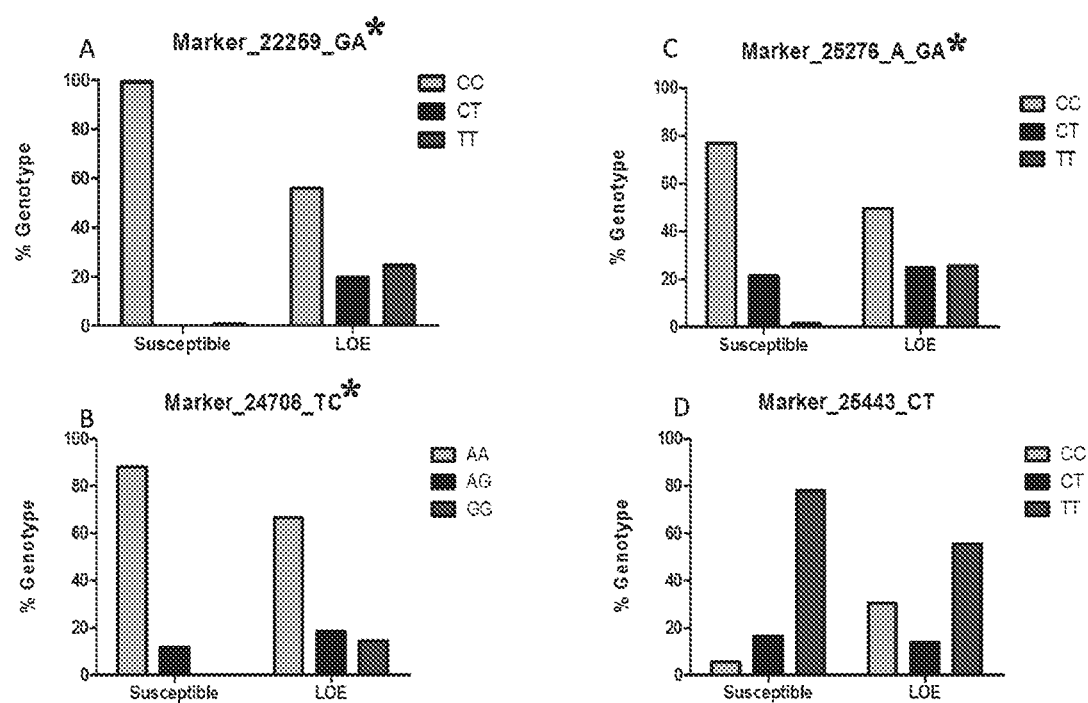
FIG. 11 illustrates the genotype frequencies for the SNP within Marker 22259 (SEQ ID NO: 41), Marker 24708 (SEQ ID NO: 42), Marker 25276_A (SEQ ID NO: 43), and Marker 25443 (SEQ ID NO: 44).
Figure 12:
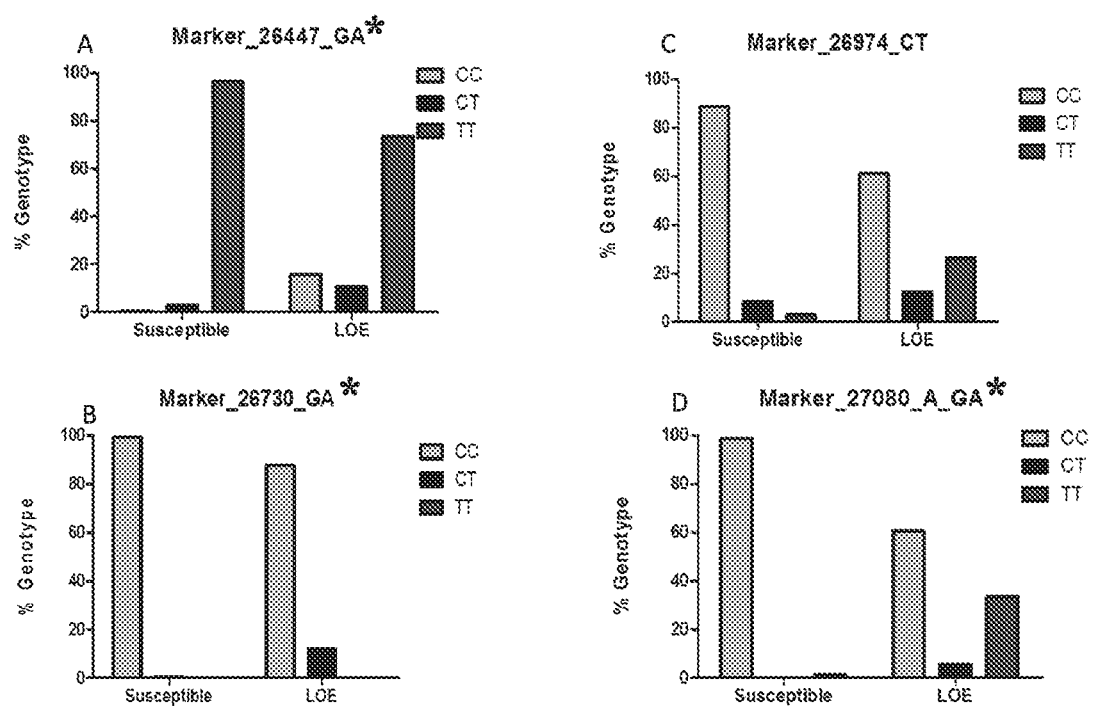
FIG. 12 illustrates the genotype frequencies for the SNP within Marker 26447 (SEQ ID NO: 45), Marker 26730 (SEQ ID NO: 46), Marker 26974 (SEQ ID NO: 47), and Marker 27080_A (SEQ ID NO: 48).
Figure 13:
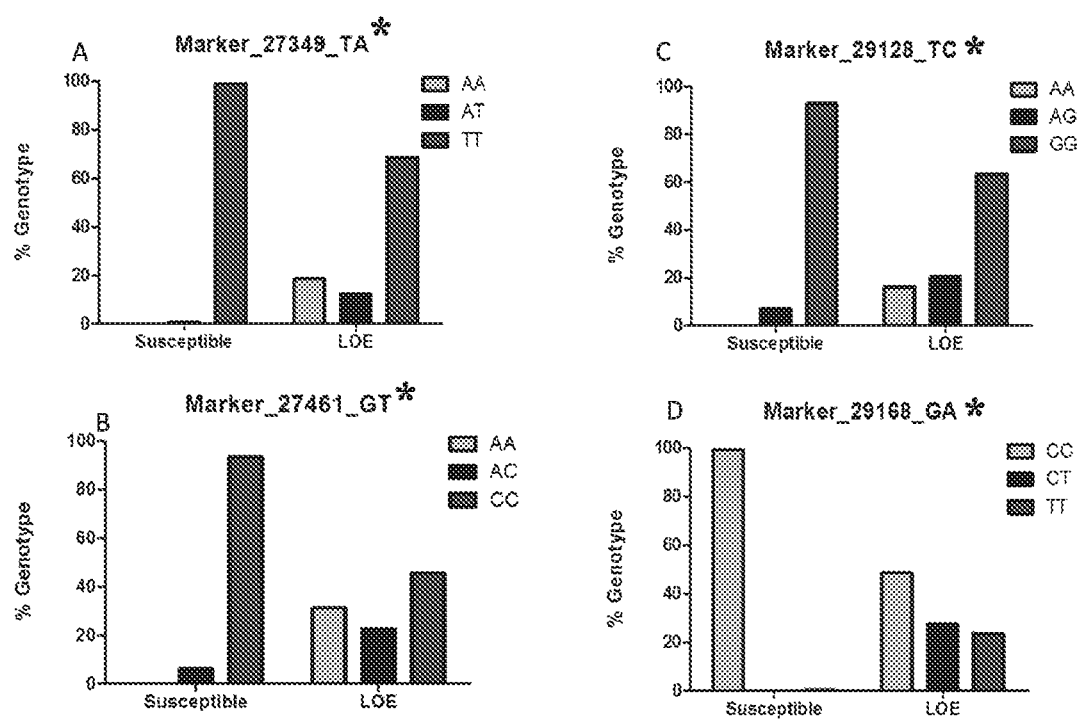
FIG. 13 illustrates the genotype frequencies for the SNP within Marker 27349 (SEQ ID NO: 49), Marker 27461 (SEQ ID NO: 50), Marker 29128 (SEQ ID NO: 51), and Marker 29168 (SEQ ID NO: 52).
Figure 14:
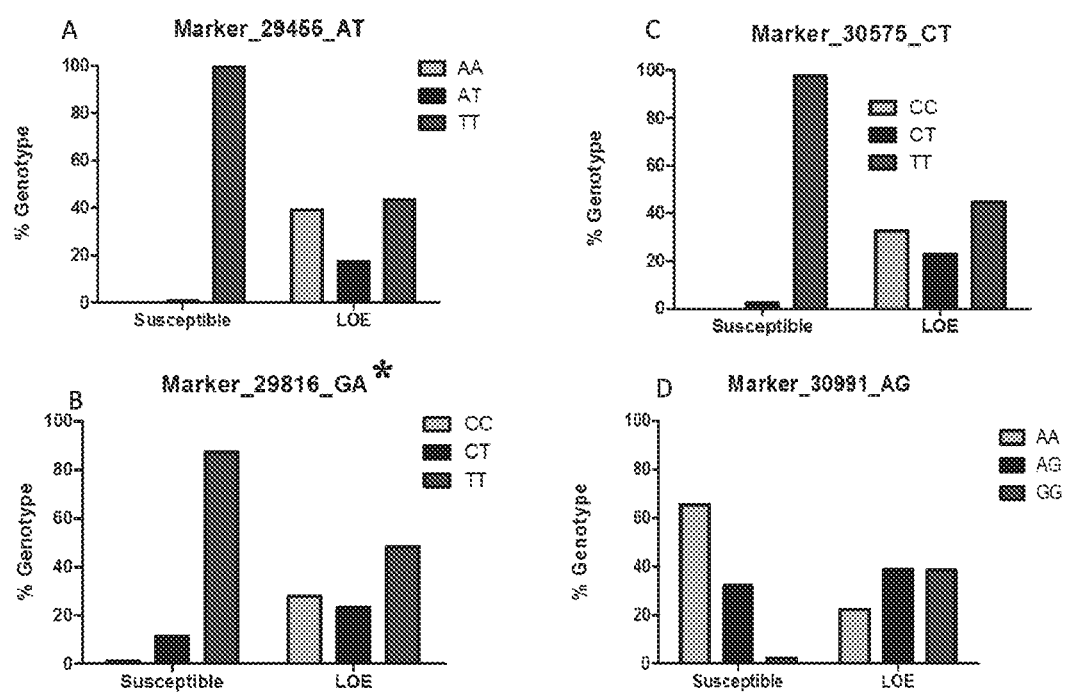
FIG. 14 illustrates the genotype frequencies for the SNP within Marker 29455 (SEQ ID NO: 53), Marker 29816 (SEQ ID NO: 54), Marker 30575 (SEQ ID NO: 55), and Marker 30991 (SEQ ID NO: 56).
Figure 15:
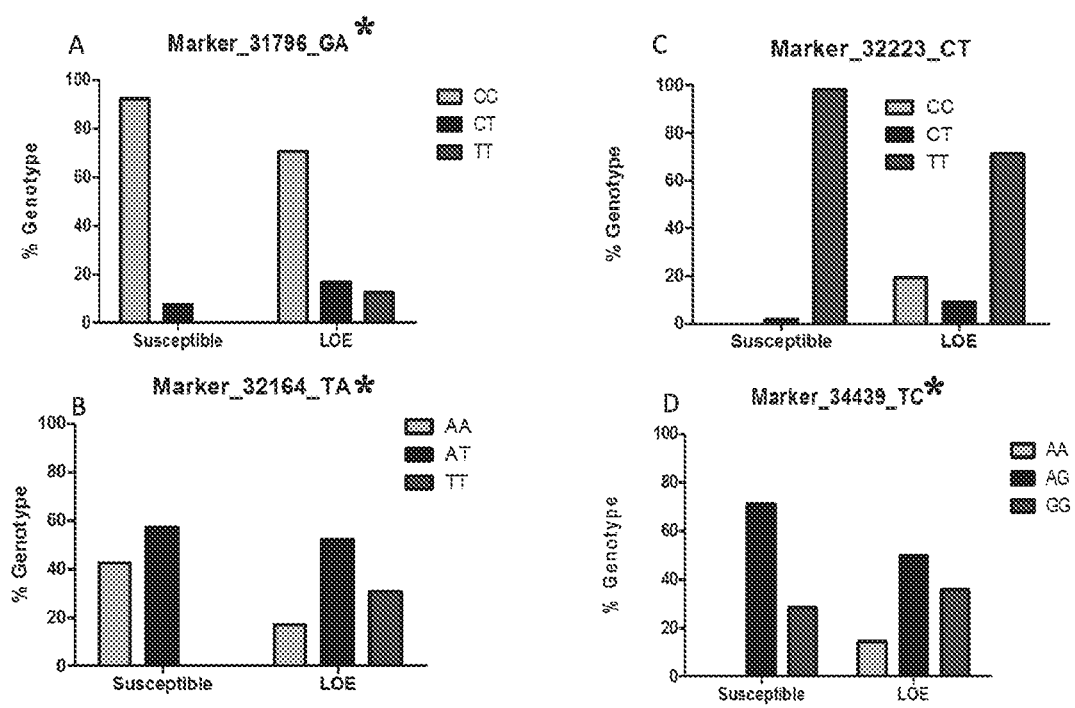
FIG. 15 illustrates the genotype frequencies for the SNP within Marker 31796 (SEQ ID NO: 57), Marker 32164 (SEQ ID NO: 58), Marker 32223 (SEQ ID NO: 59), and Marker 34439 (SEQ ID NO: 60).
Figure 16:
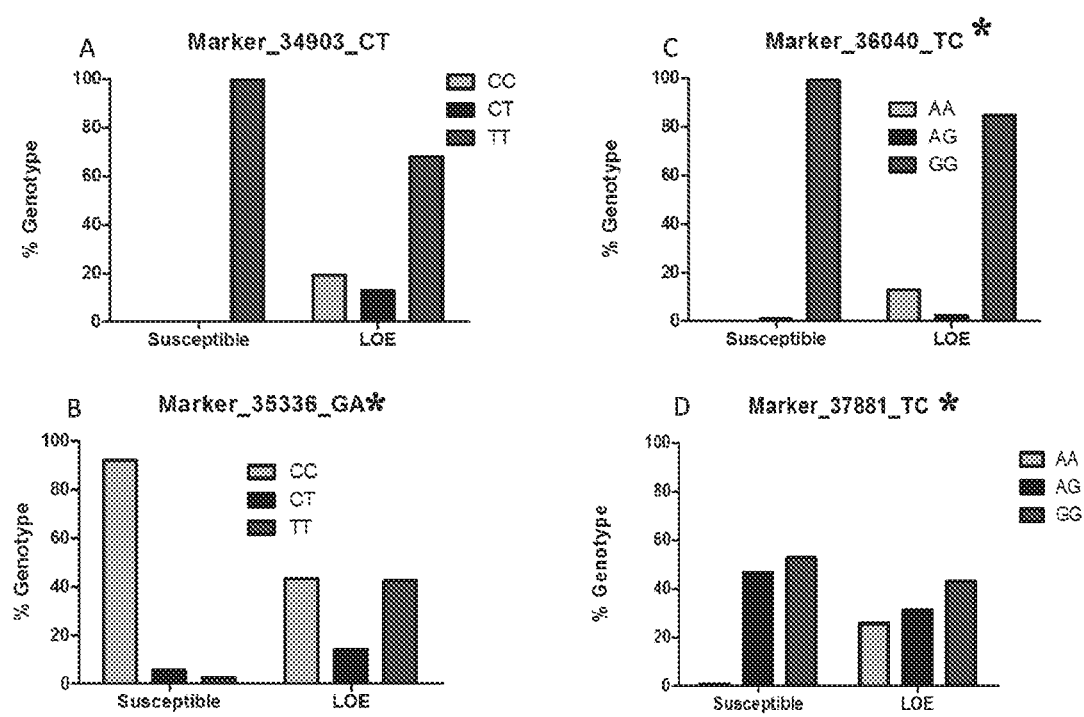
FIG. 16 illustrates the genotype frequencies for the SNP within Marker 34903 (SEQ ID NO: 61), Marker 35336 (SEQ ID NO: 62), Marker 36040 (SEQ ID NO: 63), and Marker 37881 (SEQ ID NO: 64).
Figure 17:
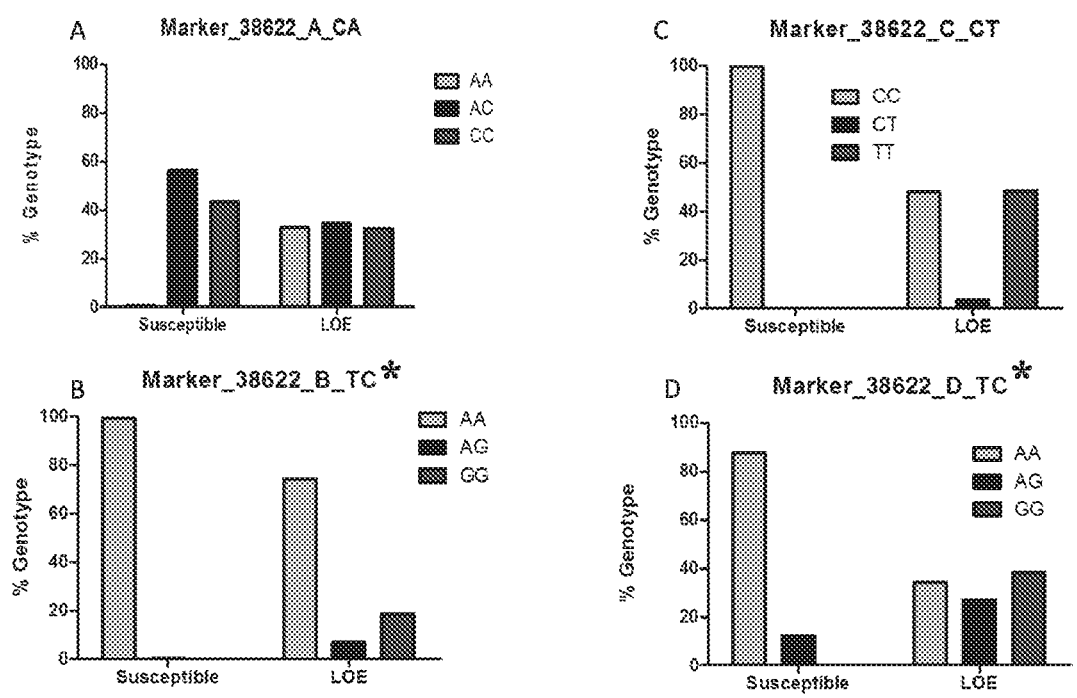
FIG. 17 illustrates the genotype frequencies for the SNP within Marker 38662_A (SEQ ID NO: 65), Marker 38662_B (SEQ ID NO: 66), Marker 38622_C (SEQ ID NO: 67), and Marker 38622_D (SEQ ID NO: 68).
Figure 18:
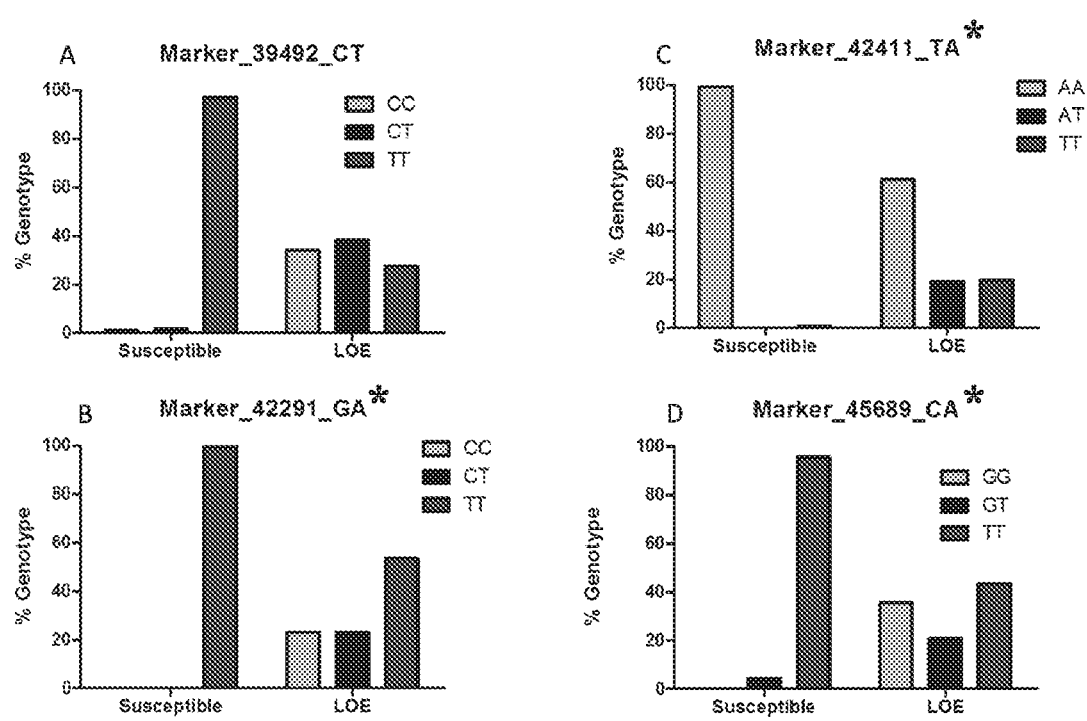
FIG. 18 illustrates the genotype frequencies for the SNP within Marker 39492 (SEQ ID NO: 69), Marker 42291 (SEQ ID NO: 70), Marker 42411 (SEQ ID NO: 71), and Marker 45689 (SEQ ID NO: 72).
Figure 19:
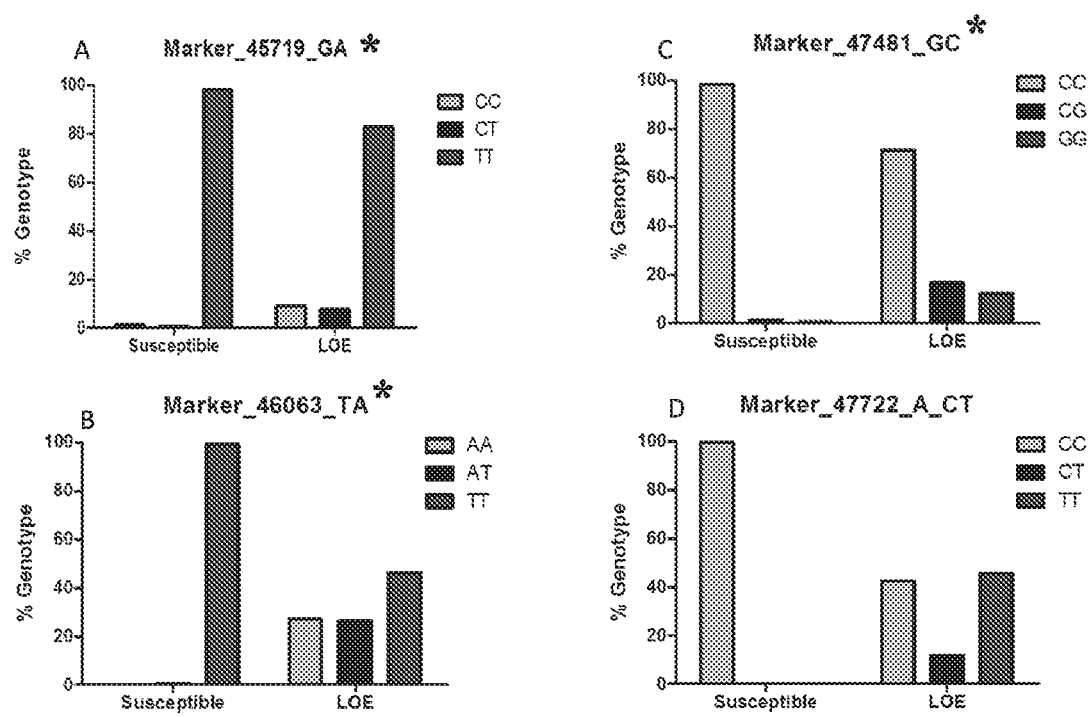
FIG. 19 illustrates the genotype frequencies for the SNP within Marker 45719 (SEQ ID NO: 73), Marker 46063 (SEQ ID NO: 74), Marker 47481 (SEQ ID NO: 75), and Marker 47722_A (SEQ ID NO: 76).
Figure 20:
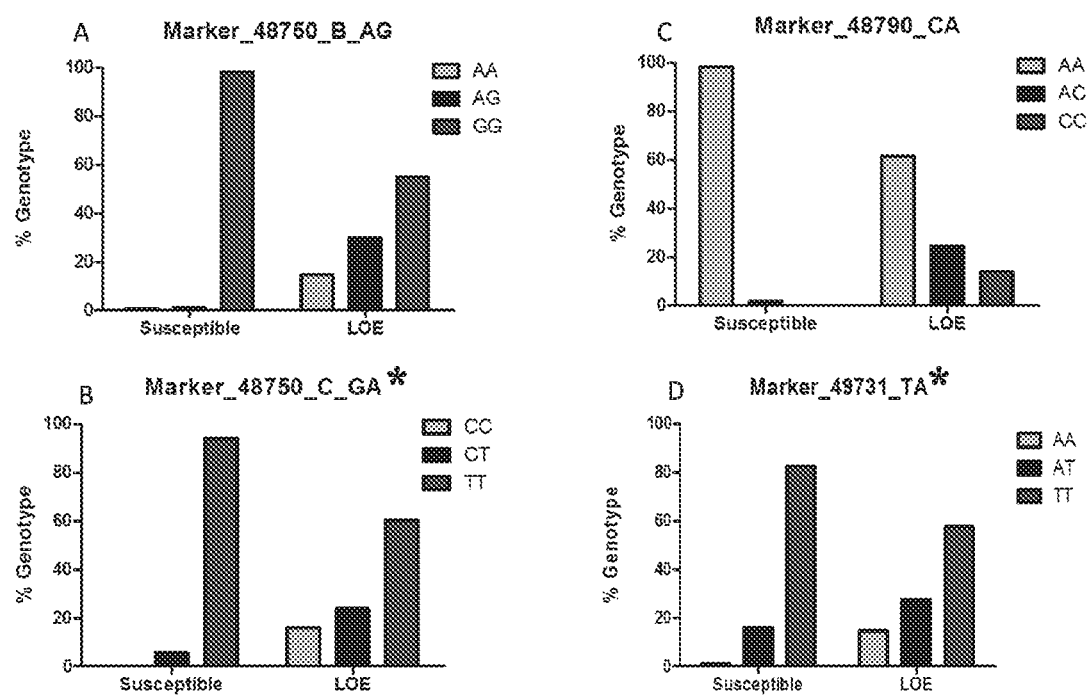
FIG. 20 illustrates the genotype frequencies for the SNP within Marker 48750_B (SEQ ID NO: 77), Marker 48750_C (SEQ ID NO: 78), Marker 48790 (SEQ ID NO: 79), and Marker 49731 (SEQ ID NO: 80).
Figure 21:
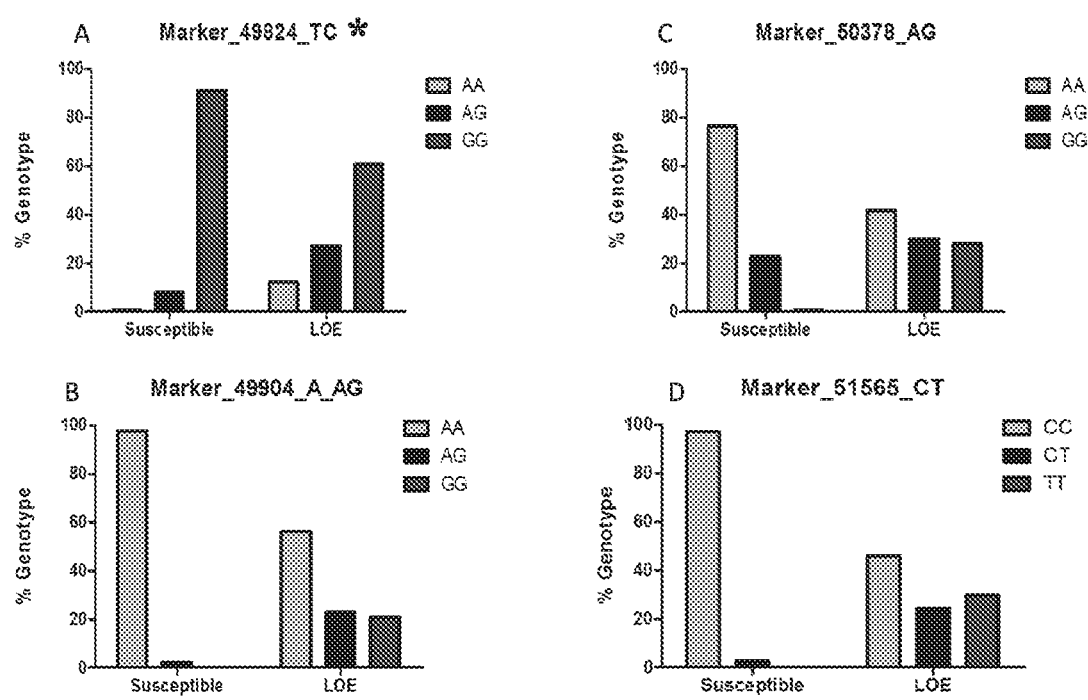
FIG. 21 illustrates the genotype frequencies for the SNP within Marker 49824 (SEQ ID NO: 81), Marker 49904_A (SEQ ID NO: 82), Marker 50378 (SEQ ID NO: 83), and Marker 51565 (SEQ ID NO: 84).
Figure 22:
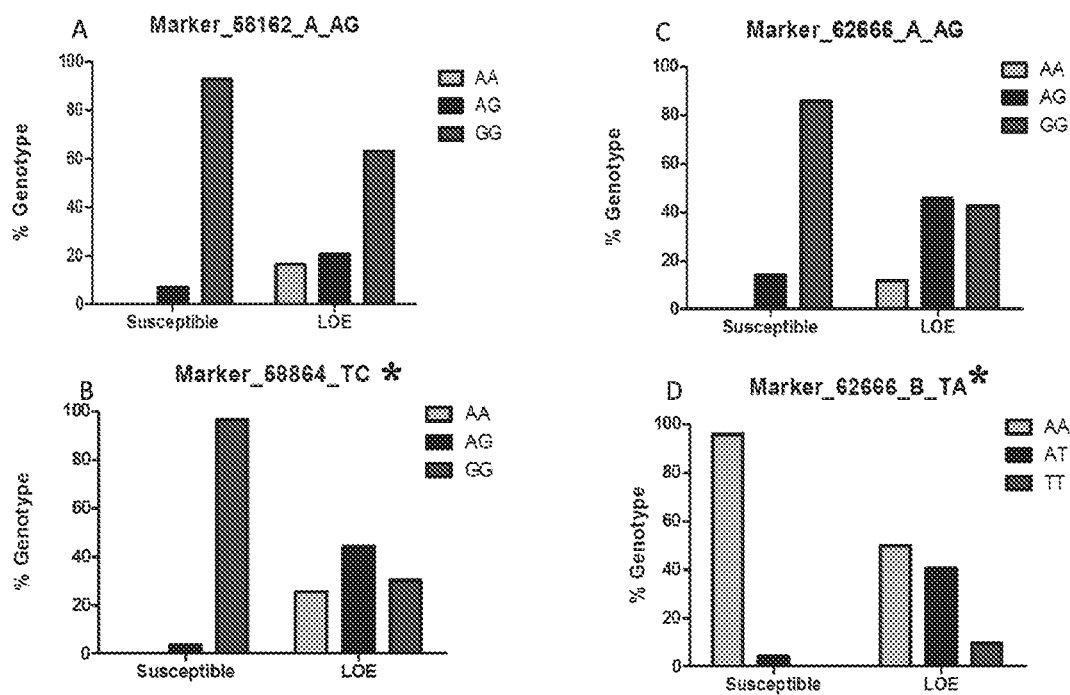
FIG. 22 illustrates the genotype frequencies for the SNP within Marker 58162_A (SEQ ID NO: 85), Marker 58864 (SEQ ID NO: 86), Marker 62666_A (SEQ ID NO: 87), and Marker 62666_B (SEQ ID NO: 88).
Figure 23:
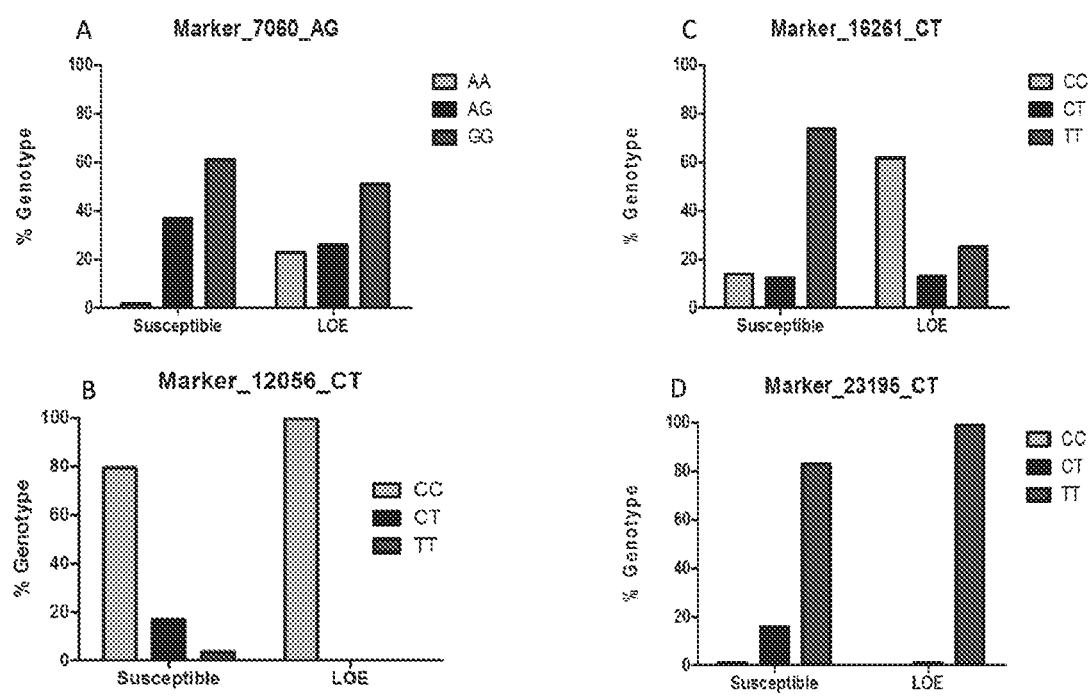
FIG. 23 illustrates the genotype frequencies for the SNP within Marker 7060 (SEQ ID NO: 89), Marker 12056 (SEQ ID NO: 90), Marker 16261 (SEQ ID NO: 91), and Marker 23195 (SEQ ID NO: 92).
Figure 24:
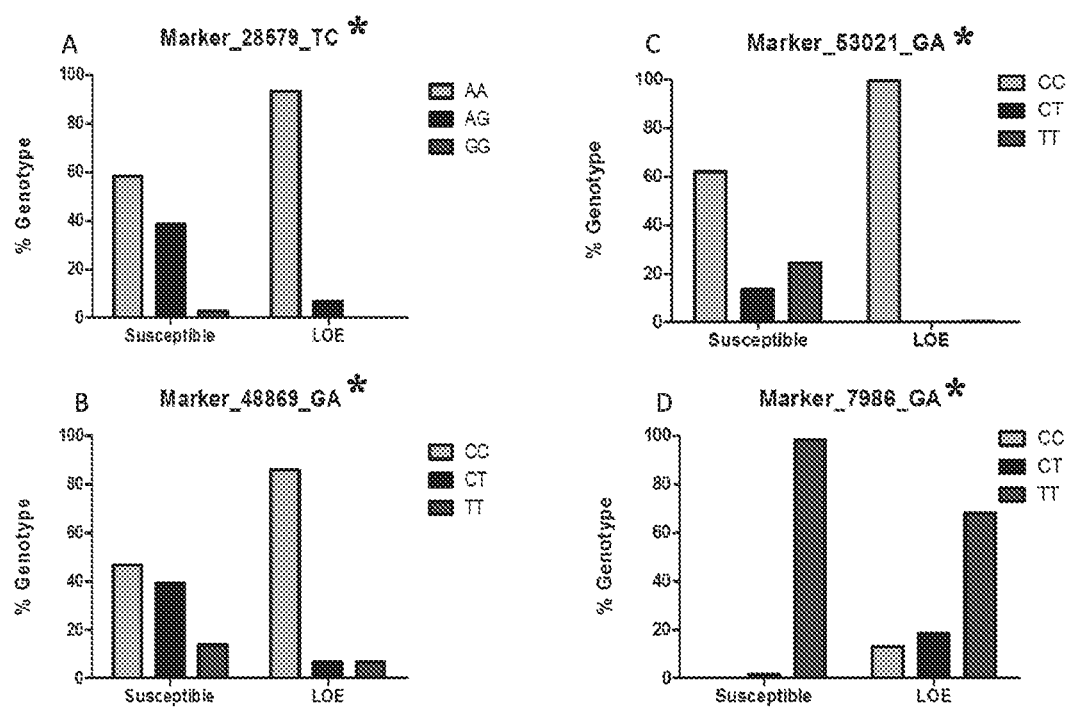
FIG. 24 illustrates the genotype frequencies for the SNP within Marker 28579 (SEQ ID NO: 93), Marker 48869 (SEQ ID NO: 94), Marker 53021 (SEQ ID NO: 95), and Marker 7986 (SEQ ID NO: 96).
Figure 25:
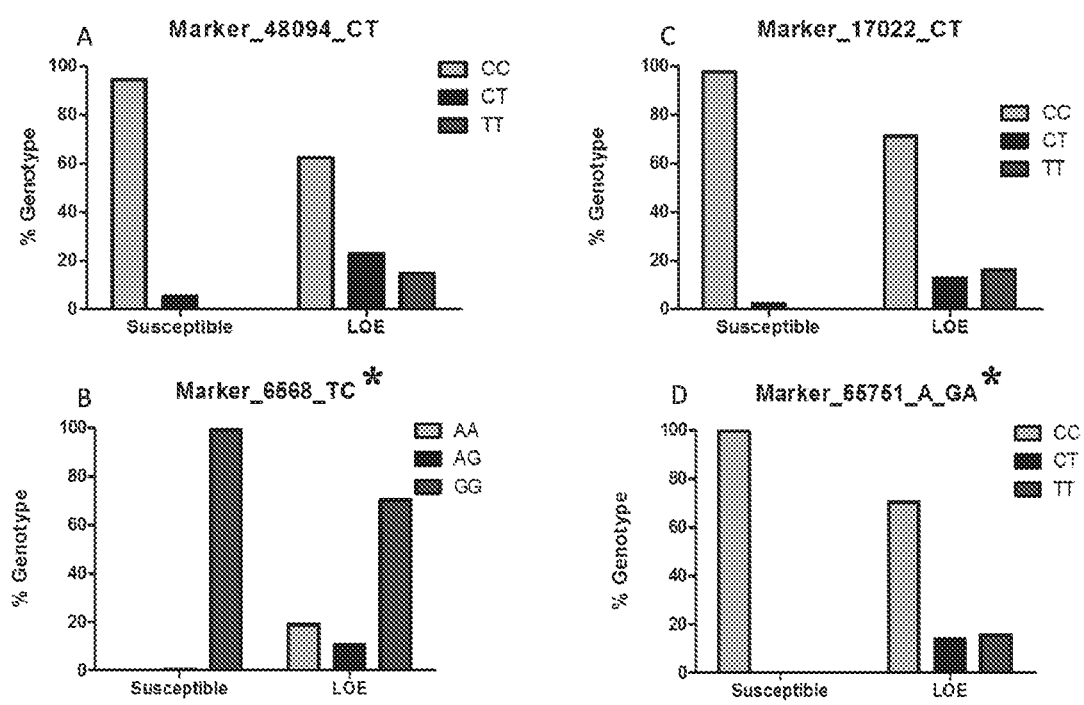
FIG. 25 illustrates the genotype frequencies for the SNP within Marker 48094 (SEQ ID NO: 97), Marker 6568 (SEQ ID NO: 98), Marker 17022 (SEQ ID NO: 99), and Marker 55751_A (SEQ ID NO: 100).
Figure 26:
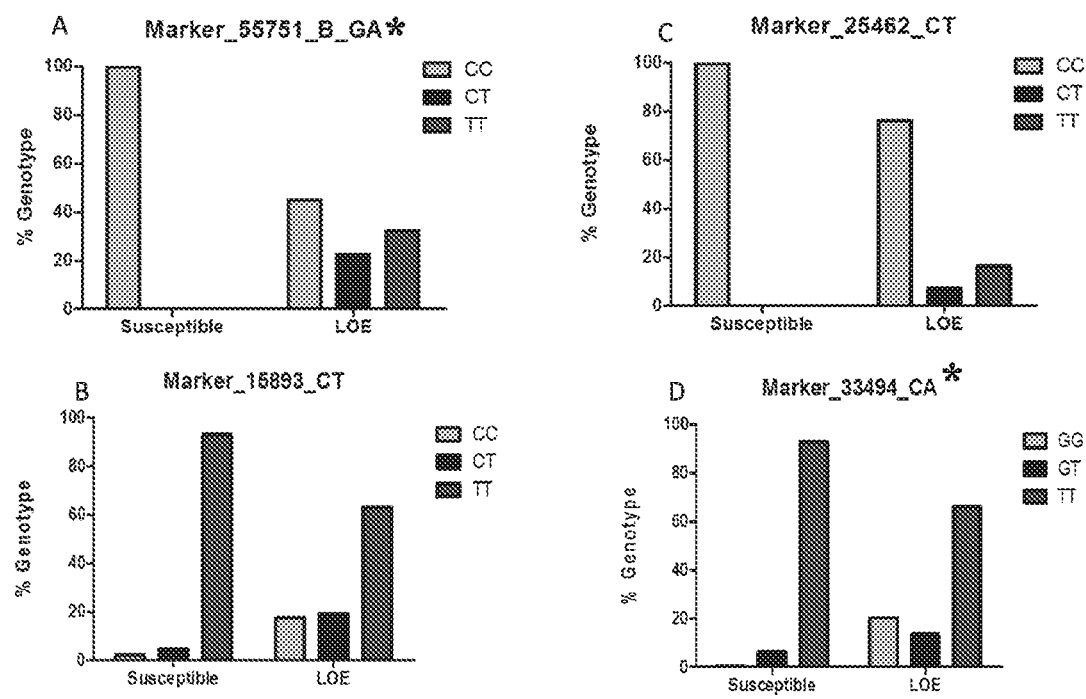
FIG. 26 illustrates the genotype frequencies for the SNP within Marker 55751_B (SEQ ID NO: 101), Marker 15893 (SEQ ID NO: 102), Marker 25462 (SEQ ID NO: 103), and Marker 33494 (SEQ ID NO: 104).
Figure 27:
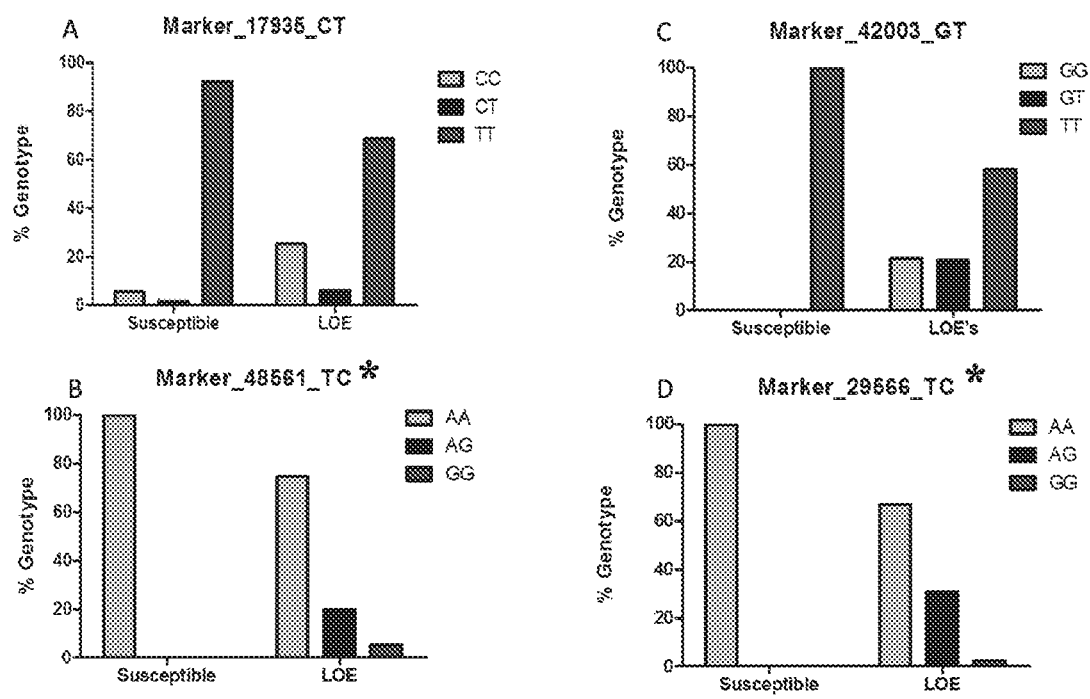
FIG. 27 illustrates the genotype frequencies for the SNP within Marker 17935 (SEQ ID NO: 105), Marker 48561 (SEQ ID NO: 106), Marker 42003 (SEQ ID NO: 107), and Marker 29566 (SEQ ID NO: 108).
Figure 28:
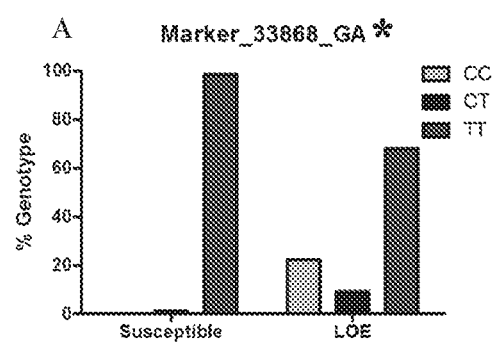
FIG. 28 illustrates the genotype frequencies for the SNP within Marker 33868 (SEQ ID NO: 109).

In one aspect, the invention relates to isolated nucleic acid molecules possessing at least 80% sequence identity to SEQ ID NOs: 1-127, over their entire length, and comprising the alternative nucleotides at the location of the SNP (i.e., polymorphic site), the alternative nucleotides indicated by the underlined nucleotide in SEQ ID NOs: 1-127, as disclosed in this application. The alternative nucleotides generally have a lower frequency of occurrence at the indicated positions within the sequences, as shown in FIGS. 1-29. In one embodiment of the invention, the genome of a nematode parasite, or a population of parasites, may contain one or more of the alternative nucleotides at the polymorphic sites shown in SEQ ID NOs: 1-127. The presence of these alternative nucleotides generally correlates with reduced sensitivity of the parasites to MLs as compared to parasites that do not contain the alternative nucleotides.

In another aspect, the invention relates to isolated nucleic acid molecules comprising, consisting of, or consisting essentially of the sequence depicted in SEQ ID NOs: 1-127.

A nucleic acid molecule of the invention may comprise a sequence corresponding to that of SEQ ID NOs: 1-127 over their length, and containing the alternative nucleotide at the SNP site (i.e., polymorphic site). In embodiments of the invention, the nucleic acid sequence may be at least about 80%, at least about 81%, at least about 82%, at least about 83%, at least about 84%, at least about 85%, at least about 86%, at least about 87%, at least about 88%, at least about 89%, at least about 90%, at least about 91%, at least about 91%, at least about 92%, at least about 93%, at least about 94%, at least about 95%, at least about 96%, at least about 97%, at least about 98%, at least about 99% or 100% identical to SEQ ID NOs: 1-127, but that was isolated from a nematode having the alternative nucleotide at the position in each sequence shown by the underlined nucleotide as disclosed in this application.

In other embodiments, the nucleic acid molecule of the invention may comprise a part of, or fragment of, SEQ ID NOs: 1-127 that also contains the polymorphic site and the alternative nucleotide at the polymorphic site. In various examples, the fragment of SEQ ID NOs: 1-127 may be 5, 20, 15, 20, 25, 30, 35, 40, 45, 50, 60, 70, 80, 90, 100, 120, 140, 160, 180, 200, 220, 240, 260, 280, 300 or more nucleotides in length.

A nucleic acid molecule of the invention may be derived from a *D. immitis* nematode containing one or more of SEQ ID NOs: 1-127 as disclosed in this application. As used herein, "derived from" may refer to a nucleic acid molecule that was isolated from a natural source, e.g. a *Dirofilaria immitis* nematode. It may also refer to a nucleic acid molecule that is man-made, e.g. recombinantly or synthesized on the basis of a nucleic acid molecule isolated from a *D. immitis* nematode.

Detection of SNPs

SNPs may be detected by any method that can determine the identity of a nucleotide at a specific position in a genome (e.g., polymorphic site) and that allows for comparison of the identities of nucleotides at the specific genome position between individuals or populations of individuals. Differences in the identities of nucleotides at a specific position may be indicative of a SNP.

A variety of methods may be used to detect SNPs. In one example, hybridization-based methods can be used. Hybridization-based methods generally rely on hybridizing complementary DNA probes to the site containing the SNP. In one method, dynamic allele-specific hybridization (DASH) relies on differences in melting temperatures resulting from mismatched base pairing. By designing probes that differentially hybridize based on nucleotide changes in target genomes, SNPs can be detected.

In one example of a hybridization-based method, molecular beacons can be used. Molecular beacons are single-stranded nucleotide probes, with a fluorochrome at one end and a fluorochrome quenching molecule at the other end, that can form a stem-loop structure and place the fluorochrome and quenching molecule in close proximity to one another. In absence of hybridization of a molecular beacon to a genome region, the fluorochrome will be quenched, due to its close proximity to the quenching molecule. When the molecular beacon hybridizes to a genome region, the fluorochrome generally will not form a stem-loop structure. Under these conditions, the fluorochrome will fluoresce, due to the increased distance to the fluorochrome from the quenching molecule.

In one example of a hybridization-based method, oligonucleotide microarrays, which are high-density arrays containing hundreds of thousands of probes, are used for hybridization to SNPs. By comparing differential hybridization to redundant probes, it is possible to detect SNPs.

In one example of detecting SNPs, enzyme-based methods may be used. In one example of an enzyme-based method for detecting SNPs, restriction endonucleases are used to digest a genomic DNA. By determining the fragment lengths that result from the digest, it can be determined whether certain sites within a genome fail to be cleaved by the endonuclease due to a nucleotide change (e.g., alternative nucleotide) in the sequence recognized by the endonuclease.

In one example of an enzyme-based method for detecting SNPs, PCR (polymerase chain reaction)-based methods are used. In one example of this, two primer pairs are designed such that only one of them will function to amplify a site containing a SNP, depending on whether the SNP is present. The sizes of the amplified products are distinguishable, therefore informing which primer pair functions, and whether the SNP is present.

In one example of an enzyme-based method for detecting SNPs, nucleotide probes are designed to hybridize to a genomic site and produce a mismatch, whether or not a SNP is present at the specific genomic site. An endonuclease (e.g., Flap endonuclease) that cleaves one of the probes, depending on whether a mismatch exists, is used. Using fluorochromes and quenching molecules, attached to one or more of the probes, SNPs can be detected.

In one example of an enzyme-based method for detecting SNPs, primer extension is used. In this method, primers are hybridized to genome DNA immediately upstream of the SNP. DNA polymerase is then used to extend the primer in a mini-sequencing reaction. The sequencing reaction determines the presence of a SNP.

In one example of an enzyme-based method for detecting SNPs, the 5'-nuclease activity of Taq DNA polymerase is used. A TAQMAN™ assay is performed concurrently with a PCR reaction. The method is set up so the PCR reaction will extend through a site containing a SNP, and release a fluorochrome from a probe hybridizing to the SNP region, depending on whether the probe contains a mismatch due to presence of the SNP.

In one example of an enzyme-based method for detecting SNPs, DNA ligase is used to ligate two probes, one hybridizing to a SNP site in a genome, depending on whether the SNP is present, and a second probe hybridizing adjacent to the SNP site. If both probes hybridize to the genome without mismatches, ligase will connect the two probes, which can be measured.

Other methods of detecting SNPs exist, including for example, detection of single-stranded conformation polymorphisms, temperature gradient gel electrophoresis to detect duplex mismatches due to SNPs, denaturing high performance liquid chromatography to detect mismatched duplexes, high resolution melting analysis, use of mismatch-binding proteins, and others.

In one example of detecting SNPs, a biological sample comprising a *D. immitis* nematode may be obtained from a subject. The subject may be, without limitation, a dog, fox, wolf, coyote or cat. In the context of the invention, a biological sample may be any sample (e.g. bodily fluid, excrement, organ, tissue, etc) from a subject. The biological sample may be from a subject that is known to have, or is suspected of having, a *D. immitis* nematode infection. The *D. immitis* nematode may be isolated from the biological sample with standard separation methods and techniques.

A nucleic acid sample may be isolated or obtained from a *D. immitis* nematode prior to use. Methods of isolating nucleic acids from organisms and tissues are known. Such methods may include, but are not limited to, traditional DNA extraction, with proteinase K digestion followed by phenol chloroform extraction, sodium hydroxide extraction, and physical disruption, followed by purification, e.g. by cesium chloride centrifugation or high performance liquid chromatography (HPLC); or the use of commercial kits. A skilled person would appreciate that different approaches may be used to isolate a nucleic acid sample from an adult *D. immitis* nematode in comparison to a microfilaria. In an embodiment of the invention, the nucleic acid sample comprises genomic DNA.

The nucleic acid sequences of the nucleic acids from the parasite may be determined using any one of numerous methods known in the art. In some techniques, sequences of separate pieces of the genome are assembled into linear whole genome representations of the parasite using computer-based methods. In one example, massive parallel sequencing may be used. Massive parallel sequencing (also called "next-generation sequencing") may encompass various high-throughput DNA sequencing methods. One such method is the HiSeq2000 system from ILLUMINA®.

Through comparison of sequences from separate parasites or parasite populations (e.g., comparison of a consensus or reference genome obtained from parasites sensitive to MLs with a consensus or reference genome obtained from parasites resistant to MLs), presumptive SNPs can be identified.

The presumptive SNPs can be analyzed further. In one example, high-throughput SNP analysis using multiplex PCR and MALDI-TOF mass spectrometry (SEQUENOM®) analysis) was used. Generally, this system uses extension of an oligonucleotide primer or probe using chain terminating nucleotides to product different sized PCR products for each allele of a SNP. The different sized PCR products are analyzed using MALDI-TOF mass spectrometry.

Disclosed SNPs

In one example, genetic markers from *D. immitis* include the sequences below (SEQ ID NOs: 1-109), where the underlined nucleotides (i.e., the polymorphic sites) indicate the nucleotide position within the fragment that correlates with resistance to MLs (i.e., the alternative nucleotide). In these sequences, the nucleotide at the underlined position is generally different than the nucleotide found at this position in organisms that are not resistant to MLs (wild-type). In the sequences below, the nucleotide underlined in the indicated sequence is the alternative nucleotide which correlates with resistance to MLs. In the heading for each sequence, the nucleotide change from wild-type to the alternative nucleotide (alternative correlates with ML resistance) at the polymorphic site is shown (e.g., C in wild-type and A in the alternative sequence is designated as C→A). The genotype frequencies for each SNP at the polymorphic sites are shown in FIGS. 1-28. In FIGS. 1-28, for markers designated with an asterisk (*), the graph presents the genotypes of the reverse complement sequence, as compared to the nucleotide sequence presented in SEQ ID NOs: 1-109.

```
MARKER 617 (SEQ ID NO: 1): C→A
AACATAAACATATTGAACTGAATCCTGCAAACAGTTCTCTTATAACGTGAACCATAACTAAATTTAGAGAAAATATG

AAAAAGAAAAATAAGTTGCTTTTGCTCGTGCACCAACTCTAATACCCAGGAAATCAAGAAGTGATAATGAGTAATGT

CATCATTAGATTCAGTAATTGGTGACACTATCAATATTATTATTATTATACTTAAAAATACGACGACCACTTATCGT

AACTTAAAGCATGCATAATACGACTGTCATCATATTACATTTCTTCAAGTTCGTATTGGACAAGTGATT

MARKER 714 (SEQ ID NO: 2): C→T
GACAAGCGTTGACGGGAGAGACGATATAATAATAAAGAAGGCATTGGGTATCAGAAGGCACAATCCAATTATAAATG

CCAAGGCAAAATGAATAAAATTTATGCTGACGATTTGATCAATTACGAAGAATTTCCGATCGGCTCGAATCTTTGTT

TGTATGTGCACTACTGTTAACTTAATCTTTGTTTTATATACTTTTGCGTGTCATATATAATATATTCATGTCAACTG

ATACGTTATGATGTTTTTTTGTAAATTAAGTTGATCGGAAACCTGAAGTCTATTTCAAATTTAAGAAAT

MARKER 814 (SEQ ID NO: 3): T→C
TTTTAGGAAAATGGTGACTGTAGAGAGATATTATCGGAACGACAAGGTCCACTTCGAACGGGTCTTTTATTGTCGAC

GGATTGTGAACCAAGTTTTGGCATTCATAATGACAGGTAGCTATTTTTCCATCATCCCATTTTTGTATTAGTGCAAG
```

-continued

CAAGTCATGAGTCGAAAGAAAATCTCAAAAGAAAAAAATGAAATTTCAGGTTCAAAGGACTGCGTCCATTATTCGCA

CTGGTTGATGAGAACGTACAGATTCCAGAGCGGCAATGCTGCACAGTATCTTTTGTTTCACTTCTGAAT

MARKER 887 (SEQ ID NO: 4): C→T
TCGATTAAAAATTATCATCGATAAAATTCTAAAATTTATTTTAGTAAAATTATTATTATTTTGATGAATAAGTTAAC

AAAAAAATTTTAATAACTTTTTGATTCGCCAAAAATCTAATTCGTTAAAAAGTCGTTCCAAACAGATATCGCTTGTT

CGATGAAAATGTCCGGTTGTTAGAAAATCATAAATTGGTTCAAATAATTTTCCAGAACGTTCGAAAAAATATTCCCT

TGTATCGGATAAATAACCATTACAATTTTCCACTCGTGTTGCATGTGTTTCTCGACAAAAATCAGCTAA

MARKER 1514 (SEQ ID NO: 5): T→C
TCAACAGAAATCGAGATTCCAAAAAGTTTCCTACAAATACTTAATTATCAATGGATATTTAGTTTTGTTATCTGTTA

TCATAAGTTCTGCTTCTTACACGATTAAAAATGTCCAAGAATTTTTTACTATTCAAATGAGGGAAATAAAAAACCAA

TGCCAATAATATCCAGAAACTACATACATCTTTCTTTTTTCGAAGCTCATCTATTCCGGCCGAAAACAATGAAGAAC

ATTAAAATTCTTAAAAGATAGTCTTAGCCTTTTCCTTGACCACTATCTTAACTGTCAGCGCTAAAATGT

MARKER 2557 (SEQ ID NO: 6): T→C
AATAGTCGTCTCATTACTTTTTGACTTTTATAATTCGAGAATCTTATGTAGTCCTTCACTTTACCCTTCTTCTGTCG

AACTAAGAATTACAGCATTATTTTCGAATTTAATGTGTAAAAGACAATAGCAGATTTTGTAATTTTGTGTTAACCTC

ACTTTATATTTCGCTTCATATCGTGACAGAGAATTACTATTTCAGAGAGTATTACTTGTCACCAGAGAATCTCCAGA

AAGATTTTTATTTACGTCGGAAAATGGACAAAAATGGTTTCTTATCATTAGCACTGATAGCTAGTTTCC

MARKER 3367 (SEQ ID NO: 7): G→A
TATCTCTTGTTGTGTGTTCTGCATTGTATCAAAGTGGGTAAATTTTGCTTTAGACGTTGACTTATTGTCTTTTTTAA

GTTATATTCTAGTCCATGTTTTTCTCTTTGCAAATATTTTTTTCCGCCGCCTATGATTCATTGTTTTGTTTGTAACT

CTCTATTAAGTTGCTTTTAGTTTGAATTGTATCAAAATTTCAAACATTTAAAATACGCACTAGCACTATTTTTTCTT

ATCTCAATTAAGCGAATCCCGGAACAAGATTTAATCGATTTCCGAATCACAATTAAATCACTGGAAAAC

MARKER 3488 (SEQ ID NO: 8): T→C
ATTTTCCTTAACAAATCATTTTCAAACGAAAAACATTAAAAAGTGTTAAAATAAAATGGTGATATTGATAAGAAAT

TAATTCAACCTGCATATCAATTCTTGTAGCGGCCATTTTCTTAGCAAGTTCTATAGCAGCTCGATCCATATCACCTT

CTTGCTCTAATGTCAATTCCGGTTCCGGAATTTTTTTATTTTGCCATTCTTCATCTTTTTTTATTTTTTACTGAT

ATAGCTATAGACCCTTTCTCCCGTGCATGCCTGTAGGCCTGTTCTGATATACAGGCTTGTGAACCACTG

MARKER 4553 (SEQ ID NO: 9): C→T
TTCTGGGGTAGTTATACGGAAAATTAGACAATGAAGAGAATCAAAAAACATGCGATTTTCAAACAGAGGAACTTTGG

TACTTTTGCCTCGACTTACTTTATTTTAAAACCCATACAAAATAAATGTTTCATTTGATTGATATTGTCGTACTAAT

AATTAGAGCTTCAACATTAGGATTTTAATAACCTTCAATTTATTTCAGAATTTAAGAAACTTACGTATGGATGGAGA

AAATATAAAGAATGGCGATGACAAATAAGATTTGCTATGAAAAAACTAATGCCACAAGATCCGAATGCA

MARKER 5266 (SEQ ID NO: 10): C→T
TTTATGAACAAAAATAATAAAAATTAGGATAACAGATATCAATTTCTTTTAGCTATAAATATACGCTTCGATTGAAA

AAAGCTTTCAAATTATAATTAAGGCATACGTTACGATATAGACAATTAAGTCGACATTAATTATTTGAAATATTTTA

AATTTTTTTCTCTTTCTTTTTTTCTATTCTCTTCCAAAGTGTCAAATAGTTATGAAATTGTCAGAAGCTAAAATGAT

AATATTATTCAAGTTTATTACCTAATCTTTTATCACCTCATTTCTTATCATTTATCTGAAAATCTAATC

MARKER 5365 (SEQ ID NO: 11): G→A
ATGTTGAATTTTTAATGAAACTTTTTCGGTGCATAAGCATTACAGATCTGTAAGCTGTGCAAACCCTGTTTCTTTGT

AAATTGAAACAAAGATCATTTATTGTTTCCAGCGTCGATTTGACCTGGATAAATGTGGTACCAAAAGTAGATGACGA

GAGGTAAGTGCAAACAAAATGCACAAAAATGATTTTGATGCACTCAAATCATTTTTAAGTTTTGTGCAATTTTCCAT

TTTATAGTTTCGTGATCGGTTGTTATTCATCAACTTGATTTTGTTTGTTTTTTGTGACTTATATTTCAT

MARKER 5667 (SEQ ID NO: 12): G→A
TTTGACACTTTCAGATACCTTACAAACTCATCTCCAGCACCCAATTTACAATATCGCTGCCTAAATAAAGAATTTAT

TCGGATATGAGACTGTAGTTTTCATTCCGTACCAATCATAGTAGAACAGATCTATAGCATGGTGTCCTACTAAAGTT

GTGACTGGCTATTAAGTATGTGGGTGTTTTTACGTGTGCGTGGGTGTTTGTGCGTGTGTGCGTGTGCGTTTCTGCAC

ATATTTTCGTGCGCGGTGTCTGTGTGTGTCCGTTTGTATATGCCGAGTGTAGCTGTGTGTATGTTCTTG

MARKER 6568 A (SEQ ID NO: 13): G→C
CACTCATAATATACCTGTCAACAAACTCAGAAATCTGAATAAAATGACGCAAAAATGACAAAAACATTTTATCAACC

TTTTCTTCATCACTCCCCCGCATTTCCAATTTTCTTCCAAACTGTTTTTGTCGTGCTACAAAGTCATCAGCCACTTC

ATTTTCTTCAAGATGGTTCGAGACGCCATTCTTGGATTCACCCCTTATTTCAACTGTTTCCGAAGTCCCAGCAGTTG

AAGCTGAACCTAGCATTTATATCACCACCCGATGTCAAAAAATGACAGCGGTCAGAGAATACGACTTCC

MARKER 6568 B (SEQ ID NO: 14): G→A
GCTAGGTCAACAGTTGGTTTATTTGGACTTATACGATATTAAACATAATATCGCCTCATATACACAGAAATATCAAA

AAAACGAACACAGCTAAATCGAAGAATACGAACAAATGTTTTAAAAATTATATTAAATCTTTTAATGCTCTCTACAA

TGTCGTATCTTCCCTTTTGTCTGTATTTCTCCTTTCGTTCCACCACTGCTATTTCTCATGCCTTTGAACTATGGTTC

TCGTTGCGTCGAATTGTCCTCGAAACTGTTGTTTCTGTCGAATTACGTCGAACTGCTGGACTTTGTCGG

MARKER 7633 (SEQ ID NO: 15): T→C
ATATCTCACTTCTGACATAAATTGAAGTGGCACTGATTTGAATGAAATGATAAATAAAATAAAGACGACAAGGTAGT

GGAAAAAAAAGAGGAGAAAACACCGTTTAGTTTTGGATGCAAGCTCGAATCTGAGTTTTCTTGCAAACCGTACACT

GATCAATTTTCTTACACAAACATAAGAAAAAAAGAAGTGATTTTACTGTAGCTGTATCGTATAATTCAAATCATATA

TATATATGTTTCAATAATCTATACATTTATGTATATTTTTTTTGAATGGAACAGTGAATGATTTTAAA

MARKER 9400 (SEQ ID NO: 16): T→C
ACAAATGCCATCGGGAGAGAAATATCGTTGGCGTACTGATCACATTGGCGGTATCACTTCTTTGAAAACTCCAGCTG

GTATTGTGTATCATTTCATGCAATACGCTATTTTTGATCGAATATGTCGACGGCGTAGTGTTTCATTTTCCAACGCA

TCTTACGTTGCGTGTATGGATGATGACGGACAATTATTGGAATATCAAACACCGGATCGATTGCATTCCGTAACCTT

GAAACGTGACATATATGGGAGAGTAGTGCAAATAACTTCAGATGGCGAAAATATTTTCTTCGAATATGG

MARKER 9473 (SEQ ID NO: 17): C→G
ATAATATATATTTCCATTGATAATATTTTTCATATTATGTGATGTTTGAAATTTTCTGCAATTGCTACATTCCGATT

AAAAACTTTTATTATCCGTACTGGAGAATTTTGCTTTTTTTTGACGGTTTGTTCAATAAGTTGTCAATATATTGTCT

GCCTTAGTAAAACCTTTCTAATCTATCCGTTCGAATTGGAAGTTGAAAGTTCAGCATCATTCTTTTAGTGAGGTGTT

TAAGTTGTTCAATAGATATTATTTAGAACGATCTCAATTAAAATCTTCTGAATGATTTTATGTTTTTAT

MARKER 9858 (SEQ ID NO: 18): A→G
GCAGCACATTGCACACAGTAAACTGCAAACTGAATTAAGAGATATTGGGTTGAATTATTTCTAATTTAAAAGGATAT

AATAAATGACTTTGATGATTGTTGATTTTAAGGTATCTCGGAAGACTCCATCAGTCTCAGTGCTCTAGCAATCGCTA

TAGGTACTAAAAGAAAAGAAAAGATGTCTCGTTATTCACTTTGAAATGTACATATCAAATCATTTTGTCGTATGAAA

TTAAGTATATTATGTCTAATCGTATCATTCGAAATGAATTTACTGTCACTGTTAGAACTATTTAGGCAG

MARKER 10349 (SEQ ID NO: 19): A→G
AGAGTTCAATCGCCAAGTTGTTCTTTTTCTCGCTCGCAGAGATCAAAACGGTGTTGGCTATACACTCATTCATCAGG

CTGTGATAGACATCTCTTAGAATTTCAGTGCTTTTCTGGATGAAAACATTATTTCTCAAACATGACACTTAAGGACA

ATAGTGCGTGACTTCTTTGTTAACGTACACGAGAAAACAAAACAGATGATGCTTGTTATCTTGGTGATAAATGTGTA

TTCAGAATAATGTTATATATCTTTGCGTGACAAATATCATTTCGTTATACTTCGGATACGCCTTTTTAT

MARKER 10520 (SEQ ID NO: 20): A→G
AACTTTACTTGAACTTTTTTGGTGTTCAATTTTGAATATTATACCAACCATTCAGAAGACTGTATATAGAAATGAAC

CTTCAAGAATTAATCGAAATTTTTATTAAAATCTTTTATTTGAATATTTCATTATTTAAACTCATTACTATTTGCAG

TATATTATTAGATCTAATGTAGAAAAAAAAATCAGATGGCAAAAATAATATCATAGGTTTGTTTTTAAAATTCATTG

CAAAATTCAGTGCGCCGTTCCAGTCGCTCGTAATTACCCTATCCCTGAGCTTTACAAAAAGAATGCTTT

MARKER 10678 (SEQ ID NO: 21): A→T
AGGTATCTAGATAGCATAATAAATTACTACACAAACCGATGGAAACGCAAGTTTGGCGTTGCGTGTTGATACAAAAT

ATTAGAGCCAAGGATGGTATCACATGTAAAACTGCAATTTTGCTATTTGTTTAAAGCAAATAAGAAATAAATATTTC

-continued

GTTCTTATTCTTTAATTTATTTCATCAGATGGCTTTGTTATACCATAATTGTAAATCTGTCATATCTTAATTGCGCA

ATAGCCCAAGATTCTTGTATATTCTTACATTTCACAATTTATTTTCTTATTTCTAGTTTTAGAATTATA

MARKER 11676 (SEQ ID NO: 22): A→G
AATAGCTACTCACAGCTTAAGTTAACTAATGGATTCTTGAATTTATTTAAGCGTGTAGTTAAGCGATTAATATGATG

GATGCCCAGAATCGCTTTGTCTTATAGTTTTGTCTCGACAGAAAGGATGCATTGTTGTCTTGAATTTGTTCAAGGGA

AAATTAAATAGGTTTCTTTCAATGACTCCTATTAAATTTTTTTGAATTTAGGCTTGCATTGCGTGTTCTGATCCACT

ATTAGCACGTACGGGTATCGCAGTGCCATGTGATGCAGCACTATGCAAAACCACCTCCATGTCACTTG

MARKER 11933 A (SEQ ID NO: 23): A→G
TCTGTTGTAAGTTTCACAATCCAGTTAATTTAAGCTCAGCTTATTTGAAATTTTCAACAAAATTACGAAAATTACTT

TCTCGGTTCATTTTTTTCAACCACCAAATATTTAGCATAATTGGCCTGAAATCGTCAAAGTTTACAAACTTTTGTTC

AGCAATCTTCTCTTACTCTTACAATAAACATGATTAACTTGTCGTCATACCAATCTCGTTTATAGCAAATTCTTTTC

AAAAAAACATTGCTACAAATTTTATATCGCATCATTTCAACACGCATAATTATTTTTCATATATGAAAA

MARKER 11933 B (SEQ ID NO: 24): T→C
TTCACAATCCAGTTAATTTAAGCTCAGCTTATTTGAAATTTTCAACAAAATTACGAAAATTACTTTCTCGGTTCATT

TTTTTCAACCACCAAATATTTAGCATAATTGGCCTGAAATCGTCAAAGTTTACAAACTTTTATTCAGCAATCTCCTC

TTACTCTTACAATAAACATGATTAACTTGTCGTCATACCAATCTCGTTTATAGCAAATTCTTTTCAAAAAAACATTG

CTACAAATTTTATATCGCATCATTTCAACACGCATAATTATTTTTCATATATGAAAAACCATATTATAA

MARKER 12716 (SEQ ID NO: 25): A→G
ATTAACTCTGAACCCAAAGACTGTTGGTTAAAATAAAGATCTATTTTAGTTATACATCTAACATTAAAGGTTTTCGT

ACGGAAACAAGTAGGTTTGATAATTTTCATGTAACTGTAAAGAACACCTGTGAAAGGGATCAGTAAAATTTGGGGGA

TGTAGCACGGAAATATGAAGCTGAGTGTTTTGTACCCAAAAGTTTTTCAAATCTGCGAAATAACGAGAGGTGTAATG

ATCGTTTTTAACCAAATTTTTTGATTCTAATCCTTCCCACAGTTTTGAAATTCAGTAAGCATTTCTTTT

MARKER 12925 (SEQ ID NO: 26): T→C
TTGCAACAAATCAATAATAAAAGACTTGCGGCTAACAATATATTTGATTCTTTTTTACCGTTATTATTATGACAGGT

AATAATAGTATTACAAGCATATTTGTAGGTGTCAATTTTTTCAATTCAAATTTTCTTAATTCATTATTTCTTCCTTT

CCTTAATAAATAGTCTTTCCATTTAAGAATTAACTTTTTGAAATCTTTAATGAGAAGACACAAAAGATTCCGGATAA

TTTTGCATCATCTTTTCTATTTCGCGTTAGTATTTTATGTTTTCAACAGATTTTTATGATTTAACTATA

MARKER 13063 (SEQ ID NO: 27): C→T
GATAAAATGGGTTCTTGTCAAGCTCATTTGGCATATCTTCGTCTTCTATATTTATATCCTTTAATATCTTCTCTTTT

TTCAAATTTTCCTTCCCGACGTTTTCCATATCGACCTCTTTCTTCATAAATTTATCTTCCTCATTTGCCTCATTTTT

TGACTTTTCATCCGTTTCATCCTTATTTTTCTTTTTTTCATCTCCTATTTTACCTTTTCCTTTATCAACTTCTATCT

TAACTTTCTCAATGTTTTTTTATTTTCTTTCATCTTTTTGTTTTCTTCTATTGACATACTATAACAAA

MARKER 15000 A (SEQ ID NO: 28): T→A
TTTTACGAACAATTATTTCATAAAAGATTCGTATTTTTGATTAGTTTTTAAGAATTTTTTTTATTATTTTTAGCCA

ACAAATATATTTTTCAAATTGTTAAATTTGAAATTATAAATTTCAACTAAAAAAAAGCAAAAAGCTAAGCCAATAG

AAATAACATACATGTGTAATATAAAATATAAAGTATTCGAAATGAAAATCAAAGTTTCATAACAAAAAACAAAAAAT

ATTCTAACCTTTTAGATTTCATCAAAACTTCACTAAAAAGTTAAATTTAAATTTTCAAATTGTTATACA

MARKER 15000 B (SEQ ID NO: 29): A→G
CGAACAATTATTTCATAAAAGATTCGTATTTTTGATTAGTTTTTAAGAATTTTTTTTATTATTTTTAGCCAACAAA

TATATTTTTCAAATTGTTAAATTTGAAATTATAAATTTCAACTAAAAAAAAGCAAAAAGCTAAGCCATTAGAGATA

ACATACATGTGTAATATAAAATATAAAGTATTCGAAATGAAAATCAAAGTTTCATAACAAAAAACAAAAAATATTCT

AACCTTTTAGATTTCATCAAAACTTCACTAAAAAGTTAAATTTAAATTTTCAAATTGTTATACAATGAT

MARKER 15709 A (SEQ ID NO: 30): T→C
TCAAAGACAAAATGAAGAACTTAACAAAAAAAAGGCCAATAAATAAAGGCTATTTCGTGAAAAATCTAAAAAAAAAA

AGATCTGTTCCTTTCGAATCAAGTGATTCTTCCTACTACATTCGTGTTGTAATTCTTACTTGTATACAGTCCCCAGT

-continued

TTTTCGACGATAAAAAACATTTCGATAAGTGAGTTTGAATTAATTGAATTTTAAAAGATCATAAAAATAAAATCAAA

ATAAAAAGACCAAAATTAAGTCTGATAATTCCAGAAAACACAATAATAAATATACAATAATAAAAACT

MARKER 15709 B (SEQ ID NO: 31): T→A
AAATAATTCACTAATTTCTCATCATCAAATTATTTCGTACAATCGATAAATCAACGATTATAATAGCGAAGAGAATG

AAAATTAATGTGGTGCACAGTATACGGACCCCATATACAATGTTCAACAGAGATGAACATTTTTTTTCTATTAAAGT

TTTCTGTTCGGCGAAAGAAAGACACTTTCTAACGATGCTTTCCTCCCAACTCCCCTTGCAATGATAGAGGATGCAGC

CAAGATTCGTCGACTCAAGCAGCATCACTCAACCGGCCATCACTTCGGGACCTTTTTCCCTGCCTTTTA

MARKER 17333 (SEQ ID NO: 32): A→G
CATTGCGAATGACCGCTATGGAATATCAATTAGCAGATATTAATCGTGAATTAAGCACATTGGTGGAATTTTTACGA

CCAAATCGAATTTCAAAAAATGCTACACTTGCAACATCAGCAACCATTGCAACATATAACAGTACTTCGATGCGTAA

TGTAAAAAAGAAATGTAATGCATCTGAAAGCTGAAAATTCATCTGATATATTGAAGCAAAAGGTAAGATTATTTTTA

AGATATCATTCTTGATGCTCTCATAATTTCTACATCAAATTTAATCAAACGATTCATTTATGTTCATTT

MARKER 18110 (SEQ ID NO: 33): C→T
TTCTTGTTGTACCTATCATAGATGATAACTTAAGTACCAATAGCAATAGTGCAACGATGCAAGGATTCTGATTAATG

ATTATAAAAGTTTAACCAATCTTCTTCATTCCTTCTAATCAAGAGAAAAAAAATGAGAACATTTTTATGACATTTG

AAGAAAGGCAATTTATCGCTGAAAATTCTACTGCGATATGGAAGTATCAGATAGAGAAAATAAATATTAAAATATGG

ATTTCATACGAAAAATGATAAAAGATAATAATTTACATTTTGGTGCTTTACTGATATGATTGGAGTATT

MARKER 19999 (SEQ ID NO: 34): T→A
CGATATTTTTTGGACGAATCAAACCTTTTTGGGAAATCATTTGATGTCACAAGCATGGTTTGAGAAATTTTTTCCG

AATTAGTTCTGCTAAAAATACTCCAAATGAGTCTAGTGGAATTAAGCTAAGCACCTTAAGTAAGTTGAGAAAAACGT

TTCCATTTGACTAACAAGGCTAGTATATCGACATGAGACAGAAATGGTTATTACTTCACTCACTTCATGAAGCGAAT

ACGAAATATCTGTTCACTTTAGTTTCAATCTACTATTTTACCAATAAACGTGTTCTTTTCCGGATAAAT

MARKER 20570 (SEQ ID NO: 35): T→C
TCTTAATTGATTTTCTTAACTCGAAACACTTGTCTTGATTACTGTGCTGTACTTTATCTTATTAAATTAAATAATTT

CCATGACCACTTCATACCATTGACCATCAAACTTTGATGAAGTTTATGTGTGAAGTGCCAAACAATCATTCATCCCT

TCAGTTTAACTTATTGCTGGTCAAATTCATAAAAATGCAAATTATCAAGCAGATAGTAATTCAGTGAACGTAGCGTA

TTCTCGAAATTTCTTTCCTTGTATTTACCTTATATAGAACAACGTATATTTGTAGCATATATTCAATAT

MARKER 20587 (SEQ ID NO: 36): G→A
TTTCTGAGTTTGCGTTACAGCGCCAAATCTTCACGGAGATAGATAAAATACTTATCGTGAAATTTTGGCGCCATGAT

TTAAAAAACACGGAGATAAAAATAAAATGCTTATCGGTGATAATTTAGCGCCATAATATGAATGAATTGAAAAAACA

ATTTGAGTAGAAACATGACATAGAGTTTTCGTTTTCTGGCTACGAAAATGGATGAATTTTTCTGGAATCGAATTCAG

TCAAAGAATAGGAACGTTGTTACTAAATGATCGAAAAGCTTTCTAAAATTAAATTTATGACGTCTAAG

MARKER 20698 (SEQ ID NO: 37): T→C
ATCTAAATCTTCGTTTTATAGTGGTAAGACTTCCATTTGCTGCATTCTTGCAAATTAAGCTGTTGAAAATACTTTTT

TTTTTGATAGATTTCCAATTTAATCATATTATAAGAAGAATTAATTTCGAATAGAATTTTTAAATCATTTAAACTTT

AAGTTTTAAAACTAATATAAGTTATGCAGATTTCGCGAAAAAGTCTCATTTGTTAATTCAATTATTCCAAAATGTAA

TAATTTTATAAATTCAAATTTAAACTACTACTAACTTCTGAAGTCAGGAGCCAGTAGCAACAACGTAAT

MARKER 21554 (SEQ ID NO: 38): A→G
AACTTTACATTTATATTCAATTTTTTTTTATTTTGTTTGTTTTTAGAAATTTGAAAATGGGTACTAATCAGTGTCAT

TTGCAGCCTCTTAGACCCTCTTTATAACGACCGATTCGATGAAATACGTCATCAATATGCCAGTTTATTGTTCGGGT

GGAGAATGTTTTCAAAAGTTGCTGAAGTGATGAAGTATAGTGAGAATGCACCTTATTCAGCACCATTAAGAAGTAAA

TTTTTGCTTTGGAATTTGACAAAGACAAAGCAGGAAGTTGACAACGATGTTCTGATGAAACGGTTTCGA

MARKER 22174 (SEQ ID NO: 39): A→C
GTCTATTTTGGCTGTCTTCTAATAATTCATTTTGTAACCTTTTGAAATATGATAAATGTAGAAATTTTTCTTCCTG

GTCTATAATAGTTTAATAATGTGTTGTAGTAATAGTTTTGGTGCCGTTGAAATATTTCAATGATATGCTATCGCAAA

-continued

ATTAGGAATTCAAATCAAGGTTACAAGATAATTCAAAAACAAACAACGTAAAAATGAAATAATTTCTTCTTCTTACT

TACCAACAGGCATATCATCATCATCCTCAAATTCATGACTATATTTAACATTGTCATATTTGAATAATC

MARKER 22254 (SEQ ID NO: 40): C→A
CGACGCAAAAATCTTTCAAATTGTCACCCAGTTCTCTAAGTGATTCCAATGATGTTGGTAAACATTCTGCATGATGT

ACCGGGTAATGAACTACCAAGTTGTTTTTGCTTTTAATACAACTCGCAAAGATTCTGAAAACCATGAAATTAAGAA

AGATTAAAATAATCTGAACTCTTTTTTTCATTTTTCCTTGAACTTAGCAATATACTGAGTTGGATAAAATTTAGAAA

CGAAATTTCGCAAATTTATTCAGTAAATTCAGGAAAACTCGGTTTCGGTATTCTAAATATAAATAGATA

MARKER 22259 (SEQ ID NO: 41): A→G
GTTTCTTTGGTTTATCTCAGTAAGATTTGGGCGGAAATTTCAGTTATACTTTTCATTTCCATGTGCTGTTTTAAATT

TCTTCCATATTAGTATAATTTTCAAATAATTGTAGCGTCACTGGTTTATTTAAGGATAACAGGTTGGACTGCAGTGG

CTGAGAAGTGTCTTGCCGGTCAATTGTTTGTTGGTGATCAACTTGTACGAGTTACTGATATCGACATATATAATACA

CGGCAAATTCCATTCGTTTTCAGTACTGCATCAAAAACGGGATTATCGGTACTTTGTAAATCGCAGTAT

MARKER 24708 (SEQ ID NO: 42): C→T
GACCCCTGCTCACAAGGCAGTTCCCACAGACAATCACACATCTAATCACACACATCAACTCATCCGACGTAGGCTAT

CAATAAGGAAAATTGCATTGCTTTATCGTCTAACTGTAATAAACATCTACATAATGAAATTATTTCGCCACTATGAC

AACTAATATCGCCCAATGCAAATATTTGTCTCAGAGTTATTCCCTTTTAACAGCTGTTGAACGAATAGATAGGACGT

CATGTGGATGATCTACTTGTTTCAAAGGTTGAGGTAACACATGAAACACATGAAAACGGTAATTTAAAA

MARKER 25276 A (SEQ ID NO: 43): A→G
AAAGAATGGTCAGCAAGATGTGGAAAATCGATTACTATAGTTGAAGTATGAATCGAAGAGGTTTTTTTAAATTCTAA

GAGAACGAATAATCGGCAAAGAGAAAGTTGAGTAACCTTATTTTGCCTTGTTTTCAGTCAATTTATAATATGCGGTT

AATTGTGTTAAAGAAAGTACAAGGTATGAAATCTAAGCCAAGAAATAAGAGAAAACAGCTAATGATTATTTCTGCAT

TTTTTCTTTTTCGACACAAACTTGGAACCAGAATCAATTGAACTAGTAATCAGATTTTGATTATTGCTT

MARKER 25443 (SEQ ID NO: 44): T→C
TTAGATTTTGCTGAAGCATTGTTGGTTAGATCGATGAAAATATAATTATGAGAGATTTTGTTGAAATTCAGCAACAA

AATTATTATTCATGTCTTCATGCTGTCAGTTTTGTTTTTATTTCTTCTTTGACATCGGTTATATTTTTGTCTTCCAA

CAATATAAAAAAAAAATTATAATCAATTGGTAATCAAATTAAAACTCTAATTGTTAGCTCCCTAAATCAGCTTTAAA

AAAATAATTGCTTAATTGGTATTTGCTACTATTAGCAAACTGAAACTATCCTTTTCTCGAATGGTGAAC

MARKER 26447 (SEQ ID NO: 45): G→A
ATGAGCTGATATTTGATATGCATATTAAAAATAGGGTAAATTACATTAAGTTAGATATCGTTCGGATAAATTAATTA

GAAAAAATGTTTACCAATTAGATCGCAATGATGTAAAATTTCACGTATTTTTATTCTTAAGATTTATTTGCAAAATT

CAAAAATATGTCTTATGAAAAATAATATTTCTGTGTAAGAACAAGGGACCGATTCACTTGATTTATTCGCAAACAAT

CGAAATTCAAAATTAGTAATTTTAAATATTGCTTTATTCAAACCATACCAATAATAATTTGAGAGATTT

MARKER 26730 (SEQ ID NO: 46): A→G
ATTGATTGATTCAAATAAGAAATTTAAATTATTTCCCCTTTTTTTCAAAAGATTTAACAAATATTATTTATTTGATC

TCCTCGTTCGTTCTTATCTTTTTGATTATCAATCCATCCTCCTCCATCATATAGCTAATTTATTTTTTGCATCGTAA

ATCAATTGATGTATGATTGATTTCTTGATTATAAAAAGTTAGAAGAATTGAATTGCTTAAATTTAATTATTGATAAT

GAAATATTATTATATTTCAAAATGATACGAAGAAATATGACGATGATAAGAGAAAATATGATATTTATC

MARKER 26974 (SEQ ID NO: 47): C→T
TACGATAAGTTATTTTATTTTACACATCTCCATCCTTGACTAGTGTCCGTGCCGACTGTCGGACTTGAACCGACAAC

CTACTAATTACAAGTCAGTTGCTCTACCCAATTGAGCTAAGCCGGCCATCTAGAATGTGCGACCCCGTCGTGGTACA

TCTTCTATAATCGTTTGGTATTCAGGACTCTCTTCTTTCGTGGGTGGAGGATCTTGATACAGTTGACTATTAAAAAT

AGGGCCTTTGTTAGTCTGTTACAACTCATAGACAAAGGCGACAATTTTAGCTTACATCTTACGTTATGC

MARKER 27080 A (SEQ ID NO: 48): A→G
ATGGTAGAAAATTATATGAAAAAATATCATACTAAAAATATAACAGATTGTTATAAGGTATGGTTTAAGAATTTACA

ACAATTGATTATTTATGATAAAAAAAAAAAAAGTAAATCAGTGAATCATTAAGATAGTTATGATAAGCAGTTTGTAT

TCGGTAAAGCGAATGATTAGAGGAATTATGGGACGAAACGTCTATAACCTATTCTCAAACTTTTAATGAGTATGACG

TGTCTTGCTTGCTTAAAATTATTTCAATGATCATTTCACTTTACCAGTATGATCATGATTAGACTTGAA

MARKER 27349 (SEQ ID NO: 49): T→A
TTAGTATCGATATTATCACAAATGATATCACTTTCATCAATACTGGATACGATTTTATTAGTATCATAATTTTGTGG

CTCGCATTCCGAAAGTTTTACACGTAGAAGATTAACCTGCAATATGATTTATTTTATCATTTTCGAATATCCAACTT

TGAAATAATTCGAAAATGTTGAAAAATTTTGAAAAATTGTTAACAAAATATTACAAAAATATCAAATGAAATTAAAT

AACTGTCCATTTCAAAAAAGAAGAAAAATTATGAAATTACCAATTAAAAACAGGACTTATTAATTAAA

MARKER 27461 (SEQ ID NO: 50): G→T
TGTGGAAATAAAGTACAATTAATTGCTGTTCGCTTAATAATATTATTTTCATTCTTGGCTTTTTTTTCTTTCCCCG

TGATATTATAAAATATAGTTTTTTAATTTTAACAAATCGTCATAATTATTTAAAAAATACTGAGGTGAGTAAATGTA

ATTGGTTGCTGGAAAAAAAGTGGGTGATGAGAGGTGAATGAAAGCAGAATAGTTTATGATTGCATCAAATTTCCTCC

TTAATCTGTGATTAAAATCAAACAAAACCCGAAAAGTTTCTTCTTCGCCTTTTTCTTCTCTTTGTTTCA

MARKER 29128 (SEQ ID NO: 51): T→C
CGAAATCCGCCGCGTGCATTACTTTGCGCTTGTTGATTACGACGCATTTGTTCGTCGTTGATAACCTTATCAATCAT

CATACGTCCGTTACGTATGCAATCAACATCGCCAGTTAGGCTGAAATCAAATGGATGGCGATGATATCAAAACAAA

AATAAGGAGTATTTGCTGAATCATTTCTTTTTCTGTATTATTATCAAAATTTTCTCCTTTCCATTGTTTCCTTCTTA

ATCAAGTGAATGCTCATTTCATTTTGAAATAATCCAACGTAATAATTCCCCATATTCCCAATTACTTTC

MARKER 29168 (SEQ ID NO: 52): A→G
AGAAATATTAAACTTTGAAAAGATGTGACATGTTCTGTAACAAAAGCCCAAAATTTCGACTGCTGCGGCTTGAAGTA

AAATTTTGGAATATGCTACATCAGTAGTGCAACAGATGGTTCGATAAATAGTGGTAAGTGATGGGAATCCTAGGAAT

AGATGGGAATTGTATTTCAGATATAAATTTGATGCATATTTTCATAGTTGATTATATCTACGATCACACGTTGAATA

TTCTAAAAGCAAACTGTAATTAACTAATTGAATTTGAAAATTTCCAAGAATTAAAATTGGTAACAAAAA

MARKER 29455 (SEQ ID NO: 53): T→A
ATTGTCAGGAATGAGAAGCAAGTTTTGGATACTTAAGGGATGAATGGAACACATACATGGCAGAAAATGTTAGTAAT

CAAACCATTTAAATTACTTAGCCACTATGCTAAACTTTCTAGAAGTATGGTTGAACGTTTAAAAACCTTCGCAAAAA

TTGTATTAGATTATCTTAATCTTCCCTACATCAAAACAGAGAATTTTTGTTCTACGACGTGAGTCTGCATGTATTAA

GGAAGTTCGTATCATGACGTAAATATCCTGAGTGATTATTGAATTCAGAAAATGAGCTTTTTCATTTGG

MARKER 29816 (SEQ ID NO: 54): G→A
ATATGAGTGTTACATGTGTACGTTACATGTAAATATTATATGTTATATGTAAAAATGTCATGTATAGCATCTATTCA

CGTGTACGTACACGTGTATATACATATACATTGATACTTAATACGTATACGCATGAATGAACAGATATTATATATTT

ACGTACACTAGACTCACATGTACCTCTGTATACGCATACATGTACAGATATATGTTTGACATACGTAAATTCATATA

TGCTTTTATTTATGCTTATATTAATTGTCACATACATGCCTTATATTTTCGTTGTTATAAACACATAAA

MARKER 30575 (SEQ ID NO: 55): T→C
GAAAATAAAATTAGCTGAAAATATATGCGAGGTAAAGCACACAGAAGAATTAACTTAAGGTAATATATTGTAAGAAT

TTTTATATTCGGCGCACCTAATAATTTTTAGACCGCATATGCCCAGTATTTGAAACTGGTAGCGCTGTTCGTACTTG

CTGTTGTCCATGTTATGTATATGATACCATTCCTAAATACTTTTGCGGCTGTGGTTTCCAGTGTTGATGTGACTGGT

ATGATGCCTAACACTGGATCCTTCCATCTGCGGCATTTTGTTGAAATTCTTATTGATGTGAGCTGTTTA

MARKER 30991 (SEQ ID NO: 56): A→G
CAACTGTGAATCATAAACATTACTTAAATTAATGAAGCTAGTTAACGACAAATATATTTTTTATGTATCAGTGCTA

TCATATAACATAAAAACTTACTTTCATTAATAAATGAGCTCAAATATTGACTTTTGTCCAAAATGCTCAAAATGTCG

TCATAATATTTGAAATGAAGATAATTTCACGCTTTTCGAAGCCTCCTCTCACGTCTTTTAATCTTCTTTTCTTCTTC

TTGCTCTAATGGTTCTGCGAAAAACCACGGTGCAATAATCACTTTCCATAATTTATACAGTACATAAGC

MARKER 31796 (SEQ ID NO: 57): A→G
CTGCTTAACTCTTTTCATTTTTCAGAGAATCTTCTCTAAAATTGTGAATTGATCCAAACCAAAGAATATGGATAATG

TGATTCGAATTCCTGGAATTTAGATTTTGAGAGTTTTGAAGTTTTTAAAGAGATTGAATTTCTGTGACCTTCTGGTA

-continued

TATTTGATGTCATTTCGGGATGCGTATTTTTGCCGAAAATTTTTGGCCTCACTGCAATCTTGTTAAAAGTCAAAAAA

ATTCAATCGTAGAATTTCGGGTTTACCTGATATTACTGGAAATCTCTGATCTTTGTTCTAGATTGCTGT

MARKER 32164 (SEQ ID NO: 58): A→T
ATAAAGAATTTGCAACTCTGTATACCTTTTTGCAGTGCAAAAGCGGATGAATTCTTCACTGCAGTGTGACAGATTCC

TTTGATAAAATTGCTTCGTTCTTATGTAAACTTGGAAATTCTCGGTAGTTATGCTTTTGCTAGTTGAAAATGTTCTG

CTCTTGTAAAACATGCAAAAAGAGATTATCTTTGTTCTATTATGGAAAGATTCTTTTGAAATTTTGACGACTGAGAA

GACAAATTTTATCCCAACTTGTCATCTGCAATAAAAATTTTTCCTGACCTGTTTCTTAACCTTCCAAGT

MARKER 32223 (SEQ ID NO: 59): T→C
AAAATCAAATCAATATGATCAGATAACTCATACTTATCTTACTGAAAATTCCTCATTCAAGGGAAATAAATAATTGC

AATTCTTGATTCCGATCATGGATGATTTTCAAGCAAATTACCAATGATATCTATCGATAACGATTACAGCATACAGC

TATAACTTATTATTGATTGAATTGATGAAAATAATTTTACCAGAAATTTATCAATGTTTATCTCATTGCAGTATACG

ATGTTTAGTGTGACAACACTTTTTCTTGGAATAATTGTGCATAAATCATTGATTGCATTTAGTATTGGA

MARKER 34439 (SEQ ID NO: 60): T→C
TCCTGCCCACATTCTTTCTACTTTAGATAATCAACAGGAGTTAGTTGAAAGAGAAGACTAGGAACAGTTGCAACTTC

TGAATCTTTCTGACTTTCTTTCGTTTTGTAAATTATTTATTTGTATAAATTTAAAATTCGAAGAGAAATAATCCAAG

GTCCAACTTCTTTTTCTGTTAGTTCTTGCGAATGCTCCATCAAAATGCAAAAATATGATTAGAATTCTGATGGAAAT

TAACAAAATCGATTAGATAAGAAAAGTACAAAACAGAAACTAACTTTTTCTCCCATTTTCATATTATAG

MARKER 34903 (SEQ ID NO: 61): T→C
TCATTGCTTTAATACTTTTTAACGAGAATTTTCTCGATCAAAATAAGATCTGCAATTGATATACGTCAATAAGCGAA

CATTAGCTGTATTACACGCTAATATTCACATATGATGAACGTTGTAAGCGTCATACATCAACATATATCCATCCGAT

AAATAATGACCACTACACATTGCTACCAACCATCCTATCCCGCCACTATTTGAAATGAACTGAGAAGGAGTTATCGA

CACAGGCTTCCTAGCAACCAAACAAAAGACGAGACAGATGAATAGATAGACAGACAGACGAACATACAA

MARKER 35336 (SEQ ID NO: 62): A→G
AGATTCTGGTTATTATTGTATTTCTGATTTATTTAATCCCAACTTAAAGATTCATTGGCTATTGTTTAGCATCTATA

TCAATTTTATAAATAAATAGTAATACCTGATGAAAAGCAATAAATAATTAGATGCAAATTTTAATTAGATACAGTTT

GATGGAAAACATTGAAGCCATGTACAACTAATTTATGCATGTTGAATTATGCATGCATAATTAATTTATGCATGACA

GCAAGTTTGGTATAAAATTAATTTTGTATGAAGATAAAATTTTATAAATAATGATAATAATGCTGGTAA

MARKER 36040 (SEQ ID NO: 63): T→C
ATTATTGAAAAGAATAATGTAGCTAATTAGTTGAAGCTGTTAAAAGTAAAGCTAAAAGATGATGGAAATTATTCGT

ATAAACATTCTTTGTAAACAAACAGTCATTTCTGTGAATAAACAATTATAATTATAAACAATACTTTTCAAGACAAT

AAAAAAATTAGGAAGCATTGTTGTGATAATCAATAGTTGATAGACTGTCAATGTATTTTATCAGTCGTGCTGCTTT

TTTTCCCTTTCTTGACTCATTTATTTTATTATTTATTGATAGAATGTCAATATTCTAGTCATTTGTTAT

MARKER 37881 (SEQ ID NO: 64): T→C
ATCTTAACTTGCTTTAAACAAATAAATTAAAACAGCCCAATGTTCCAAGAAAAAAAGATAAGTTAAAAGTGGGGTGT

CCAAAAATTTATGAATTGAATTGGACAGTTATTCAGATCCTGAAAATACGCTTCTCTGATCACTGCAAATATTCCCG

ATAAATAAGTGAACATTAGGTTAATCTTAATTTTCCCTTAACTTTCCTTAGCCTTTTTAAATTTTTGGATTATTCA

AGCATTTTTATTGCGGTATCGTTTTTGTAAAAAAAAAGTATAATTCAACATTCAGGCTCGACGTTATG

MARKER 38622 A (SEQ ID NO: 65): C→A
AATTAATAAAAGAAAGGAATACGATAAAATATCTATTTTTTGAAACTAATCAAACATATTCCTCACTGCTCACCGG

ATAGTTGCTTTCTAATTTTACATTAAGAAATATATTTTTTTTTTCAATAAGGAAAGTTATGCAGACTAGGAGAATT

CTACTCTGAAGAAGAGATAAGCATGTTAGAATTATTAAAATCTATGGAAATATCCTTAAAAGAATGCCTATAGTAGC

TCTGATTTCGAAAAAAAAAGCAAAAAACAAAATAACAAATTCTGCTCAATTGAAATAAAAAACTTTCCT

MARKER 38622 B (SEQ ID NO: 66): C→T
TAAAATATCTATTTTTTGAAACTAATCAAACATATTCCTCACTGCTCACCGGATAGTTGCTTTCTAATTTTACATTA

AGAAATATATTTTTTTTTTCAATAAGGAAAGTTATGCAGACTAGGAGCATTCTACTCTGAAGAAGAGATAAGTATG

TTAGAATTATTAAAATCTATGGAAATATCCTTAAAAGAATGCCTATAGTAGCTCTGATTTCGAAAAAAAAGCAAAA

AACAAAATAACAAATTCTGCTCAATTGAAATAAAAAACTTTCCTTCAACTTCCAGCATCACTGCTGTGA

MARKER 38622 C (SEQ ID NO: 67): C→T
AACTGCTAAAAAATTGAAACTAGTGTTAGATTGATAAGTGGGCAGATTAAAACCAATTGTGTTATTGGCCCGTTAAT

TAGTGACTCTGAATAGCTATGGCGAATCGTATAGTGTTGTACCGACGACGTATCTATCAAATGTCTGCCTTGTTAAA

TTTCGATGATAGTTTATGTGCCTATTATAGTTGTAACGAGTAACGGAGAATAAGGTTTCGACTCCGGAGAGGGAGCC

TGAGTTGCCACATTCAAGGAAGGAAGCAGTCGCGAAGATTACCCACTCTTAGAATGAGGAAAGAGTGAC

MARKER 38622 D (SEQ ID NO: 68): C→T
GAAAACTAAGAAGTAAGTGAAATTTCTAAGTTCTTTCCCAGAAAGGTTAGATCCAATATTTGTTTTCATTTTAGCAT

TTTTATCCAATGAAAAATGTGCCCAATAAATACTTGTATATAGTATTGCATTTAAAAACTTCAGAAAGCACAATGAG

ATCTAAGCTCAGAAATATGACGAATACCAATCCTTTTCCTAGTCTTACCGCTTCTTAACTTTTGTGTCGCTTTATAA

AAATTAAAAATAAAAAGTTGAACAATGGGAATTACATCATTTTCATCTGAATGGTTTATTTCCTATTCT

MARKER 39492 (SEQ ID NO: 69): T→C
CTTCCCTAGCTATGCCTTTTCGTCACTTAAGCTTCNNNNNNNNNNNTCTAGCTACGTATCGTTATCATTTATGCTTCT

TTAGCTACGTTTCTCCATCATTTATGCTTCCTAAGCTACGTATCTTCATCACTTACGCTTCCCTAGCTATGTCCTTT

CGTCACTTAAGCTTCTTTGGCTGCGTGTCTTCATCATTAATCTTCTTTAGCTACGTATCGTTATCATTTACGCTTCC

TTAGCTACGTCTTTCCATCATTTATGCTTCCCAAGCTACGTATTTTCATCATTTATGCTTCCTTAGATA

MARKER 42291 (SEQ ID NO: 70): G→A
GATCTTAAAATTCTATGAAACTTCTTCTGCATGGTATTGTTTCCAACAGAATATAATGACAATAGCAACAGTATTGG

TTATATAAAAATATTGACTGCAGCAGGATTATATTTCAAGTTCTTTTAATTTCATTTATTTATTCTTTCATTTACTT

TTACTGTTTTTATGTTTTTCTTCTTTAAAAAATATGATTTCTCTCACTGTTCTCTTTCATCTATCTATATTTATTTG

ATAATTGCTTATATGATAACTAGCTAAAGGGAAATAAACTTTCAGTCATCATAGCTTCATTTTAGTAAA

MARKER 42411 (SEQ ID NO: 71): A→T
CTATACTAATCAGTCCACTATCCATTTTTAGGTTGCAAAAGTTGCAATGACGGTTTGATTTCATCCTCCAATGCAAT

TTTGAGTCTCAATCTCGAGAGATAGATCGATCGCTTTTAGCTTGATTTAGCTTGGTTAATGTTGTGAGGGATATTGG

GCAGAAATTCTGTCAAGCGTTACTTAATGAAATAGTAAATGATCACTGATATTTATTGTTAATGATACTTGAGCTCT

CTAGATTATGAACTGGAAGGTTTTCGATAGAAATAATCGATACATATATTAGAATCGACTTCTTTTTTC

MARKER 45689 (SEQ ID NO: 72): A→C
TCATCTTTTTCACATTTCATTTAATCATCATTTTATCAATTCCTATTTTTAAACAAATTCTTTTCAAATATTCTCTC

TTTCCTTCTCTTTTTGTTTTCCGCTTATTCATTCTAATGATGAACAGATGTAGAAAATTTGCATTCTATTGCTCACT

ACAATTTTGAGTAGAATATATTTAATTATTTGATTCGAGACAGATGGTTATAGCCTTTAGCTTCAGCTTCTCGTTCA

AATTAAGTACTTGTGACCTTTCCAAGTACCATTAAAGCTTTCCTGCGTTTCCTAATTAGAAAAAAAAGG

MARKER 45719 (SEQ ID NO: 73): G→A
GCATTTTAAGTTAAAAGTATCACGCTGCATGACACCTCACGTTTGCTATCTCAAATTGAGTAGGTTAGAATCTTTTT

TTGGCTACTATTCAAATATTAATAATAAATTGCTGCAAACAGATTTCACACCGGAAAAAAATTAAATTTTTCTAGCA

ATGTTTTAACTCCCTTATTAAATATTTATAGAAAATCGACTACTTAAAAAGAATTGACTAACATTTCTGAATCTCTG

CAGAGATTTATAGATGGATTAGCATCCTACAAGTTTTTATCTTTTTGCTATATTTCCATTATTTTTTA

MARKER 46063 (SEQ ID NO: 74): T→A
GATAAGACGTCTTATTTTGTAATAATTCAAAAATTAATTAATATAGAAGTAAGATCTTGATAATAATTAATATGCTC

AAATTTCTTAATGAGAATATGTTCAGGATGAAGATGAAGTGAAAGAAATTGATAGATTGAGGAAGCAATTGCTAATT

GAAACAGAACAGCTCGTTTCCAATTCTCTTAAAGATTTACTGAAGAAAATTTATTATCCACTTGAAGAAGCTATTGA

TCTCAAAATTCATCAGAAATTAATTCAACAAATTGCTGCCTTGTTGAAGTGTATTAGTATCTTGGATAA

MARKER 47481 (SEQ ID NO: 75): C→G
ACCGCAAAATACCTAAAAATTTCTATAACAACGATTAACACGGCCTCGAACTGGAAGCATATTAATCCATGCGTGGC

TCAAACTTCAATCATAAAGACAAGATCTAGAGATCAACACAAAATGGTGAATTGTTACCCTATCGTTGCTAAAGTTT

-continued

GAGAGAAAAAAGTGCTAAATCAAGTAGTACACCAAATTTAGTTAATATTAAGAAATCAATTTAGTACTGAATTTAAA

CAAATGAAATTTTACGATAAAATAAAAAAGTACCTGATCAAACAGCGTCCTCCCGTTATTCCCATTGCT

MARKER 47722 A (SEQ ID NO: 76): C→T
TATAAGACTAGTAAACAGATCGTAATATAATAAATATCGATTTTATTTTAAATTTTCGAAAACTTCCAAATCTATCG

ATATGAAATTAAAGATCAATTTTTAATTTCCATAATATATTTAGATTCTATCCCAACATCACTCATCTTTATGTCAA

CTTATTTAATTCTCTTATTAACATTATATTTCTTGTTTACAATGATAAATTTTATCAATTTTCTAATATGATAGAAC

ATCTTCATCATCTGAAGATATGCTTTTCTCATCTTTGTAACAATTCGTATCGCTTCTGATTTTACTTTC

MARKER 48750 B (SEQ ID NO: 77): G→A
GTTTTATTATTGCTTATTGAATAGTGATAATAACACTTTGATATGATATTGTTTTGTTGCGATCATTGTATTGATTA

TAACCTTAATTAAACGAGGATATTATGGGAAATGTATTTATTACAAAATTAAATATGAAAGGTTGAAGTCTTGACGA

AACTTTCAAACACATTTCTCGAATTTTCTCTGCAAAAATATCGTTACGATTTTTGGAAATTATGAAGTCCAAGAATT

CAATCGAGAGTTCGCCATGTCACTTTGGCTAGTTTCGTTTGTTTTTAATATTTCAATCAAAAGTCAATT

MARKER 48750 C (SEQ ID NO: 78): G→A
CCTTGGATATTGTTCTTGACATCGTTGATCAGAAGGTCACCGTAGTGTTCGGTGAGCGAGATGGAATTGGACTCAGG

TTTATTCTCCGTTTTTTTCATGTTTTTGAATTTTAGAGAGAAAATAATGTTTGTCTGAATGGTTAGCAAACTAATTA

GTTTTTAAGTTATCAGGAACTCGAAGTATCTTCTTTTGCACTTCTTTAACCTTTTTCATCAAATTTTTTAACAGTAA

CAAGATTTTTTGAGAATTTTCAAAATATTTTTGACTTCTGATGATATTTGATGAGAAAACCATCACTG

MARKER 48790 (SEQ ID NO: 79): A→C
AGAGTATTATTATACATGATGATGATGATGATGATGATGATGATGATGATGATGATGATATGATGATGATGATGATG

ATGATATGATGATGATGATGATAATGATAATGATGATGATGATGATTAATTGCTTATTTTTAATGATTGATAACTTT

AAAAGAAATCATTGAAATTTGATCGAATAAAAATTTTCTTAAAAAAAGCATTTGCTATTTATATAGTAAACCTATAA

AAAATTACTTATTTTTATTACTAATATTCATTTGATTGTATGAAAGAGAAGAGAAAAAAAACCTTTGCA

MARKER 49731 (SEQ ID NO: 80): T→A
TGGTATCACAGCACTGGGTTTAATTTCAACAATCGGTTGACGATCTTTTCGGGATATGCCTATACCCAGAAATGAAC

GTATGCCAAACGATGGTATGTTTGATGCAACAGACGACGTCAACTTAAAATGTGTTTTTTTTCAAAAATTCAATAT

TTTTAGTTTAAAATTGCACGTCAGTAAAAATTAATTCATAATAAATCTCTTTGATTTCTTCGTTCTCCTTTTTTTTC

AGAAAAAATTGAAATTTTACATACCTGATTTCCAAGAGCATATAAAGCATCACTTAAAGCATTCTGCGA

MARKER 49824 (SEQ ID NO: 81): T→C
TCCTTTTCATGATTTGTAGCTAACCAATAAGATGTGTATATGTTCATATATTTACTCTCCCCTGACTCTTTTACACT

CTCATTCTCTCATTTGTTCATTTAGATAAGTAATATGCGCCTTTCTCTTCCTGATTCTCTCAATCTTTCATCCCTTC

ATCTCCTCAATCTTTCTCCCATTCTCTCAATCTTTCCTGCATTGCATTCATTGATGAAACACGATAGTATTAATAAG

CATAATTTGATAAATTGAAATAATTTTTTTTNNNNNNNNNNTCATTCTCTCAATCTTTCCTGCATTGCA

MARKER 49904 A (SEQ ID NO: 82): A→G
TTTGAATTAACAAAATATTAACAATTACAACTATTTCGGAATTTAATTTAAGAATAATTTAATTAATCAATTTCCTA

TTTTGTATTTTAAAAATTACCACAATAATTATGTAATTTTTGGGATATTTGAAACTTTGAAAAAAGTGGTATTGTAT

TTGAGAATAAATTAATTAATGTAATTCTTGCTGCTCATCGTTCCATAACTTACAAATATTTCTCGGTATTTTATTTG

AGATAATTCTTATCATTTCTTCCATAGCTTTCAATATATTTATAACTTATTTGTAATCACTCTTATCAC

MARKER 50378 (SEQ ID NO: 83): A→G
TTGAGATATCAAATCAAGCGTTGCATATTTATAGTACACTGGTGTAGCTGAAATCGCGAAGAGAACACGAAAATCAG

AGAAGTCAATGGTTCCTTTGTGTTGGATTTCACATGAAAGCATCCTTATGTTGTACATGCGTGATTACAATATGATA

CAAGATGTAAGCTAAAAATTGTTTTATCTTTGTCTATGAGATGTAGTTCATACTCTATAATAAAGTCCCAACCCTTA

ATTCTCATATTCACAACCGTATCAGAATCCAACACCAAACCATTATAAAGAATGTTCTTCGTCGAGGCG

MARKER 51565 (SEQ ID NO: 84): C→T
CCACTATCGCTTACACTTTCTTTATCCTGTTCTTCTTCATCTTTCGTTTTGGACTTTATTTTACTGTCAGGTGACAA

GCAAAGTAACGATGTTGGACTTTGCGAAGATGTGGATGGTACGCTAGAAAAAAAATGAGGATTGGTTAATATGTCTA

-continued

ATTATTACATCGCTTTTTTTAAATCTTTTCTAAAATTAAACTGAATAATCAACTTATTTGCTATTCAGTTTATCTT

ATTTTTTATCAACAAAATTCGAGGAAACAAATCGCTTATCAGAATAATTGTTTTGATCAACAAATAAAG

MARKER 58162 A (SEQ ID NO: 85): G→A
CAATCCCACAAATTCAGTGTGTCGGCGGGTCAGCGAAGGGAAAGTTTGAACCGAGGGTATGTACAAATTGTGATAAT

TTTGTGATGACGTAGTAAATTTCATAGTTTTGCATGCTTTAATGTTGATAGTCGCACAATCCTACGTTGATTAAATT

TAGCTATTAGATATCCTACTAAATTATGTTGTTCATAATTTTTGTTTTTAAAATGCTCCACTTATATTTTCAGGTTG

TGCAGTGCTACAATAGGGGTTATGACGGCAATGATGTCCAATGGGAGTGTAAAGCGGAAATGAGCAATC

MARKER 58864 (SEQ ID NO: 86): T→C
TCAGATAAATTGTATTTGATGTTAATTCAAAGAAGAAAAAAATAATCAGTAGAATATGAATCGAATAATATTCATAC

AACCAGTTTATTCATTATTATTCACTTTTAACGTCTAAATGACGTAGCTACGCTTTTTTTCTCGCTTTCAAGCCTTT

ACTGACCAAGATTAATGTACATTCTGTTGAACAAGATTAATCGACATTCTATCGATCAAGATCAAGCTTTTACTGAT

CAAGATTAATAATGACATTCTTCTGTTGATCAAGATTAATCGACATTCCATTGATCAAGATTAATCGAC

MARKER 62666 A (SEQ ID NO: 87): G→A
CTCTCTAAAACCTATTGGTCACTAAACTTGCACTGACTAAAAACTATTGGTCATCAGACTTGTGATTCATTGAAAAG

ACCGTTAGCCGCTAAAATTATGATTCACTAAAAAAAATCTATTGATCATTAAATCTGTAATCATTGAGAAACTACAA

TCATTGGTCATTAAGTTTGTGCTCTCTAAAACCTATTGGTCATTAAACTGACTAAAAACTATTGGTCACTGAACCTA

GAGTCTATTAAAAAAAAAATCATTGTATCAATAAATTTATTGTTTACTATCAAATCCATTGATTACTGA

MARKER 62666 B (SEQ ID NO: 88): A→T
TCTAAAACCTATTGGTCACTAAACTTGCACTGACTAAAAACTATTGGTCATCAGACTTGTGATTCATTGAAAAGACC

GTTAGCCGCTAAAATTATGATTCACTAAAAAAAATCTATTGATCATTAAATCTGTAATCATTGAGAAACTGCATTCA

TTGGTCATTAAGTTTGTGCTCTCTAAAACCTATTGGTCATTAAACTGACTAAAAACTATTGGTCACTGAACCTAGAG

TCTATTAAAAAAAAAATCATTGTATCAATAAATTTATTGTTTACTATCAAATCCATTGATTACTGAATA

MARKER 7060 (SEQ ID NO: 89): G→A
AAAATGTATCAAATTCTTCGATGCCATAAATTATACAGACTTGATTGGCATTTTTTCTAACTTTCATCATGAACCAT

TCTATTTCTAAATTGATCCATTACAAAATCAACTTTGTGATATCATCAATCTCAGTCATAACGAGAAATAATGATAA

TATAAAGCGACTATCATTTGAATTTCCTGAATATTCAAGATGTAATTACATCTTTTTTTTAATGTAATCAAAATTTC

TTGCCATCAATAATTTTTCAACATATGCTTTCATCGACTGCCTTATGCAGATCGTAATGATGACAGCCA

MARKER 12056 (SEQ ID NO: 90): T→C
ATTGATTAAAAAGAATCAACATTAAATTTTTGATATAGTCGAGAAATCCTTCGTGATAATTCTTTTAGAACAATTCT

TTACACTAAACTTGTATTTACTTGCTTATTATTTGTCTAAAGATACTAACTATTTGTCAGTGGAATTTATGATCTTG

GCATTATTGCATATAACGCTTTCCTAAAATCTGAAATTTTTCAGTATTTTAAAAACTAAGACGATTATTAAATATTA

CTCAAAGCTTAGAACTTTGATTATACTAATCAAATCAAAAATTTCATCAGCGATTTTTGTTGTGTCATT

MARKER 16261 (SEQ ID NO: 91): T→C
ATTTTTTCCAGCAGAATTGTCATCAAAAATCCCATTTTTGATATCCTCTTCATCGAAACTTGCTCCTGAATCCAGAG

AACAACGAAGAATGTGTAAATCTATTTCAGTAGCCTGCTCATTGTGCAATTCAGCGACTTTATTTCTGTGCTTCAAG

CTAACTTCTTCATTATGCCACTCCTCTTCTCTCGCTATTTTTTCGCTATCTAATTCAAAATCTTCGTCTGAAACGGA

ATCAACTCCTGACGATGTACTCGACACTGATAATATTTTCATGCCGATTTTTCTCTCAAACGAATCTTT

MARKER 23195 (SEQ ID NO: 92): C→T
GAATGAAGAGCAAAAAAATAGTCACGACCACCTGCAATAAAAACAGCATCTCCGTAAAAATGATTGAATTGATTCCC

GAAATACGAGTTTATCAAATTGAGAATTATGCAAATTAATTATCAGCATGCAGATTTACTGATTTTATATCTCTCAT

ACCGAAATTAAGGTGATGTTTTCCATTTCTTTGTTTCCACAATGTCTTCTTTGTGAATCGTTTTGGATCAACTATTA

ATCCGATCGAATCAATCCTCCAAATATGAGTTTATTCAACGTAACAAAACATTGTCCGAGATAATCAAA

MARKER 28579 (SEQ ID NO: 93): T→C
TGGAAATTTCGAAATCGAAAGGATGAAGAAAAAGGATCCTTGATCTATACATTAAATATCACCATATCAACTAGCAT

GGCAAGTCAAAGTAATGTTATCATTTAAATAAAAAAGATGAATAGTAGGACTACAGGTTATATTGTTAAAAGTCGAC

-continued

AAATTTGGAGTAATTGACAGAGATCAACGATTAAATGTAATGGATGATCTTATCTTCTTTTTTCAACTACGCCAAAA

TGAAAATAACAATTGAATTTGTCGAATAAGAAACTAACATTTTGAAAATAAGATTGAACATTTATAAAT

MARKER 48869 (SEQ ID NO: 94): G→A
GGTTGGATCATTATCGACAGAACTTTAGAAGTTTCTTGATAAGGACGAAAAGAAGCAGCACCATTGCTGATCTAAAC

AAGGAAAAAAGACCTTTTTTGGAATATTGAAGTTTTTACTGATAGGTGCGTGCTGTGTACTGTGGGCATAAGTACAA

GCTTCATGCTCCGCAGCGTGAATACGTGCTGCATGCATACTATGCAGTAAAGGTGCGTGTCGTATTGCTCAATAAGT

GTATAAATTGCTGCTTTTCTTGCATAGTTAAATATTTTGTTTTCATTTTTTCCGCTATTCAAAATAAAT

MARKER 53021 (SEQ ID NO: 95): G→A
GTTGGGATTTCAGACTCTCACTCGGTGTCGTTTCACAGTGATATCTGAATCGAAGTCACAAGCAGGTATGAATGCAT

AACAACTAATATCCATTGCAGAAACAAGGCAAAACTGAGAAGCTCGAGCAATATAGCTATAGAAGCTGGTACCACAG

ATGACATTACATGGTATTTCCATTTCAGCTTCACAAACATTGTAAATAGCTTGCTTCGATGATTCAATATCTCGTTC

TACGATATTCTTAAAGTAATTTTTATTTATTTGAAGTATAGATTACATCCATGTTCTATCTATCATTTC

MARKER 7986 (SEQ ID NO: 96): G→A
TGTTCTGAACATCTCTTTTTGATTATCTTTTTTAATTCCTCCATTATTTTCGTTTTTTTCGTTGTGAATTAATATTG

TTTGTCTTTGATTCAGATGATATTTTCGGATCGTAAATAGATGGCATCGGCATAAGCGTATTGAGAAGCATTCAATG

GTGCACTCTTGCTTCTTTTTTTTTGAAATCTTTCTCGATAATCAAATAAGTGCAGGATGCCAATCATTAACAATTT

CGTTCCACTTTTTCAGTTCTTATTCTTATAACACCACATCTCATTTGCAATTTTGTCGCCAATGATTTT

MARKER 48094 (SEQ ID NO: 97): C→T
TTTTTTCGAGGTCACTCTGGAAAAATAAATCATATTTTAAAAAGACATAAAATAAAAAATATGTATATATAAGAAAA

TTTTTACTCTGAATTTCTTAAGAAAATTCTCGATTCTGTTTTCCATAAATTCCGGAATATGTTGTCCCTGAATTAAG

AATTCGATTCCTTGCACACCATTATTTCGTCTAGTTCCTGTGTGAACAATGTAACCTGGAAATGAACACATAAACTG

TAATATTTTGAGCTTAAAATAATTATGAGGATGCGAAACTGAAGATATTCATAAATGTTTAAAAAAAAA

MARKER 6568 (SEQ ID NO: 98): T→C
GTCCATGCATTGCTTTTCGGAAGTTAGTGTAGATTCAGTGAATATTTAATACCAGTCTCTTTCTAATTCAAAAGAGC

CTCCCATTTCTTTTTTCAGTTTCAGTCTCTGAATCAGAGCGTGTAATCTACCACTCCATTGCCGAAAACAGCTCGAT

GTATTTCCTGCTACGTAGTGTTTAGAATTGGCGTATGCCACTTGCTCATTATTCGCGCATGAAGTGTAACTGTGAAT

AGAATGATACTACTGTTAGAAGAGAATGCGTTCACTTTATTTAACATTATACTGATTCATTTCTTCTTT

MARKER 17022 (SEQ ID NO: 99): C→T
AGTGAACGAGAAAAAACAGAAGAAGAGATAGCACATCAAGATCGTGAGAAATTAATTAGACAAGAAAAAGCTCGTCT

TACACAAATATATCAGGTTTTCTTTTTCTTGCTTTCGAAAGTTATTTGAATTATCTCATTTCTTTGAATTTTATAAG

AAATAATTTAATTTTTTTTGAAATTTTGCCTATTGAGCTCTAAATTTTGTAAAAAGTTTTCTAGGATGATGTTAGC

AAAGCAAAAAGAAATCCAAAAGTGATGGTAACAAACAGGAAGATTTTATAGTGAGGTACGATAATACG

MARKER 55751 A (SEQ ID NO: 100): A→G
TAGACAATATCATCCTTCCTTTTTTTTTGCTCAATTTCTCTGCTCATTGCTTTGATGATAATGGTAGGTGGTATAAT

GAAACGAATAGATAATTGATGTTCGCAAACATTTGCTGTTAAATTTCAGTAAAGAAATTGACCTTTTTGCTTTGTGT

TGGATGTTTAGCTTCATTTTCTTCTTGTTCATTGTCATATTCATTCTCTCAAAACTTCTTGCTTAGCGATGCTAATA

TAAATACTGGAAGAATGCCTTTGCTTTGTTTTAGTTGTAAATCATCACCAAGGTATTTTTTTGCAAAAT

MARKER 55751 B (SEQ ID NO: 101): A→G
AAGATGAAACTAAAAAAAATTATTTCGAAAAAAAGAAAATAAAATTAATGAAATAAAAGCAAAAATGAACAAACCGT

ATTAATTTTAAACAATAAACAATATCGAAATCGAAAAATGGACTATTATTGATGAACTATATTTTCAAAATGTGAAA

GGTCAAAGTTTGTTTCAATTATGATAAATACAATTTAAAATAAGATTAAGCTAACAAATAAGTTGAGCAAATTGATG

AAACAAACAAATCAGAATATATTACAGAAAATGATATAACATGAAAATATATTAGACCAATTATTTTA

MARKER 15893 (SEQ ID NO: 102): T→C
TTGAAGTTTTCAGATAAACTTTGATAAAAAATTGTTCTATGAATTCTCAAATTTCAATTAGTGATACTTATTTCGAA

GGTAATTATGCCTGATTGAATCTTCAATATCAACAAAATGAAAATTTTAGTATGATTGTTAACTCATACACCTCTAA

-continued

TTAAAGGTATTTTCTTTATCCCATGAAATGAAAATTTATTAAGAACTTAGAAAGCTACGGTATGCCTTTGATGCAAA

AGAAAGATTCATTTTCATTAAATCATGTTTAAAAAAAAGAGCAAAGAGCAAAAGGTGATGAAAGTTTTT

MARKER 25462 (SEQ ID NO: 103): C→T
TTCTATACGAAATATTTGTCTGCCATAAATCTACTCAGGAACTCGATACATCAAAACATAAGTACGCTTGCTCTTTA

TTTTTCGTTTGAAAAATAAATAGATCATTTTCGCACTTACATTTCAATTTCAATTGCTTTATTCATATCTTTCTGTT

TTTACTTACTGGTATTTAACAGTCGTTGTTCACAATTTAATGATCTATGAAACACCATTTAATTGTATTTGGACTAA

CTTTTCGACAAGCAAAAGATTAAAATTGTCTTCAGATACAGTTATAAATTTACATTGAAGATAAATGAA

MARKER 33494 (SEQ ID NO: 104): A→C
TAACGATCTGTATATCAATGGAATAATATTCAGTTCATGTTGTACTCGATATGAGATAGAATTACAATTTTGGAACA

AGATAATCTCAACAGCTATTTTCAAGAATAGTTAAATTAGGATACCATTCAAAGAAACTTTAAAAAATGATTTCCAT

ACATTAATGCTTTTTGTGTTTTCGCTCTCGACCAGAATCCAGGAATTGTCCATTATCATCAATTTGATTAACTTTTA

TCTTTATTCTAATTCTTCAACATTTCTCTAATTGATATTAGTTTCAATATTTTAATAAGTAAAAATTTA

MARKER 17935 (SEQ ID NO: 105): T→C
ATAATGTGTTATTGATCAAAGGATTTTTAGTTACCTACCAGATGGAAAAAAAGCAAGTTTACGAAAACAGAAGTTAG

CATCAACTTTCATCCATGGTTACACCGTATATAATCCAATCGACTCATACTTTATGTTGATCTGATTTTATAGCAGA

TAACTAGTTACCTTGCTCAGCAGCAGCTAAATCCTTTCTATTTGCTTAATAACAGAAATATTTTTCATTAACAAAGA

AATTATACTCCGTGTTTGACATTTCATTTTAATTTCGTTCCAAAAATGAAAAAAGCTTCGTCCGGAAAT

MARKER 48561 (SEQ ID NO: 106): C→T
ATTATTTTGTAGTTTTTCATTTTTTAGTTCAATTTTCCTTTGCTTATTTTAAATATGCCATTCTTTATTCAGACTCA

TAGCGAATGCATATGTTCATTAATTTTTTTAGTTACAGTTACAAATTCTCAATTTCTCTTTAATCATTTTTTTTTCC

AAAAATAGTCTGAGCACTCAACCATTCATTCAACAATTGCAGCTTTTTTTATTGGAGCCTTGTCAAATTATCAATTC

GTTTCCATGTTTATTATTGAAATAATAAACGGTATTTAGGATAACGAAGTTCGCTTAGCTTCTTTGACT

MARKER 42003 (SEQ ID NO: 107): T→G
AAAAATTCAGGTAATGAGATCAGTAATTTTTTTGGTCACTTTGCTGTTTCTTATCAGCTCATTGTTATCCATATCA

AATGAGCGAAAGTGTGTATCACATATTGGCAGAGTGTAATCTATGAAGATTTTGCGTATCAAAGTAATTATGAGAGA

ACTGATAATTTTATTTTAAAGTAGTAGAAAACTCGAATTAAGCTAATAAATAATCGGTTGATATCCATGAAATGAAT

TACTAATGAAATGGATAATTGAGTAATAACAAATGATATTCATGAAGAAAGGCAGGTTTTTTTTAATAG

MARKER 29566 (SEQ ID NO: 108): C→T
TATACTTAAAACAAGAAATACAATTAATGCCAATAGCAGAGTGAAACTTCTGAAAAATAATGAGTTGAAACTGGTAA

AATTAACATTTTATTAGAAATTTCAGAAACTTATGACTCCTCATGGCACTATCACAAAATGTTTGAAAAAAATTGAC

AGCTCGCGTCGATTGCAAAAATCATGATTCCTGATATTTAGTATCGAACATGTGACAAATAATATAAAGACCTAACC

ATAAAGCACTGAAACAACTCGCGGAAACAAAAAATTAATTTGCATAAACACGGAATACGATCAGAAAAT

MARKER 33868 (SEQ ID NO: 109): G→A
GAATTTTTTTAGAAGGCTTGAAGTCGAGAATATTAGAGACTATATCGAAGACTTAAATAATCCTGGTAATCTTCTGT

ATGAATCAAAATTACCTCGAACAGAACCATTCAGCACATCACGAGATAATTCATGGAATGAAACTAGCCAATCAGAG

CGTTGTAAAAGAAGAAAGTTATGAAATGACCTTAAAATCAATTTAAAGCATGTCCTCGCCATATAAGCGTTGAAAAG

TTAGGATAGAATCAATTATCAAAAAAAATATGTTAACTAGATCTTATCAATCAAAACATCAGAAGGAAAA

In another example, genetic markers from *D. immitis* include the sequences below (SEQ ID NOs: 110-127), where the underlined nucleotides (i.e., the polymorphic sites) indicate the SNP nucleotide position within the fragment that correlates with resistance to MLs (i.e., the alternative nucleotide). Those markers were identified after genotype frequencies comparison between susceptible individuals and confirmed ML resistant individuals. In these sequences, the underlined nucleotide at the SNP position is generally different than the nucleotide found at this position in organisms that are susceptible to MLs (wild-type). In the sequences below, the nucleotide at the SNP position in the indicated sequence correlates with resistance to MLs. In the heading for each sequence, the nucleotide change from wild-type to the alternative nucleotide (alternative nucleotide correlates with ML resistance) at the polymorphic site is shown.

MARKER 31307 (SEQ ID NO: 110): A→G
ATATGATAATAGTGAAACAATTCCATCACAATAAATATTATCGATTAGG

AGATAAATTAACATTGATGCCTCAATTTTGGTCAACAATATATATTTGC

-continued
TATTAGCATTTTTATTAAATCGTTTTTATCTGACTTGACATAAATTGAA

ATAGAAAAAATTGAATCTGTTCCTTGTTAGATTTTCTTCTAAAAATTCT

TGAAATACAAATAATTTCTTAAATTTCAATATTTCTACATAATGTATTG

CGACAAAAATGCTAATGATTGGCTTATTATTATTTCGAATAATTTTTTA

ATCAAA

MARKER 26225 (SEQ ID NO: 111): A→G
AGCTCGAAGATCGGACAAAATTTGTTCAGCTTGTTGCCTTGAGGCTTTA

GTCTGAAAAGACACTTAAAAGTATAAACAATTATATTCAAAAAATCTT

ATTTTGCATTTGCGTCTTAATTTTTGCTTTTTGCAAAGTTTTTTCCGAG

CAAGTTTTTCTATCTTCGAAAAGATTATATCAATTAAAATTTCAATTTA

AGCAATCATTGCCTCTTCGAGTTTCTGTTTCAGCAAATAAATATCACCA

CCACGACGCTGTCGGAAGAAAGAAACGCCTTTCCCAATTTCTCGTCTCA

ACTTTT

MARKER 47722 B (SEQ ID NO: 112): A→G
TAAGAAAGCTGGGAGATTTTCCAAAAACACTATTTCCCACGATTTGTTG

TTTTCTATGATCAATTCTTAATCAAACTCTGAAATTCTCAAATTTTCGA

TTTCTATCCAACTTCTACATATTTTTTAGAAAATTCATATTTAGCAAA

GCTGAGTGTAGAAATAATTCATACTTGCAATTCATTTTTCTTAAATTTT

CGAATTTCTTAAAAAAGTATTTCAAATTACCTACCAATTTTGATTGGAA

AATTCGTGGATGCTAAAAATTCAAATCAAAATAGTTAAACAGTATTCCT

AATTGT

MARKER 58162 B (SEQ ID NO: 113): T→C
AATTTAAAAAACACATCGACATTTTGCGGTACGGTAATGATTGTTTACA

GTAACTAAATGTGTCCTACGGTAGTAATACTCGTGTACGTAATGAATGA

GTATAGTGACCGGATATTTCCTTCACTAGTAGGCAATATTAAGAAGTAT

TTTCATTTTCATATTCTATCTAAAATAAACCGATAAAATGGTTTTTGAA

TTATTACTTTTTGATTGTTATTTTTTGATCCTAAATTGTAAAATACTGT

AATAATTTAGCTAATTTCTATGATTCTATTCAATATGCTTAAATTAAAA

TTCTAA

MARKER 17709 (SEQ ID NO: 114): T→C
TCGTATTTGTTGTATGTAATATAGAAATATTGTTTAAATTCAATATGTA

GAAAAAATTTCTANNNNNNNNNNNAATTAATTACATATTAACTCGTATTT

GTTGTATGTAATATAGAAATATTGTTTAAATTCAATATGTAGAAAAAAT

TTCCATAATAAAGACGAACAGCATTTATAATTATCAATGATAAGTTGAA

ATTAATTCATCAATGATAAGTTGAAATTAATTTATTTGAAATAATTTCT

TTGAAATTCGAATATAGACGAGAATTTTTTTTTTTTGCTAATCGTTTA

TCAAAT

MARKER 47141 (SEQ ID NO: 115): T→C
TCTAGCAATATAAATTACAAGAATATGCCGTCCAAGTATTTCAGAATTT

ATTATTAATTTGGATAATAATACATTGTAAATACTGCGTATTCTGGATT

ATTATGCACTGCATAATAACATGCAATTTCGTCTACATATCGCGAATAA

ACGCCAAAAGATTTCTCGATAAAAGAAAATATAAGAATTCGTAAATGAA

TGTTGTGTCAGAGATATGTGTTAATTCATAAGTCAAGATGTTGTAAATC

-continued
GATCCATATTAGTAATCATATTTACGTGCTCGTAAATAAAAGCGGTGAT

TCTTGT

MARKER 48750 A (SEQ ID NO: 116): A→G
ATCGAAAAAGATGATCTGATGACGGAAGGCGAAATGTCTGCAGAAGCT

AAGATGACGGAAGAAAAAAGTGAAGAAATGAAAGAAGAAGCTGGTAAAA

CTCAGAAGGAATGTAAAACTGGAGAATCGAAAAAAGATGATCTGATGAC

GGAGGGCGAAATGTCTAAAGAAGCTAAGATGTCGGAAGAAAAAAGTGAA

GAAATGAAAGAAGAAGCTGATAAAACTCAGAAGGAATGTAAAACGGAAG

AATCGAAAAAGACGATCTGACGACAGAAGGCGAAAAATCTGAAGTAGA

TGAGCC

MARKER 63962 (SEQ ID NO: 117): A→G
ACTAATGATAAGAAACGGAGCCGACGATTTTAGGAAATGAATAATAACG

ACATTGACAACCATTGTTAGAAAATTGATAGTACTGATAATAAAAGCTA

GTTATAGAAAATTGATAATAATAATAAAATTGCTGGTAGCAAATGTCTA

GAAGTGATAATAAAATTAATGATAGCAAATGGATTAGCAATGATAATTA

AACTGATGATAGCGAATGGATTAGTAATGATAATAAAATTGATGATAGC

AAATGACTAATAATGGTAATAAAAGTTAATGCTAGTGATAACTTGTATT

TTAAGT

MARKER 6372 (SEQ ID NO: 118): A→G
ACAGTTTATAGTTACAATATTCTCCGGTGACTAACTGTATTTTACAACT

TATAATTATAGATTACAAAATATATTATAGTAGTTTTATAATTACAGTA

TTCTTAAGTGAATAACTATACTTTACAGCTTACAGTTACAGTAGTTTTC

TATGTTTTTGAATATTAATTTTACATGGTTTTTCCTAGTTTCAGTTTCA

AAATTTTCAGATATTTATGTGTTAAAGCAAATTATATTCGAGATATAA

AAAGTACTGGTCATATCTTACAATTCTCATCCTTCTATATTGGAAAGAA

TTGAGT

MARKER 15611 (SEQ ID NO: 119): T→C
GTATTGGGACCGCGTATCGGGAAATCTGAAAGAAGTCTTTAACAGTATT

TTAAATGAATAATTCAAATCGTTACTTCTTAATATATTAATTTATGCGT

ATATATGCAGTACATAGCATTGCTTAAATTCTTATTTTTCCGCGGTTAA

AACCCTATGTAAGATAAGGGAGGTGATTGTATCTGCGCCGTACTCCTTG

TTTTAATCTACCTGCTTGTTGTATATCCTCCACATATTGTAACTGCAGC

TTCACATTTGCATATATAGTAAGGGCATCGTTGTCTCCAGAAGAGATAT

ATTATC

MARKER 46432 (SEQ ID NO: 120): T→A
GCTGCCCGAATGTTACAATTAGGACGAAAGTAAAAGTAGTTGACTGTAG

GTATGACGATAAAGGAAAAATTTGTATCTTAAGACTTTACAATTTCTAA

ATATTACGTGTTTTATCGTGCTAACATCACGAATTCCATATTCACAAAA

AAAATTTTGTAGAACTCCATCTGGTTTGGATGAATTTGCTACAGTTGAA

CTGGATGATGGAACGAAATTGCAAACATCTCTTATTGTTAGTATTTTCT

AAATTCTGTGAAATTTTGCAACGGCATTCATGTTTAATTATTAATTTGG

AGAAAG

MARKER 29594 (SEQ ID NO: 121): T→A
AAATAAGCAAATCCGAAAGTATTACATATACGGACTAAATATTGCCATT

-continued

CATTCGGGAGTATACCATTGCAACCATTGGTATTTCATTTGATCGAGAA

AACTAGTTTTTGTAGTTTGGGATAAAGAGAAATGGAGAGAGGAACTTTC

ATGATCAATTTCTTTACGTACTGAAATTCATTTCTATGGATGTTCTTTT

TCTATTTCATTCTCCTCAGCAAATACAGTCCGAACAGTCATCAAATAAG

TCTAAAAGGCATGAATAATATAAACATCAGCAACTTTTTAAATGAATGC

TTATTA

MARKER 26784 (SEQ ID NO: 122): G→C
ATTTCTATAAACATCTCTTGCATTGATTAATTTAACATGTTGCAATAAA

TATTTCTTACTTTTGAATGTATCATTTACTAGAAAAAACTTCAATCGAG

GAAATAAGTTTTAAAATAAATTCATATTTGAATTCATGTCAGTTCAAAA

ATTCTATTACTATAATACATGTCTCTTGGTTGTATCTTTTTTTCTTTTG

AAATAATACAATCAAACGGTTTCCTAAATTTTCATAGACATCATATTTT

AAAAAAAAATGCATTTGAAAATTTTCGAAAATCAATGAACTTAATTGAT

GAAAAA

MARKER 51661 (SEQ ID NO: 123): C→G
GCATGTGTATGTAGTATTTCTTTGTAAACAACATATCTAATCTGTCTGT

CCCTTTAACATTATAGAATAGTCAGTTAGTCCGCTATTTATTTTAATAA

CAAAATATCTCACTTAACTTCCATTTCTTTCCTAAATAATTTTGTTTCG

CTAGATCTTTCCTATAATTTTCAAATTTTCAAAAATGAATTAATCTTTT

ATTTATATATGTGTATGTATGTGTATGTATGTGTACGTTGCATAT

ATGTATATGTATGTGTATGTGTATATGTATATGTATATGTGTA

TGTGTG

MARKER 7819 (SEQ ID NO: 124): G→C
TATGCATAATGTGCGACCAGCCAATAATGTCTTCAAACCATAATTATGC

AGAAATAAATTTTTTCCAGAAATAATTTTTTTTTTTTACATATACTTC

CGATCTGTGAGAAAATACATTTGAAGTGAAGTGTGAAGCAATGCTACTT

TTTCAAACAACATTGTGAAAATGGATTAAAACGCACCAATGGAGCAAGA

GATCGTAAGTTTCGTTCCGCATGTCCTGTGGCAACGTGTAAACCATCCG

TTAACGATATATGATGTAAAAGCCGACACACCCAAATTAAAATCCATTA

TAAACA

MARKER 26704 (SEQ ID NO: 125): G→C
AAATGGATCGTATTCACTTCGTAAGAACTTAGTGAACGAAAAATCAAAC

CATCACAATAACTTTACTTTTTTTCTTTTTTTACTAAACACACTATCCT

ATGAAAACAAAATGTCCAAATAGATTCATATGATAATGAACTGTGAAGT

TATCCAATCTATCAGTTCTCGAAGAGGGAATAAATAAAAACATTAAGCA

ACCCACCGATCTTCGCTGACCATCTCCTTCTTCATTAGCAAGAAGCAAA

TCTTGTGGTGATATTTCTGCAACCATCTGCAAAATAAAGCACGAAAAAT

TAAGGA

MARKER 14329 (SEQ ID NO: 126): C→A
TTTGATATGCAATCAACTAACCAAATCAGAATTCAATGCATTCTGATAA

ATTTCTTCAATATCGTGCATCAATTCGACATCATATTTTGACAGTGATG

CTACCTTTTTAGCCGTATTTCGGAAAAATATGAATTCAACCAGCTGCGT

CCCAAAATTTAAGGCTGTAGCAAGTCCAGCAACAACCAGCCCTACAACT

GAAAATTCTAAAAACTGGTTCACGTGCTTATCATTAATAATTTCAACAC

TATCACTATCTCCACATGAACTTGATCGATTATAATTTAGTAGAACTGA

AAAAAA

MARKER 56169 (SEQ ID NO: 127): T→G
ACAAATTCGTTTTAATATTGGATTACATTGAAATTGCTGAAATAAAGTG

GAAATATTGAAAAGCATTTTACAATATTTGTTAACAACATTATATTTAA

AGAATATACACCTTGGTTTAAATGGTAAAATAATCTCAAGAATTTTCAT

TAGGTTAATTTTTTTTATTTATTTATATTCACAAAAAATTGTAAAAGA

AAACAAAAACAACAATAATAACGGTGACAACAACAACAATAATAATAAC

AAAACTATTTGTTGTGATTTTGCAGCATTGATGTAGTGGGGATCTTTTG

GAGCGA

The genotype frequencies for each SNP (SEQ ID NOs: 110-127) at the polymorphic sites are shown in FIG. 29 (Table 1). In one analysis, genotype differences of susceptible individuals were compared with confirmed resistant individuals. In a second analysis, genotype differences of susceptible individuals were compared with grouped confirmed resistant and LOE individuals.

Kits and Methods

In embodiments of the invention, probes of the invention may be provided to a user as a kit. A kit of the invention may contain one or more probes of the invention. For example, a kit may comprise a probe capable of determining the genotype of a nematode at a SNP position in one of the fragments disclosed herein. The kit may further comprise one or more reagents, buffers, packaging materials, instructions for using the kit and containers for holding the components of the kit.

A probe of the invention may be one or more molecules that are capable of binding to, or associating with, the nucleic acid sample to determine the genotype of the nematode at one or more specific positions (e.g., polymorphic site) in the fragments disclosed herein. For example, probes may be used to determine whether a wild-type or alternative nucleotide is present at the SNP position of one or more of the fragments disclosed herein. An example probe may be a nucleic acid molecule or oligonucleotide. Example probes may contain a label or labels. Example labels may include radioactive labels, enzymatic labels and/or fluorescent labels.

An oligonucleotide used as a probe or primer may comprise any size, shape and composition that is suitable for use in the context of the invention. Preferably, an oligonucleotide of the invention may comprise DNA, RNA, synthetic nucleotides, non-natural nucleotides, altered nucleotides, or combinations of one or more thereof. In one embodiment, an oligonucleotide of the invention may comprise locked nucleic acids and/or peptide nucleic acids.

In embodiments of the invention, an oligonucleotide may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, or more nucleotides.

In embodiments of the invention, an oligonucleotide may encompass, without limitation, a primer or more than one primer, e.g. a primer pair, such as a forward primer and a reverse primer.

A primer may be an oligonucleotide that may be used to initiate DNA replication. Typically, a primer is a short oligonucleotide that may be about 10, about 15, about 20, about 25, about 30, about 35, about 40, about 45, about 50, about 55, about 60, about 65, about 70, about 75, about 80, about 85, about 90, about 95, about 100 or more nucleotides.

A primer may be used as part of an approach to detect the genotype of a nematode at a specific location of a gene. For example, a primer may be useful in amplifying DNA such as by PCR, RT-PCR and qRT PCR, for subsequent analysis, such as by Southern blot, sequencing, HRM (high resolution melt) or SSCP (single strand conformational polymorphism).

As used herein, an "aptamer" may be a nucleic acid or a peptide molecule that binds to a specific molecular target. For example, in solution, a chain of nucleotides may form intramolecular interactions that fold the aptamer into a complex three-dimensional shape. The shape of that aptamer allows it to bind tightly against the surface of its target molecule. Because of the diversity of molecular shapes that exists for nucleotide and amino acid sequences, aptamers may be obtained for a wide array of molecular targets, including, but not limited to, nucleic acid molecules, enzymes, membrane proteins, viral proteins, cytokines, growth factors, and immunoglobulins.

A probe of the invention may be prepared according to standard techniques known to a skilled person. For example, a probe may be produced synthetically, recombinantly or may be isolated from a natural source. In one embodiment, the source may be a biological source, for example, from a microorganism (e.g. a bacteria or a virus), an animal (e.g. a mouse, a rat, a rabbit, a goat, or a human), or a plant.

In the context of the invention, "a probe" may mean one probe or more than one probe. One or more types of probes may be simultaneously used in methods of the invention. Probe design and production are known in the art. Generally, a probe may be produced recombinantly, synthetically, or isolated from a natural source, e.g. from a cell, an animal or a plant. However, a skilled person would appreciate that probe production may depend on the type of probe at issue. A preferred probe may be a nucleic acid molecule (e.g. a primer), with or without a fluoroflor or dye. A probe may be linear or in the form of a hairpin, with a fluoroflor, with or without a quencher or another fluoroflor (e.g. for FRET analysis). It could also be an antibody that specifically recognizes the DNA (or protein) sequence. Another probe could be based on a RNA molecule. What would be preferred may depend on technical considerations, stability, cost, ease of use, etc.

In embodiments of the invention, probes of the invention may be provided to a user as a kit. A kit of the invention may contain one or more probes of the invention.

Uses of the Methods and the Kits

Methods of the invention and kits to carry out the methods may have research, medical and industrial applications. The invention finds broad application in the management of heartworms in infected animals and in detecting ML resistant *D. immitis* nematodes in an area. Representative, non-limiting applications of the invention may include the detection, quantification and/or diagnosis of the existence of individuals or populations of *D. immitis* that are not susceptible to normal doses of ML for prophylaxis or therapy. In one embodiment, the ability to detect and quantify nucleic acid molecules of the invention is valuable insofar as it will instruct a practicing veterinarian to alter chemotherapeutic regimens for animals infected with *D. immitis* nematodes that have decreased responsiveness to MLs. Identification of ML resistant *D. immitis* nematodes may instruct a veterinarian to switch from ML therapy alone to therapy that may include an alternative agent or alternative agents, such as an adulticide (e.g. arsenic based drugs), diethylcarbamazine, antibiotics such as tetracycline, and combinations of one or more thereof in order to achieve cure and/or to minimize the spread of the resistant strain. Alternatively, a veterinarian may adjust the dosage of a ML and/or treatment regimen using a ML in the treatment of an animal infected with a ML resistant nematode. Typical recommended dose rates for ML preventatives include, for example, 6 µg/kg for ivermectin; 500 mg/kg for milbemycin oxime; 3 µg/kg (monthly) moxidectin; and 6 mg/kg for selamectin. A veterinarian may also combine one or more of the treatment approaches and therapies noted above in any combination suitable to treat an animal infected with a *Dirofilaria* spp. nematode, e.g. a ML resistant *D. immitis* nematode. For example, a veterinarian may treat such an animal with an adulticide, such as an arsenic based drug, and then follow up with a microfilaricide, such as a ML or diethylcarbamazine.

In one instance, an arsenic based drug may be used to treat an animal infected with a ML resistant *D. immitis* nematode. An arsenic based drug may include, but is not limited to, melarsomine dihydrochloride. Melarsomine dihydrochloride may be used, for example, at a dose of 2.5 mg/kg, twice, 24 hours apart. This may be repeated in 4 months depending on the response to the first treatment and the condition, age, and use of the animal. However, a skilled person would understand that the dosage may vary depending on the severity of the infection. For example, an infected animal such as a dog with severe (class 3) disease may receive one dose and allowed to recover for a few months before receiving the complete set of 2 doses.

In another instance, diethylcarbamazine may be used to treat an animal infected with a ML resistant *D. immitis* nematode. Diethylcarbamazine may be used, for example, at a dose of 25 to 50 mg per pound of an animal. The duration of administration may depend on the condition being treated, response to the medication and the development of any adverse effects.

In another instance, an antibiotic may be used to treat an animal infected with a ML resistant *D. immitis* nematode. Said antibiotic may include, but is not limited to, tetracycline. A tetracycline, such as doxycycline, which targets the *Wolbachia* endosymbionts in *D. immitis* may be used, for example, at a dose of 10 mg/kg/day for 40 days.

In a further instance, another anthelminthic agent may be used. Such other anthelminthic agent may include, but is not limited to, acaciasides. An acaciaside may be used, for example, at a dose of 10 mg/kg/day for 7 days.

In another embodiment, the detection of *D. immitis* nematode populations with the above mentioned genotypes may instruct the use of alternative agents, such as diethylcarbamazine as a prophylactic to protect susceptible animals, e.g. dogs.

In one instance, diethylcarbamazine may be used to prevent an animal from becoming infected with a ML resistant *D. immitis* nematode. In this regard, diethylcarbamazine may be used, for example, at a dose of 3 mg per pound of an animal once daily.

In another embodiment, a kit of the invention may be useful in as a commercial product in the detection of ML resistant *D. immitis* nematodes. Such a product may be suitable for use by, without limitation, a veterinarian, a physician, a pet owner, a farmer, a zoo keeper, an epidemiologist, or another consumer in need thereof.

EXAMPLES

The examples are for the purpose of illustrating an example and are not to be construed as illustrating limitations.

Example 1—Susceptible and LOE Populations of *D. immitis* Parasites Used in the Studies The various susceptible and LOE populations of *D. immitis* used in these studies are described below.
   a. Susceptible isolates from Missouri. USA. Thirty five (35) *D. immitis* adult specimens were obtained from two dogs originating from an animal pound in Missouri. The history of the dogs prior to the animal pound is not known. The dogs were not subsequently treated. The *D. immitis* isolates were believed to be susceptible to ML heartworm preventatives.
   b. Susceptible isolates from Grand Canary, Spain. Seventy-one (71) *D. immitis* adult specimens were obtained from 12 dogs originating from a shelter on Grand Canary. The dogs were never exposed to ML heartworm preventatives and heartworm prevention is not practiced in this region of Grand Canary.
   c. Susceptible isolates from Grenada. WI. Ten (10) *D. immitis* adult specimens were obtained from 2 dogs originating from Grenada. The dogs were recruited from poor, remote areas of the island where ML heartworm prevention is not practiced.
   d. Susceptible isolates from Italy, Six (6) *D. immitis* adult specimens were obtained from the Po Basin in northern Italy. *D. immitis* seroprevalence in dogs from this area is reported to be approximately 60-70%. ML heartworm preventatives are commonly given to dogs in this area. But, there are no reports of LOE (loss of efficacy) in Italy.
   e. Loss of efficacy (LOE) isolate case 1. Microfilariae (mt) were isolated from a dog that was previously described (see Bourguinat et al.; W0201 1/120165). The dog was a male neutered Labrador mix, born in February, 2006, that weighed approximately 31 kg. He was a rescue dog from New Orleans, Louisiana, U.S.A., collected by the Boudreaux Rescue Crew, New Orleans, and subsequently transferred to Canada where he was adopted in January, 2008.

The dog was brought to the Main West Animal Hospital (MWAH) in Welland, Ontario on Jun. 6, 2008 (day 1) for a check-up. Blood collected from the dog tested positive with a heartworm antigen test (PETCHEK® PF; IDEXX Laboratories, Westbrook, Maine) and contained microfilariae of *D. immitis*. On Jun. 11, 2008 (day 6), initial work-up (bloodwork, thoracic radiographs, physical exam, urinalysis) was performed. Auscultation revealed a mild increase in bronchovesicular sounds in the lungs and a grade III-IV/VI heart murmur. The remainder of the physical exam was unremarkable. Thoracic radiography revealed moderate right-sided heart enlargement and an interstitial lung pattern in the caudodorsal lung field. These examinations indicated a diagnosis of class 2 heartworm disease.

Adulticide treatment was initiated on Jun. 11, 2008 (day 6) with 2.5 mg/kg intramuscular melarsomine dihydrochloride (IMMITICIDE®; Merial Inc.). The treatment was followed by two intramuscular treatments with 2.5 mg/kg melarsomine dihydrochloride on July 9 and July 10 (days 34, 35). Over the following 90 days, in order to eliminate circulating mf, the dog was treated on one occasion with milbemycin oxime (MO) and on two occasions with IVM (see Table 2). On days 159 and 160, four months after the last dose of adulticide, the dog was again treated with 2.5 mg/kg melarsomine dihydrochloride intramuscularly. The subsequent diagnostic testing and microfilaricidal treatments are summarized in Table 2. During the treatment of the dog, several heartworm antigen tests were conducted, including DIROCHEK® (Synbiotics Corporation, San Diego, California) and PETCHEK® (IDEXX Laboratories, Westbrook, Maine), which are microwell ELISA tests, and SNAP® PF (IDEXX Laboratories, Westbrook, Maine, a membrane format test designed for rapid in-clinic use (see Table 2).

To perform the Knott's test, 9 ml of 2% formalin and 1 ml blood (collected in EDTA) were mixed in a centrifuge tube. Centrifugation was performed in a LW Scientific EZ Swing SK centrifuge at 3000 rpm (604 m/s2) for 5 min. The supernatant fluid was discarded. A drop of 0.1% methylene blue solution was added to the pellet at the bottom of the centrifuge tube, mixed, and a drop of stained mixture examined under the microscope for *D. immitis* microfilariae. Table 2 indicates when this test was carried out and, when determined, the level of microfilaremia.

The dog was treated as follows. Two days after the last of three doses of melarsomine dihydrochloride in July 2008 (i.e., on day 37), the dog showed transitory signs consistent with death of adult heartworms (elevated rectal temperature, lethargy, cough, increased lung sounds). Beginning on day 41, these signs were managed with prednisone (Apo-Prednisone; Apotex, Toronto, ON, Canada), 1.3 mg/kg bid for 6 days. Following the administration of milbemycin oxime (MO) per os at 0.74 mg/kg on day 74, IVM per os at 50 ug/kg on day 95, and IVM per os at 200 ug/kg (4× the normal microfilaricidal dose rate) on day 125, the dog remained continually microfilaremic. On day 207, six weeks after the second treatment regimen of melarsomine dihydrochloride, on days 159 and 160, a Knott's test was still positive, so the dog was again treated with 200 µ/kg IVM per os. One month later, on day 242, a *D. immitis* antigen test was negative, which confirmed that the dog was free of adult worms. However, the dog was still microfilaremic. Thus, beginning on day 243, the dog was given MO per os at 0.74 mg/kg every 2 weeks on four occasions (see Table 2). Despite this, the dog remained microfilaremic on day 298. It was therefore administered MO per os at 1.1 mg/kg on days 298, 312, 326, 340 and 354. On day 356, blood was collected from the dog and examined: microfilariae were still present, and a *D. immitis* antigen test was still negative. On day 375, a blood sample was sent to Animal Health Laboratory, University of Guelph (AHLUG): microfilaremia was 6530 mf/ml, and an antigen test was still negative (see Table 2). As a result, beginning on day 384, the dog was administered MO per os at 2.0 mg/kg once daily for 7 days. On day 420, the dog had a microfilaraemia of 355 mf/ml. On day 420, the dog was again treated with MO per os at 2.0 mg/kg, and this was continued once daily for 8 days. Despite this second high-dose regimen, on day 480, while still testing negative with a heartworm antigen test, the dog had a microfilaremia of 1810 mf/ml.

Blood was collected from the dog on day 706 and DNA was isolated from pooled microfilariae.

TABLE 2

Diagnostic testing and treatment history for dog between 2008 and 2009

| Date (day) | Antigen test Name-result (+ve or −ve) | Adulticide (melarsomine)* dosage | Microfilariae concentration in blood (mf/ml) | Microfilaricide drug dosage (PO) | Comments |
|---|---|---|---|---|---|
| 2008 | | | | | |
| June 6 (1) | PetChek +ve[a] | | | | |
| June 11 (6) | | 2.5 mg/kg | Knott's test +ve[a] | | Classified as Class 2 heartworm disease |
| July 9 (34) | | 2.5 mg/kg | | | |
| July 10 (35) | | 2.5 mg/kg | | | |
| August 18 (74) | | | | MO, 0.74 mg/kg | |
| September 3 (90) | | | Knott's test +ve[a] | | |
| September 8 (95) | | | | IVM, 50 µg/kg | |
| October 6 (123) | | | Knott's test +ve[a] | | |
| October 8 (125) | | | | IVM, 200 µg/kg | |
| November 10 (158) | | | Knott's test +ve[a] | | |
| November 11 (159) | | 2.5 mg/kg | | | |
| November 12 (160) | | 2.5 mg/kg | | | |
| December 12 (190) | | | | MO, 0.74 mg/kg | |
| December 29 (207) | | | Knott's test +ve[a] | | |
| December 30 (208) | | | | IVM, 200 µg/kg | |
| 2009 | | | | | |
| February 2 (242) | SNAP −ve[a] | | Knott's test +ve[a] ≥100[b] | | Interpretation: no adult heartworms |
| February 3 (243) | | | | MO, 0.74 mg/kg | |
| February 17 (257) | | | | MO, 0.74 mg/kg | |
| March 3 (271) | | | Knott's test +ve[a] ≥100[b] | MO, 0.74 mg/kg | |
| March 17 (285) | | | | MO, 0.74 mg/kg | |
| March 30 (298) | | | Knott's test +ve[a] ≥100[b] | MO, 1.1 mg/kg | |
| April 13 (312) | | | | MO, 1.1 mg/kg | |
| April 27 (326) | | | | MO, 1.1 mg/kg | |
| April 28 (327) | | | Knott's test +ve[a] | | |
| May 11 (340) | | | | MO, 1.1 mg/kg | |
| May 25 (354) | | | | MO, 1.1 mg/kg | |
| May 27 (356) | SNAP −ve[a] | | Knott's test +ve[a] | | no adult heartworm |
| June 8 (368) | | | | MO, 1.1 mg/kg | |
| June 15 (375) | DiroChek −ve[c] | | Knott's test +ve[c] 6530 | | no adult heartworm |
| June 24 (384) | | | | MO, 2.0 mg/kg daily for 7 days | |
| July 30 (420) | | | Knott's test +ve[c] 355 | MO, 2.0 mg/kg daily for 8 days | |
| September 28 (480) | PetChek −ve[a] | | Knott's test +ve[c] 1810 | | |

TABLE 2-continued

Diagnostic testing and treatment history for dog between 2008 and 2009

| Date (day) | Antigen test Name-result (+ve or −ve) | Adulticide (melarsomine)* dosae:e | Microfilariae concentration in blood (mf/ml) | Microfilaricide drug dosage (PO) | Comments |
|---|---|---|---|---|---|
| 2010 | | | | | |
| May 12 (706) | | | | | Microfilariae collected for DNA isolation |

MO = milbemycin oxime (INTERCEPTOR ®);
IVM = ivermectin (IVOMEC ® Injection for cattle, sheep and swine, Merial Inc.);
*Adulticide = IMIMITICIDE ®;
$^a$= Main West Animal Hospital (i.e. test carried out in house);
$^b$= Idexx Laboratories;
$^c$= Animal Health Laboratory, University of Guelph.

f. LOE isolate case 2. Approximately 9000 pooled mfwere obtained from a dog from Mechanicsville, Virginia, that had been treated with INTERCEPTOR® from 2004 to 2008. In May 2008, the dog was heartworm antigen positive and was placed on HEARTGARD® Plus (IVM/PYR) for slow kill treatment. In 2008, the dog was still positive for heartworm antigen and was still microfilaremic. From Dr Blagburn's (Auburn University) in vitro assay: LD9s concentration for susceptible mf produced only a 10.5% kill, and 2× LD9s produced a 13.6% kill of mf.

g. LOE isolate case 3. Pooled mfwere obtained from low responder mf from an in vitro ivermectin susceptibility assay. The dog was a naturally infected client-owned animal, from Monroe, Louisiana, selected because it had been on ML heartworm preventative treatment. The veterinarian was convinced that compliance was not an issue. Patient records indicated that proper amounts of product had been provided to the client, based on numbers and weights of target animals in the household. The dog was microfilaremic despite the fact that it had been under ML heartworm prophylaxis.

h. LOE isolate case 4. Pooled mfwere obtained from a dog that had the history as described below. This stray dog originated from Haywood County, Tennessee, USA, and presented as heartworm antigen positive to a local clinic on Jan. 21, 2011. The dog was neutered on Jan. 26, 2011. On Feb. 1, 2011, doxycycline (200 mg orally twice per day) and prednisone (1 5 mg tablet orally every other day) therapy was initiated and continued for 30 days. On February 2, March 3 and Mar. 4, 2011, an injection of melarsomine dihydrochloride (IMMITI-CIDE®) (2.5 mg/kg) were given. On February 2, March 3 and Apr. 1, 2011, an oral dose of milbemycin oxime (INTERCEPTOR®) (11.5 mg/tablet) was given. On Apr. 5, 2011, a Knott's test was performed and was positive; ivermectin was administered subcutaneously at a dose of 0.26 mg/kg. On Apr. 11, 2011, Knott's test was again positive; ivermectin was administered subcutaneously at a dose of 0.39 mg/kg. Knott's tests were again performed on both April 19 and 26, 2011 and were both positive. On May 2, 2011, Knott's test was again positive and a blood smear showed microfilariae; ADVANTAGE MULTI® (2.5% imidacloprid, 10% moxidectin) was administered to the dog. On May 5, 2011, a blood smear was positive for microfilariae; at this time, microfilariae were collected. The repeated adulticide treatment led to the assumption they the dog was free of adult parasites. On Jun. 11, 2011, 200 mg of diethylcarbamazine was administered to the dog. No side effects of the treatment were noted. Within 7 days, the blood smear showed no mf. The dog was adopted on Aug. 18, 2011 and moved to Massachusetts.

i. LOE isolate case 5. Pooled mfwere obtained from a dog originating from West Monroe, Louisiana, USA. This was a veterinarian's dog. The medical history implied compliant use of milbemycin oxime and there were several negative heartworm antigen tests at annual check-ups, until a positive heartworm antigen test and presence of mf in the blood on Sep. 25, 2008. An in vitro microfilaria sensitivity assay was performed (B. Blagburn laboratory, Auburn University, Alabama) on Nov. 19, 2008. The results of the assay indicated drug-resistant organisms. Mosquitoes were fed on infected blood samples from this original dog. L3 larvae were used to infect a second dog. At the time of infection, the second dog had been under treatment with ivermectin. Thereafter, at weekly intervals, the second dog received 1 dose of 3 μg ivermectin/kg, followed by 11 doses of 6 μg ivermectin/kg, followed by 4 doses of 12 μg ivermectin/kg, followed by 8 doses of 24 μg ivermectin/kg (interrupted for one week after the 4th dose). During the entire period of weekly dosing with ivermectin, the dog was remained positive for mf. Microfilariae were collected at 1 and 2 weeks after the last treatment were used in the analysis.

j. LOE isolate case 6. The samples correspond to the second passage of parasite that came from a dog originally from Earle, Arkansas, USA. The original isolate LOE-6 dog received milbemycin oxime in 2004 and 2005, ivermectin/pyrantel in 2006 and 2007, and ivermectin/praziquantel/pyrantel (IVERHART MAX™) in January 2008 and at the beginning of July 2008. The owner stated that she had been consistent with prophylaxis. This dog tested negative for heartworm antigen at annual check-ups in 2005, 2006 and 2007. This dog was positive for heartworm antigen and microfilaremic at the annual exam on Nov. 4, 2008. Results of the in vitro microfilaria assay (B. Blagburn laboratory, Auburn University, AL) on this dog suggested resistance. Dog-LOE-6, was experimentally infected on Nov. 16, 2009 with L3 larvae derived from mosquitoes fed with blood from the first passage. The first passage dog was experimentally infected on Feb. 24, 2009 with L3 larvae derived from mosquitos fed with blood from a naturally infected dog (the original isolate LOE-6 dog).

Example 2—DNA Isolation from Parasites Used in the Studies

Genomic DNA for the individual adult worms was extracted with DNEASY™ kit from Qiagen (Qiagen Inc, Mississauga, Canada). The genomic DNA extraction of individual mfwas extracted using QTAAMP® DNA Micro kit from Qiagen. To obtain enough DNA for analysis, the mfDNA was amplified using a REPLI-G® kit from Qiagen which allow amplifying the full genome from a very small amount of DNA. Mfwere isolated by filtration through polycarbonate membrane filters from freshly drawn blood.

Example 3—DNA Sequencing, Analysis and Identification of SNPs

The goal was to identify genetic changes (e.g., nucleotide variations) present in LOE heartworm populations that were not present in the susceptible heartworm populations. Nucleotide variations in any of the LOE populations, as compared to a reference genome obtained from the susceptible isolates, would indicate potential SNP markers.

Initially, the genomes from the heartworm populations identified in lettered paragraphs a-h of Example 2 above (susceptible isolates from Missouri, Grand Canary Island, Grenada and Italy; LOE isolates cases 1-4) were sequenced using the HISEQ™2000 system from ILLUMINA®. Table 3 shows the number of reads and the number of bases that were sequenced for each population. Not included in Table 3 is information from heartworm populations identified in paragraphs i and j (resistant isolates from LOE cases 5 and 6).

TABLE 3

Read information on isolates used for whole genome sequencing

| Isolates | Number of reads | Number of bases |
| --- | --- | --- |
| 1 - susceptible | 85,097,000 | 17,019,400,000 |
| 2 - susceptible | 78,242,862 | 15,648,572,400 |
| 3 - susceptible | 80,687,895 | 16,137,579,000 |
| 4 - susceptible | 75,515,617 | 15,103,123,400 |
| 5 - LOE-1 | 82,417,743 | 16,483,548,600 |
| 6 - LOE-2 | 74,261,369 | 14,852,273,800 |
| 7 - LOE-3 | 79,894,844 | 15,978,968,800 |
| 8 - LOE-4 | 75,477,318 | 15,095,463,600 |

The data generated from the ML susceptible samples (susceptible isolates from Missouri, Grand Canary Island, Grenada and Italy) were used to assemble the genome which was then used as the reference genome for the project. All of the individual fragments from the 4 susceptible populations were pooled together. Velvet aligner software (European Bioinformatics Institute) was used to assemble the genome. Reads were filtered by having the adaptor sequences removed/clipped, if found. Reads were trimmed at Q30 length 32 base pairs. A length of 32 base pairs is the Aligner seed default value and the number of reads was consistent with the default value. Table 4 describes the assembly of the reference genome used for the study.

TABLE 4

Information about the D. immitis genome assembly

| | |
| --- | --- |
| Number of contigs | 22 966 |
| 50% of the contigs are longer than | 28 928 bp |
| Length of longest contig | 250 211 bp |
| Total bases in contigs | 94 611 006 (94 Mb) |
| Number of contigs >1 kb | 6654 |
| Total bases in contigs >1 kb | 90 045 376 bp (90 Mb) |

Once the reference heartworm genome was obtained from sequences of the susceptible isolates/populations, then the genomes from the LOE populations were compared to the reference genome, to identify differences and possible SNPs. As part of this analysis, genetic loci containing the potential SNPs were shown not to be significantly different between the individual susceptible populations (i.e., between the susceptible isolates from Missouri, Grand Canary Island, Grenada and Italy), as well as not to be significantly different between the individual LOE populations (LOE 1-4), but were significantly different between the susceptible populations and the LOE populations. To perform this analysis, the software program called PoPoolation2 (Kofler et al. Bioinformatics 27: 3435-3436, 2011) was used. The program required the use of other programs, such as Perl, R, bwa, and Samtools. First, a synchronized file was generated, which contained the nucleotide frequencies for every population at every base in the reference genome, after filtering for base quality, in a concise format. The synchronized file generated with the PoPoolation2 program contained detailed nucleotide count information on loci for each of the populations. P-values were generated with Fisher's exact test for all the possible comparisons between populations. To identify loci associated with ML resistance, p-values needed to be simultaneously not statistically significant($>0.05$) within all susceptible samples and within all the LOE samples, and statistically significant($<0.05$) between all susceptible versus all LOE samples. Three hundred thirty eight loci met these criteria, including 12 that had a p-value of 10-5, Flanking regions of 1000 bp including each locus that was statistically different between the susceptible and LOE samples were analyzed by Blast (BlastN and BlastX) in NCBI and in the Broad Institute filarial genome database to remove loci located in mitochondrial, Wolhachia or C. lupus familiaris DNA. Loci located in reads with very high polymorphism($>2$ nucleotides and/or indels) or low coverage($<10\times$) were removed from further analysis. Nucleotide counts for each locus of interest were analyzed individually for the pooled populations to ensure that the increase or decrease in nucleotide frequency was in the same direction for all the susceptible samples or for all the LOE samples. The loci that best met the criteria were retained for further genotype analysis on individual parasites to assess actual allele frequencies in populations that had been characterized in terms of ML response.

From these analyses, 186 loci were found to be significantly different between the susceptible and LOE samples. As this approach was based on reads and nucleotide frequencies of pooled samples, these loci were further studied (SNP genotyping) using individual (not pooled) populations. For this purpose, SEQUENOM® SNP frequency analysis was used. Table 5, below, shows the origins of the DNA used in this analysis.

TABLE 5

Description of isolates used for SEQUENOM® analysis

| | State and/or country of origin | # Individual adult worm | # Individual microfilaria | From # dogs |
|---|---|---|---|---|
| Susceptible samples = 181 isolates | | | | |
| Sus1-Missouri | Missouri isolate, USA | | 49 | 1 |
| Sus2-Missouri | Missouri isolate, USA | | 45 | 1 |
| Grand Canary | Grand Canary, Spain | 71 | | 11 |
| Grenada | Grenada, WI | 10 | | 2 |
| Italy | Northern Italy | 6 | | |
| Low responder samples = 244 Isolates | | | | |
| LOE-1 | New Orleans, LA, USA, moved to Ontario, Canada | | 56 | 1 |
| LOE-2 | Mechanicsville, VA, USA | | 35 | 1 |
| LOE-3 | Monroe, LA, USA | | 51 | 1 |
| LOE-5 | West Monroe, LA, USA | | 54 | 1 |
| LOE-6 | Earle, AR, USA | | 48 | 1 |

SEQUENOM® analysis is based on multiplex PCR and MALDI-TOF mass spectrometry. The SEQUENOM® analysis was used to evaluate the 186 loci using 425 individual samples (5 panels with 36-38 SNPs in each panel). Primer design for each SNP marker was based on a requirement that elongation primers be located in a non-polymorphic region 15 base pairs before or after the SNP of interest. All the genome calls were performed blinded (i.e., the sample origin and dog treatment history was not known during the analysis). A total of 79050 genotypes were analyzed. From the 186 potential loci, 109 were observed to have technical advantages to predict for ML loss of efficacy. The susceptible population carried more than 90% of the wild-type genotype while the LOE population had a significant lower genotype frequency of the wild-type genotype. These 109 loci are disclosed herein as SEQ ID NOs: 1-109.

Example 4—Additional SNPs from Confirmed Resistant Organisms

LOE samples, as described in Example 1, were presumed to be resistant to MLs because of the history of treatment of the dogs with MLs and the continued presence of heartworm organisms. However, despite the history of treatment, an alternative explanation to true ML-resistance of the parasites is owner non-compliance of ML treatment. Therefore, a study was performed under controlled ML treatment conditions, to eliminate the possibility of owner non-compliance in ML treatment, as a possible reason for presence of heartworm organisms in dogs.

Heartworm organisms used in the efficacy studies were derived from one identified as Jd2009 from Earle, Arkansas, USA. Jd2009 received monthly MO in 2004 and 2005, IVM/pyrantel in 2006 and 2007, and IVM/praziquantel/pyrantel in January 2008 until early July 2008. Jd2009 tested negative for HW antigen in 2005, 2006, and 2007. This dog was heartworm antigen positive and microfilaremic on Apr. 11, 2008 despite a history of compliance with HW preventatives. Mf were obtained from the dog at this time with the consent of the owner and were sent to Auburn University, where the mf were examined for sensitivity to IVM in an in vitro concentration-response assay measuring migration (Blagburn, B., American Heartworm Society-13th Triennial State of the Heartworm Symposium, 2010). These mf were significantly less sensitive to IVM than mf obtained from a dog infected with a laboratory strain of D. immitis that was fully susceptible to the drug. The mf were used at Auburn University to infect mosquitoes to produce L3 that were used to infect dog Jd2009-1, which developed a patent infection. Mf from this dog were shown to be as resistant to ML as mf from Jd2009 in the in vitro migration assay.

L3s derived from mf harvested from Jd2009-1 were used at Auburn University to infect a second dog, Jd2009-2 and the dog was treated monthly with HEARTGARD PLUS® (0.006-0.013 mg/kg IVM) 9 consecutive times. Adult worms were recovered indicating that the Jd2009-2 isolate was resistant to IVM prophylaxis. In a second study, dogs were challenged with Jd2009-2 L3 on day O and treated monthly for 5 consecutive months with HEARTGARD PLUS® (0.007-0.009 mg/kg IVM; Study 1b). At necropsy on day 188, efficacy was 71.3%, confirming resistance to IVM prophylaxis in the Jd2009-2 isolate.

In another study, dogs were challenged with L3 on day 180 after PROHEART6® injection. At necropsy on day 150 after infection, efficacy was 21.6%, indicating that the Jd2009-2 was also resistant to the PROHEART6@long acting formulation of MOX, which has a claim for 100% protection for 180 days after treatment.

In another study, the confirmed IVM-resistant isolate Jd2009-2 was used to determine whether the resistance extended to other ML heartworm preventatives. None of the other ML heartworm preventatives (MOX, MO and SEL), given as monthly chemoprophylaxis as recommended, was fully effective, i.e., at least one dog in groups of four to six dogs on these heartworm preventatives became infected with D. immitis following treatment with each of these MLs used as recommended.

DNA from individual organisms from two Jd2009 isolates were used. DNA from individuals from one group, called RES-1, came from 4 dogs from the PROHEART6® study, described above. DNA from individuals from another group, called RES-2, came from 6 dogs from the HEARTGARD PLUS® study, described above.

DNA was isolated from 115 adult worms and 79 mf from the RES-1 and RES-2 populations, as described in Example 2, and were analyzed using SEQUENOM® SNP frequency analysis, as described in Example 3. From this analysis, 18 additional loci (out of the initial 186 loci) were significantly different between the susceptible and RES samples. These loci are disclosed herein as SEQ ID NOs: 110-127.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the disclosure is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

The invention claimed is:

1. A method of treating an animal infected with a *Dirofilaria* spp. nematode, the method comprising determining the genotype of the nematode at a polymorphic site in a nucleic acid molecule that includes SEQ ID NO: 118, wherein the polymorphic site at position 151, wherein if position 151 is G, then the animal is treated with an alternative agent, and wherein if position 151 is not G, then the animal is treated with a macrocyclic lactone.

2. The method of claim 1, wherein the alternative agent comprises one or more of an arsenic-based therapy, diethylcarbamazine, and antibiotics.

3. The method of claim 2, wherein the arsenic-based therapy is melarsomine dihydrochloride.

4. The method of claim 3, wherein the melarsomine dihydrochloride is administered to the animal intramuscularly.

5. The method of claim 2, wherein the antibiotic is tetracycline.

6. The method of claim 2, wherein the antibiotic is doxycycline.

7. The method of claim 1, wherein the *Dirofilaria* spp. nematode is *Dirofilaria immitis*.

8. The method of claim 1, including isolating the nucleic acid molecule from the nematode, and optionally purifying the nucleic acids prior to determining the genotype of the nematode.

9. The method of claim 1, wherein the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, and qRT-PCR.

10. The method of claim 1, wherein the genotype of the nematode is determined by DNA sequencing.

11. The method of claim 1, wherein the genotype of the nematode is determined by hybridization-based methods including with allele specific oligonucleotides.

12. The method of claim 1, wherein the genotype of the nematode is determined by microarray analysis.

13. The method of claim 1, wherein the genotype of the nematode is determined by enzyme-based methods.

14. The method of claim 1, wherein the genotype of the nematode is determined by single strand conformational polymorphism (SSCP).

15. The method of claim 1, wherein the genotype of the nematode is determined by high resolution melt (HRM).

16. The method of claim 1, wherein the genotype of the nematode is determined by one or more of PCR, RT-PCR, and qRT-PCR.

\* \* \* \* \*